United States Patent
Blumberg et al.

(10) Patent No.: US 9,416,137 B2
(45) Date of Patent: *Aug. 16, 2016

(54) MORPHAN AND MORPHINAN ANALOGUES, AND METHODS OF USE

(71) Applicant: ALKERMES PHARMA IRELAND LIMITED, Dublin (IE)

(72) Inventors: Laura Cook Blumberg, Lincoln, MA (US); Daniel R. Deaver, Franklin, MA (US); David J. Eyerman, Wayland, MA (US); Thomas Andrew Wynn, Lexington, MA (US)

(73) Assignee: ALKERMES PHARMA IRELAND LIMITED, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 14/833,334

(22) Filed: Aug. 24, 2015

(65) Prior Publication Data

US 2015/0376197 A1 Dec. 31, 2015

Related U.S. Application Data

(62) Division of application No. 14/286,456, filed on May 23, 2014, now Pat. No. 9,133,125.

(60) Provisional application No. 61/827,210, filed on May 24, 2013.

(51) Int. Cl.
| | |
|---|---|
| *A61K 31/4748* | (2006.01) |
| *C07D 221/28* | (2006.01) |
| *C07D 489/00* | (2006.01) |
| *C07D 221/26* | (2006.01) |
| *C07D 405/06* | (2006.01) |
| *A61K 31/485* | (2006.01) |

(52) U.S. Cl.
CPC ............ *C07D 489/00* (2013.01); *A61K 31/485* (2013.01); *C07D 221/26* (2013.01); *C07D 221/28* (2013.01); *C07D 405/06* (2013.01)

(58) Field of Classification Search
USPC ............................................ 514/289; 546/74
See application file for complete search history.

(56) References Cited

U.S. PATENT DOCUMENTS

| | | |
|---|---|---|
| 3,332,950 A | 7/1967 | Blumberg et al. |
| 3,856,795 A | 12/1974 | Yardley |
| 3,957,793 A | 5/1976 | Wentland et al. |
| 4,032,529 A | 6/1977 | Wentland et al. |
| 4,100,288 A | 7/1978 | Merz et al. |
| RE29,943 E | 3/1979 | Wentland et al. |
| 4,161,597 A | 7/1979 | Olofson et al. |
| 4,176,186 A | 11/1979 | Goldberg et al. |
| 4,205,171 A | 5/1980 | Albertson |
| 4,374,139 A | 2/1983 | Mohacsi |
| 4,451,470 A | 5/1984 | Ganti |
| 4,464,378 A | 8/1984 | Hussain |
| 4,473,573 A | 9/1984 | Merz et al. |
| 4,489,079 A | 12/1984 | Giudice et al. |
| 4,649,200 A | 3/1987 | Portoghese et al. |
| 4,929,622 A | 5/1990 | Allen et al. |
| 5,258,386 A | 11/1993 | Newman et al. |
| 5,607,941 A | 3/1997 | Merz et al. |
| 5,847,142 A | 12/1998 | Mudiyk et al. |
| 6,365,594 B1 | 4/2002 | Dondio et al. |
| 6,784,187 B2 | 8/2004 | Wentland |
| 6,812,236 B2 | 11/2004 | Gibson et al. |
| 6,887,998 B2 | 5/2005 | Wentland |
| 7,244,866 B2 | 7/2007 | Carson et al. |
| 7,262,298 B2 | 8/2007 | Wentland |
| 7,265,226 B2 | 9/2007 | Wentland |
| 7,557,119 B2 | 7/2009 | Wentland |
| 7,956,187 B2 | 6/2011 | Wentland |
| 8,026,252 B2 | 9/2011 | Wentland |
| 8,252,929 B2 | 8/2012 | Wentland |
| 8,354,534 B2 | 1/2013 | Arnelle et al. |
| 8,642,615 B2 | 2/2014 | Wentland |
| 8,680,112 B2 | 3/2014 | Wentland |
| 8,778,960 B2 | 7/2014 | Deaver et al. |
| 8,802,655 B2 | 8/2014 | Wentland |
| 8,822,488 B2 | 9/2014 | Deaver et al. |
| 9,133,125 B2 | 9/2015 | Blumberg et al. |
| 9,211,293 B2 | 12/2015 | Deaver et al. |
| 2002/0099216 A1 | 7/2002 | Gibson et al. |
| 2003/0181475 A1 | 9/2003 | Kaiko et al. |
| 2004/0192715 A1 | 9/2004 | Chasin et al. |

(Continued)

FOREIGN PATENT DOCUMENTS

| | | |
|---|---|---|
| EP | 0 254 120 A2 | 1/1988 |
| EP | 0 632 041 A1 | 1/1995 |

(Continued)

OTHER PUBLICATIONS

Wentland et al. (2009) "Syntheses and Opioid Receptor Binding Properties of Carboxamido-Substituted Opioids," Bioorganic & Medicinal Chemistry. 19(1):203-208.

Yamamoto et al. (2006) "Buprenorphine Activates µ and Opioid Receptor Like-1 Receptors Simultaneously, but the Analgesic Effect Is Mainly Mediated by µ Receptor Activation in the Rat Formalin Test," Journal of Pharmacology and Experimental Therapeutics. 318(1):206-213.

Zaveri et. al. (2005) "Small-Molecule Agonists and Antagonists of the Opioid Receptor-Like Receptor (ORL 1, NOP): Ligand-Based Analysis of Structural Factors Influencing Intrinsic Activity at NOP," AAPS Journal. 2005:E345-E352.

Zhang et al. (2004) "10-Ketomorphinan and 3-Substituted 3-desoxymorphinan Analogues as Mixed κ and µ Opioid Ligands: Synthesis and Biological Evaluation of Their Binding Affinity at Opioid Receptors," J. Med. Chem. 47:165-174.

(Continued)

*Primary Examiner* — Charanjit Aulakh
(74) *Attorney, Agent, or Firm* — Lathrop & Gage LLP; Brian C. Trinque; Jana A. Lewis

(57) ABSTRACT

The present application relates to analogues of morphan and morphinan, compositions thereof, and methods for treating a disease or condition comprising administering an effective amount of the compounds or compositions to a subject in need thereof.

17 Claims, 9 Drawing Sheets

(56) References Cited

U.S. PATENT DOCUMENTS

| | | | |
|---|---|---|---|
| 2004/0254208 | A1 | 12/2004 | Weber et al. |
| 2005/0113401 | A1 | 5/2005 | Lawson |
| 2005/0176645 | A1 | 8/2005 | Mickle et al. |
| 2005/0182258 | A1 | 8/2005 | Schmidhammer et al. |
| 2005/0215799 | A1 | 9/2005 | Wentland et al. |
| 2006/0030580 | A1 | 2/2006 | Wentland |
| 2006/0063792 | A1 | 3/2006 | Dolle et al. |
| 2007/0021457 | A1 | 1/2007 | Wentland |
| 2007/0099947 | A1 | 5/2007 | Dean et al. |
| 2007/0238748 | A1 | 10/2007 | Wentland |
| 2008/0004324 | A1 | 1/2008 | Barak |
| 2008/0234306 | A1 | 9/2008 | Perez et al. |
| 2009/0053329 | A1 | 2/2009 | Peters et al. |
| 2009/0197905 | A1 | 8/2009 | Wentland |
| 2009/0209569 | A1 | 8/2009 | Arnelle et al. |
| 2009/0247562 | A1 | 10/2009 | Wentland |
| 2009/0311347 | A1 | 12/2009 | Oronsky |
| 2010/0035910 | A1 | 2/2010 | Wang et al. |
| 2010/0048906 | A1 | 2/2010 | Wang et al. |
| 2010/0130512 | A1 | 5/2010 | Wentland |
| 2010/0190817 | A1 | 7/2010 | Wentland |
| 2010/0240691 | A1 | 9/2010 | Turncliff et al. |
| 2011/0136848 | A1 | 6/2011 | Silverman |
| 2012/0010412 | A1 | 1/2012 | Duncan |
| 2013/0231361 | A1 | 9/2013 | Wentland |
| 2013/0281388 | A1 | 10/2013 | Deaver |

FOREIGN PATENT DOCUMENTS

| | | |
|---|---|---|
| EP | 1 359 146 B1 | 4/2008 |
| ES | 2 121 553 B1 | 6/1999 |
| GB | 0 874 217 A | 8/1961 |
| GB | 1 340 720 A | 12/1973 |
| JP | 40010154 B4 | 5/1965 |
| WO | 93/11761 A1 | 6/1993 |
| WO | 97/25331 A1 | 7/1997 |
| WO | 98/52929 A1 | 11/1998 |
| WO | 01/12197 A1 | 2/2001 |
| WO | 02/36573 A2 | 5/2002 |
| WO | 03/101963 A1 | 12/2003 |
| WO | 2004/005294 A2 | 1/2004 |
| WO | 2004/007449 A1 | 1/2004 |
| WO | 2004/045562 A2 | 6/2004 |
| WO | 2006/052710 A1 | 5/2006 |
| WO | 2006/096626 A2 | 9/2006 |
| WO | 2007/014137 A2 | 2/2007 |
| WO | 2007/089934 A2 | 8/2007 |
| WO | 2008/144394 A2 | 11/2008 |
| WO | 2009/023567 A1 | 2/2009 |
| WO | 2010/011619 A1 | 1/2010 |
| WO | 2010/107457 A1 | 9/2010 |
| WO | 2010/141666 A2 | 9/2010 |
| WO | 2011/119605 A2 | 9/2011 |
| WO | 2012/088494 A1 | 6/2012 |
| WO | 2014/190270 A1 | 11/2014 |
| WO | 2014/190271 A2 | 11/2014 |

OTHER PUBLICATIONS

Cacchi et al., "Palladium-Catalyzed Carbonylation of Aryl Triflates," Tetrahedron Ltrs., 27, pp. 3931-3934 (1986).
Alkermes "Alkermes Initiates Clinical Study of ALKS 5461 for Treatment-Resistant Depression," Alkermes, Inc. Retrieved from the internet: URL: http://www.pipelinereview.com/index.php/2011061543020/Small-Molecules/Alkermes-Initiates-Clinical-Study-of-ALKS-5461-for-Treatment-Resistant-Depression.html. [Last Accessed Jun. 2011].
Alkermes "Strong Results for Alkermes' ALKS 5461 in Major Depressive Disorder," Alkermes, Inc. Retrieved from the internet: URL: http://www.thepharmalettercom/file/109997/strong-results-for-alkermes-alks-5461-in-major-depressive-disorder.html. [Last Accessed Jun. 2011].
Belluzzi et al. (1977) "Enkephalin May Mediate Euphoria and Drive-Reduction Reward," Nature. 266:556-558.

Berge et al. (1977) "Pharmaceutical Salts," Journal of Pharmaceutical Sciences. 66(1):1-19.
Bianchetti et al. (1983) "Quaternary Derivatives of Narcotic Antagonists: Stereochemical Requirements at the Chiral Nitrogen for in vitro and in vivo Activity," Life Sciences. 33(Suppl 1):415-418.
Bianchi et al. (1982) "Quaternary Narcotic Antagonists' Relative Ability to Prevent Antinociception and Gastrointestinal Transit Inhibition in Morphine-Treated Rats as an Index of Peripheral Selectivity," Life Sciences. 30 (22):1875-1883.
Bidlack et al. (2002) "8-Carboxamidocyclazocine: a long-acting, novel benzomorphan," J. Pharmacol. Exp. Ther. 302 (1):374-380.
Cao et al. (2006) "Why is it Challenging to Predict Intestinal Drug Absorption and Oral Bioavailability in Human Using Rat Model," Pharmaceutical Research. 23(8):1675-1686.
Coop et al. (1999) "6 Opioid Affinity and Selectivity of 4-Hydroxy-3-methoxyindolomorphinan Analogues Related to Naltrindole," J. Med. Chem. 42:1673-1679.
Coop et al. (1999) "Direct and Simple Conversion of Codeine to Thebainon-A and Dihydrothebainone," Heterocycles. 50(1):39-42.
Danso-Danquah et al. (1995) "Synthesis and sigma-Binding Properties of 1'- and 3'-Halo- and 1',3'-Dihalo-N-normetazocine Analogs," J. Med. Chem. 38:2986-2989.
Darwin et al. (1980) "Fluorescence Properties of Pseudomorphine and Congeners: Structure-Activity Relationships," Journal of Pharmaceutical Sciences. 69:253-257.
Davies et al. (2001) "Palladium Catalysed Elaboration of Codeine and Morphine," J. Chem. Soc. Perkin Trans. 1:1413-1420.
Diaz et al. (2005) "SAR & Biological Evaluation of Novel trans-3,4-dimethyl-4-arylpiperidine Derivatives as Opioid Antagonists," Bioorganic & Medicinal Chemistry Letters. 15:3844-3848.
Elman et al. (2006) "Food Intake and Reward Mechanisms in Patients with Schizophrenia: Implications for Metabolic Disturbances and Treatment with Second-Generation Antipsychotic Agents," Neuropsychopharmacology. 31:2091-2120.
Garriock et al. (2010) "Association of Mu-Opioid Receptor Variants and Response to Citalopram Treatment in Major Depressive Disorder," Am. J. Psychiatry. 167(5):565-573.
Gross-Isseroff et al. (1990) "Regionally Selective Increases in p Opioid Receptor Density in the Brains of Suicide Victims," Brain Research. 530:312-316.
Heiner et al. (1995) "Efficient kg-Scale Synthesis of Thrombin Inhibitor CRC 220," Tetrahedron. 51(44):12047-12068.
Huidobro-Toro et al. (1981) "Comparative Study on The Effect of Morphine and the Opioid-Like Peptides in the Vas Deferens of Rodents: Species and Strain Differences, Evidence for Multiple Opiate Receptors," Life Sciences. 28:1331-1336.
Ida (1997) "The Nonnarcotic Antitussive Drug Dimemorfan: A Review," Clinical Therapeutics. 19(2):215-231.
International Search Report with Written Opinion corresponding to International Patent Application No. PCT/US2014/039359, mailed Sep. 22, 2014.
Kennedy et al. (2006) "Dysregulation of Endogenous Opioid Emotion Regulation Circuitry in Major Depression in Women," Arch. Gen Psychiatry 63, pp. 1199-1208 (Nov. 2006).
Ko et al. (1998) "Differentiation of kappa opioid agonist-induced antinociception by naltrexone apparent pA2 analysis in rhesus monkeys," J. Pharmacol. Exp. Ther. 285(2):518-526.
Kubota et al. (1998) "Palladium-Catalyzed Cyanation of Hindered, Electron-Rich Aryl Triflates by Zinc Cyanide," Tetrahedron Lett. 39:2907-2910.
Kubota et al. (1998) "Synthesis and Biological Activity of 3-Substituted 3-Desoxynaltrindole Derivatives," Bioorg. Med. Chem. Lett. 8:799-804.
McUrdy et al. (2000) "Investigation of Phenolic Bioisosterism in Opiates: 3-Sulfonamido Analogues of Naltrexone and Oxymorphone," Organic Letters. 2(6):819-821.
Mohacsi et al. (1985) "Acylmorphinans. A Novel Class of Potent Analgesic Agents," J. Med. Chem. 28(9):1177-1180.
Morera et al. (1998) "A Palladium-Catalyzed Carbonylative Route to Primary Amides," Tetrahedron Lett. 39:2835-2838.
Nan et al. (1997) "Synthesis of 2'-amino-17-cyclopropylmethyl-6,7-dehydro-3,14-dihydroxy-4,5α-epoxy-6,7:4',5'-thiazolomorphinan from naltrexone," J. Heterocyclic Chem. 34:1195-1203.

(56) References Cited

OTHER PUBLICATIONS

Neumeyer et al. (2003) "Design and Synthesis of Novel Dimeric Morphinan Ligands for K and p Opioid Receptors," J. Med. Chem. 46:5162-5170.

Rennison et al. (2006) "Structural Determinants of Opioid Activity in Derivatives of 14-Aminomorphinones: Effects of Changes to the Chain Linking of the C14-Amino Group to the Aryl Ring," Journal of Medicinal Chemistry. 49 (20):6104-6110.

Saal (2010) "Pharmaceutical Salts Optimization of Solubility or Even More?," American Pharmaceutical Review. Accessible on the Internet at URL: http://www_americanpharmaceuticalreview.com. pp. 1-6.

Sayre et al. (1984) "Design and Synthesis of Naltrexone-Derived Affinity Labels with Nonequilibrium Opioid Agonist and Antagonist Activities. Evidence for the Existence of Different p Receptor Subtypes in Different Tissues," J. Medicinal Chemistry. 27: 1325-1335.

Schultz et al. (2001) "Opioids and cardioprotection." Pharmacology & Therapeutics. 89:123-137.

Simpkins et al. (1991) "Evaluation of the Sites of Opioid Influence on Anterior Pituitary Hormone Secretion Using a Quaternary Opiate Antagonist," Neuroendocrinology. 54(4):384-390.

Todtenkopf et al. (Nov. 2008) "In vivo Characterization of Novel, Peripherally-Acting Opioid Antagonists," Society for Neuroscience Abstract Viewer and Itinerary Planner. vol. 38. In; The 38th Annual Meeting of the Society for Neuroscience, Nov. 2008.

Vanalstine (2007) "Design, Synthesis and Evalulation of Novel N-substituted Derivatives of 8-Carboxamidocyclazocine," Thesis (Ph.D.)—Rensselaer Polytechnic Institute, Apr. 2007, pp. 1-215.

Vanalstine et al. (2007) "Redefining the Structure-Activity Relationships of 2,6-methano-3-benzazocines.5. Opioid Receptor Binding Properties of [N-(4'-phenyl)-phenethyl) Analogues of 8-CAC," Bioorganic & Medicinal Chemistry Letters. 17(23):6516-6520.

Wentland et al. (2000) "8-Aminocyclazocine Analogues: Synthesis and Structure-Activity Relationships," Bioorg. Med. Chem. Lett. 10(2):183-187.

Wentland et al. (2000) "Selective Protection and Functionalization of Morphine: Synthesis and Opioid Receptor Binding Properties of 3-Amino 3-desoxymorphine Derivatives," J. Med. Chem. 43:3558-3565.

Wentland et al. (2001) "8-Carboxamidocyclazocine Analogues: Redefining the Structure-Activity Relationships of 2,6 Methano-3-benzazocines," Bioorg. Med. Chem. Lett. 11(5):623-626.

Wentland et al. (2001) "3-Carboxamido Analogues of Morphine and Naltrexone: Synthesis and Opioid Receptor Binding Properties," Bioorg. Med. Chem. Lett. 11(13):1717-1721.

Wentland et al. (2003) "Redefining the structure-activity relationships of 2,6-methano-3-benzazocines. Part 2: 8-formamidocyclazocine analogues," Bioorg. Med. Chem. Lett. 13(11):1911-1914.

Wentland et al. (2003) "Syntheses and Opioid Receptor Binding Affinities of 8-Amino-2,6-methano-3-benzazocines," Journal of Medicinal Chemistry. 46(5):838-849.

Wentland et al. (2005) "Redefining the Structure-Activity Relationships of 2,6-methano-3-benzazocines. Part 3: 8Thiocarboxamido and 8-thioformamido Derivatives of Cyclazocine," Bioorg. Med. Chem. Lett. 15(10):2547-2551.

Wentland et al. (2005) "Synthesis and Opioid Receptor Binding Properties of Highly Potent 4-hydroxy Analogue of Naltrexone," Bioorg. Med. Chem. Lett. 15(8):2107-2110.

Wentland et al. (2006) "Redefining the Structure-Activity Relationships of 2,6-methano-3-benzazocines, Part 4. Opioid Receptor Binding Properties of 8-[N-(4'-phenyl)-phenethyl) carboxamidol] Analogues of Cyclazocine and Ethylketocyclazocine," Journal of Medicinal Chemistry. 49(18):5635-5639.

Wentland et al. (2008) "Redefining the Structure-Activity Relationships of 2,6-methano-3-benzazocines, Part 6: Opioid Receptor Binding Properties of Cyclic Variants of 8-carboxamidocyclazocine," Bioogranic & Medicinal Chemistry. 16(10):5653-5664.

Wentland et al. (2009) "Redefining the Structure-Activity Relationships of 2,6-methano-3-benzazocines, Part 7: Syntheses and Opioid Receptor Properties of Cyclic Variants of Cyclazocine," Bioorgranic & Medicinal Chemistry Letters. 19(2):365-368.

Wentland et al. (2009) "Syntheses of novel high affinity ligands for opioid receptors," Bioorg. Med. Chem. Lett. 19 (8):2289-2294.

International Preliminary Report on Patentability for International Patent Application No. PCT/US2014/039359, mailed Nov. 24, 2015, 11 pages.

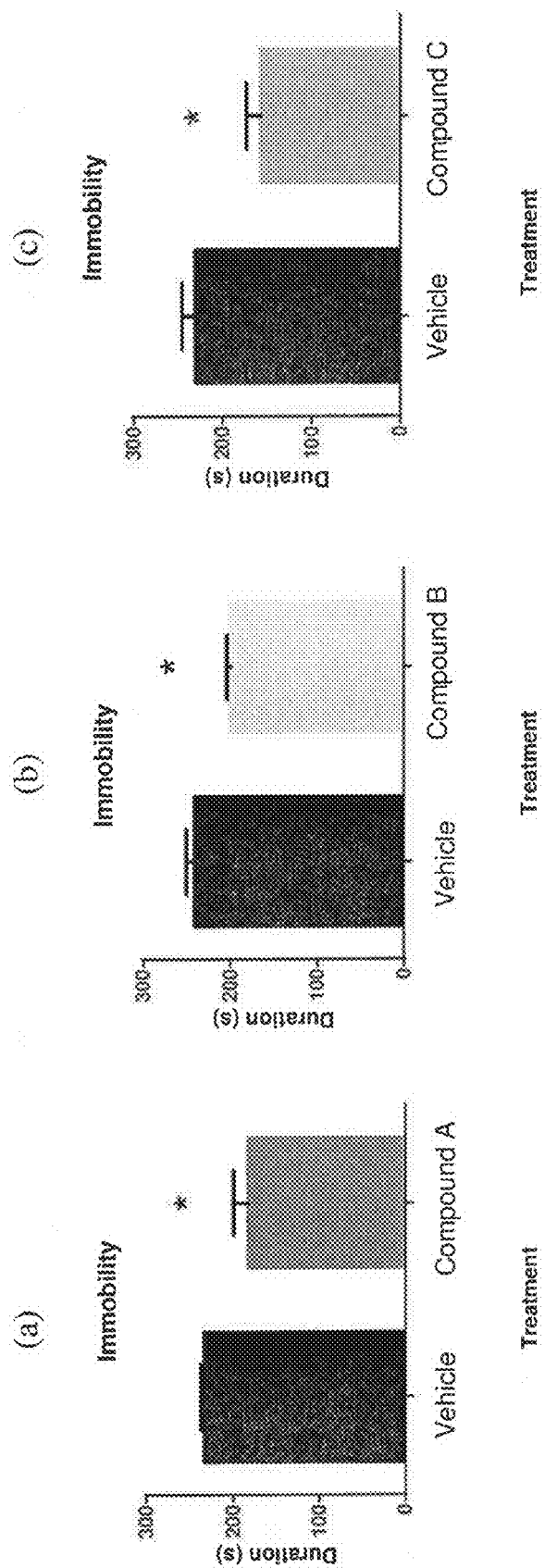

MORPHAN AND MORPHINAN ANALOGUES, AND METHODS OF USE

RELATED APPLICATIONS

This application is a Divisional of U.S. application Ser. No. 14/286,456, filed May 23, 2014, which claims priority to U.S. Provisional Patent Application Ser. No. 61/827,210, filed May 24, 2013, the entire contents of which are incorporated herein by reference in their entirety.

BACKGROUND

Depression (also known as depressive disorders or depressive symptoms) includes common but serious disorders of the brain characterized by combinations of signs and symptoms that may include feelings of hopelessness, guilt, worthlessness, and/or sadness alongside changes in sleep and/or eating patterns. While complex depressive disorders are thought to be caused by multiple factors, it is widely accepted that these disorders generally have a neurochemical component. Current treatment regimens often consist of a combination of psychotherapy and one or more medications to regulate neurotransmitters such as dopamine, serotonin and norepinephrine.

Current pharmacological methods of treatment for depressive disorders can be efficacious, but they often have significant drawbacks. Many anti-depressants have a latency period of two to three weeks, a delay that can be life-threatening to a patient who is depressed. After this initial period, if a chosen therapeutic shows little or no effect on the symptoms of the patient, the treating physician may alter the therapeutic regimen by increasing the dosage of the chosen drug or by recommending an entirely new compound. Even after a medication proves efficacious, the patient may suffer side effects such as dizziness, weight gain, and a loss of libido. The patient may also develop a tolerance to the drug, leading them to take ever-increasing doses in order to achieve similar results. In certain cases, chemical dependence may also develop, leading to potential abuse and, in the case of abrupt discontinuation, major withdrawal (including the risk of grand mal seizures and death).

While certain treatments for depressive disorders do exist, many commonly used therapeutics suffer from significant drawbacks including inefficacy, latency periods, tolerance, and chemical dependence. There is therefore an urgent need for new and improved methods of treatment for these disorders that may be used alone or in conjunction with existing therapeutic modalities.

SUMMARY OF THE INVENTION

Provided herein are morphan and morphinan analogues, pharmaceutical compositions thereof, and methods of using such compounds to treat or alleviate a disease or condition. Such diseases include, for example, a depressive symptom, pain, pruritis, diarrhea, irritable bowel syndrome, gastrointestinal motility disorder, obesity, respiratory depression, convulsions, coughing, hyperalgesia, and drug addiction.

In one aspect, provided herein is compound of Formula I:

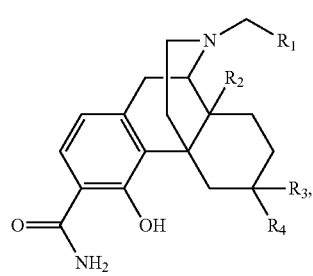

or a pharmaceutically acceptable salt thereof, wherein:

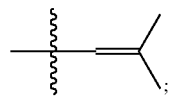 [SMILES: *C=C(C)C]

$R_1$ is cyclobutyl or
$R_2$ is H or methoxy; and
$R_3$ and $R_4$ are each, independently, H, hydroxyl, or $NR_5R_6$ wherein $R_5$ and $R_6$ are each independently H, alkyl, or substituted acyl, or alternatively, $R_3$ and $R_4$, together with the carbon atom to which they are attached, form C=O or C=CH$_2$.

In one embodiment of Formula I, $R_1$ is cyclobutyl. In another embodiment, $R_2$ is H. In still another embodiment, $R_3$ or $R_4$, but not both, is hydroxyl, or alternatively, $R_3$ and $R_4$, together with the carbon atom to which they are attached, form C=O.

In another aspect, provided herein is a compound of Formula II:

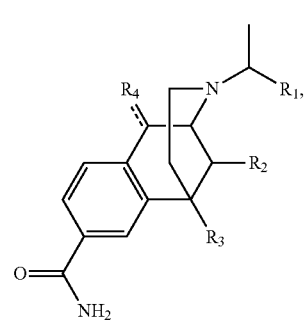

or a pharmaceutically acceptable salt thereof, wherein:
$R_1$ is $C_1$-$C_6$ alkyl, $C_2$-$C_6$ alkenyl, cycloalkyl, heterocyclyl, hydroxyalkyl, or alkoxyalkyl;
$R_2$ and $R_3$ are each $C_1$-$C_4$ alkyl, or alternatively, $R_2$ and $R_3$, together with the carbon atoms to which they are attached, form a 6-membered carbocyclic ring which is optionally substituted with a ketone, a hydroxyl, or a $NR_5R_6$ group wherein $R_5$ and $R_6$ are each independently H, alkyl, or substituted acyl group;
when ====== is a single bond, $R_4$ is H; and
when ====== is a double bond, $R_4$ is O.

In one embodiment of Formula II, $R_1$ is $C_2$-$C_6$ alkenyl or cycloalkyl. In another embodiment, $R_2$ and $R_3$ are each methyl. In still another embodiment, ====== is a single bond, and $R_4$ is H.

In still another aspect, provided herein is a compound of Formula III:

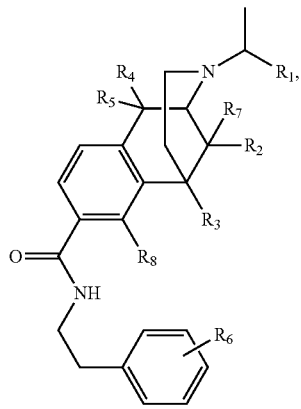

(III)

or a pharmaceutically acceptable salt thereof, wherein:

$R_1$ is $C_1$-$C_6$ alkyl, $C_2$-$C_6$ alkenyl, cycloalkyl, heterocyclyl, hydroxyalkyl, or alkoxyalkyl; $R_2$ and $R_3$ are each H or $C_1$-$C_4$ alkyl, or alternatively, $R_2$ and $R_3$, together with the carbon atoms to which they are attached, form a 6-membered unsubstituted carbocyclic ring, or a 6-membered carbocyclic ring optionally substituted with a hydroxyl, a ketone, or a $NR_{50}R_{60}$ group, wherein $R_{50}$ and $R_{60}$ are each independently H, alkyl, or substituted acyl;

$R_4$ and $R_5$ are each, independently, H, hydroxyl, or taken together with the carbon atom to which they are attach to, form a C=O group;

$R_6$ is unsubstituted or substituted $C_6$-$C_{10}$ aryl, or substituted or unsubstituted heteroaryl comprising one or two 5- or 6-membered rings and 1-4 heteroatoms selected from N, O and S; and $R_7$ and $R_8$ are each, independently, H or hydroxyl.

In one embodiment of Formula III, $R_1$ is $C_2$-$C_6$ alkenyl or cycloalkyl. In another embodiment, $R_2$ and $R_3$, together with the carbon atoms to which they are attached, form a 6-membered unsubstituted carbocyclic ring or a 6-membered carbocyclic ring substituted with a hydroxyl or a ketone. In still another embodiment, $R_4$ and $R_5$, taken together with the carbon atom to which they are attach to, form a C=O group. In yet another embodiment, $R_6$ is substituted heteroaryl comprising one or two 5- or 6-membered rings and 1-4 heteroatoms selected from N, O and S.

In still another aspect, provided herein is a compound of Formula IV:

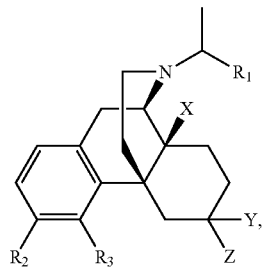

(IV)

or a pharmaceutically acceptable salt thereof, wherein:

$R_1$ is cyclopropyl or cyclobutyl;

X is H, hydroxyl, or methoxy;

Y and Z are each, independently, H, hydroxyl, or $NR_5R_6$ wherein $R_5$ and $R_6$ are each independently H, alkyl or substituted acyl, or alternatively, Y and Z, together with the carbon atom to which they are attached, form C=O or C=CH$_2$;

$R_3$ is H or hydroxyl; and $R_2$ is —C(O)NH$_2$, or —NH—CH$_2$-phenyl, wherein the phenyl can be substituted.

In one embodiment of Formula IV, $R_1$ is cyclopropyl. In another embodiment, X is H or hydroxyl. In still another embodiment, Y and Z are each, independently, H or hydroxyl, or alternatively, Y and Z, together with the carbon atom to which they are attached, form C=O. In yet another embodiment, $R_2$ is —C(O)NH$_2$.

In another embodiment, provided herein is a compound selected from the group consisting of:

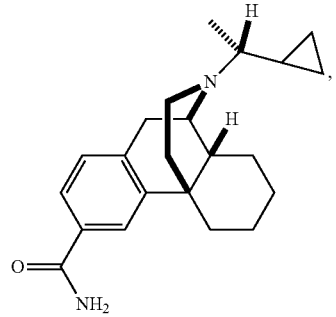

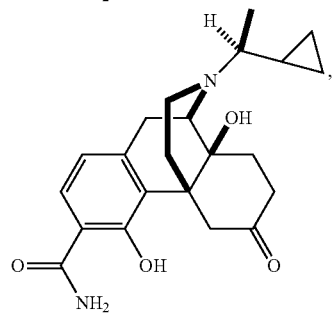

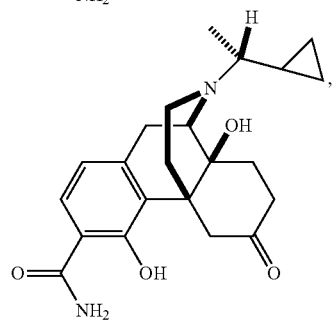

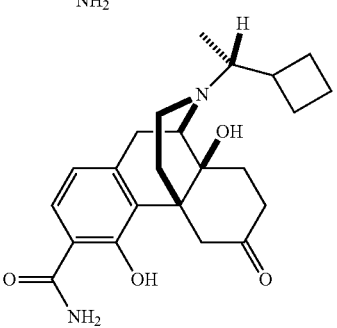

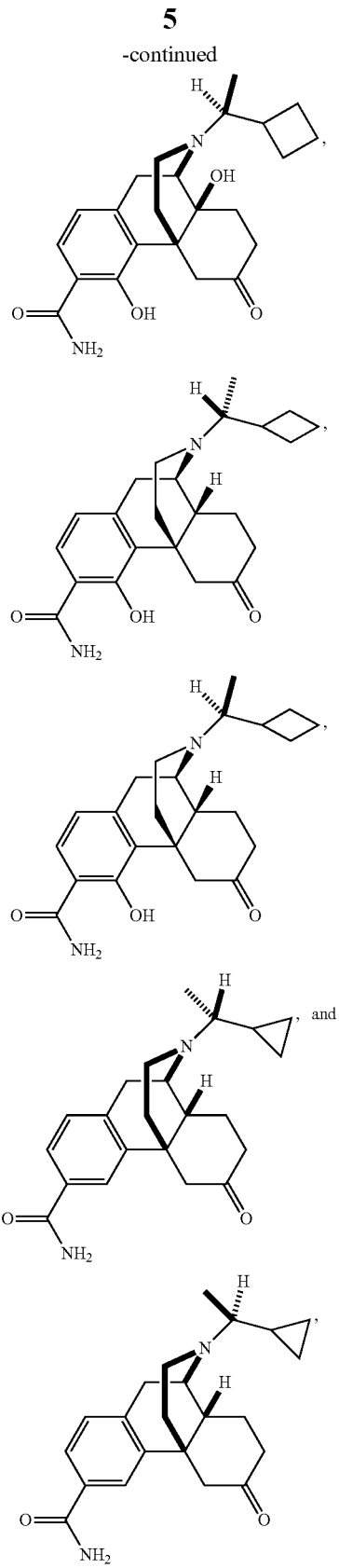

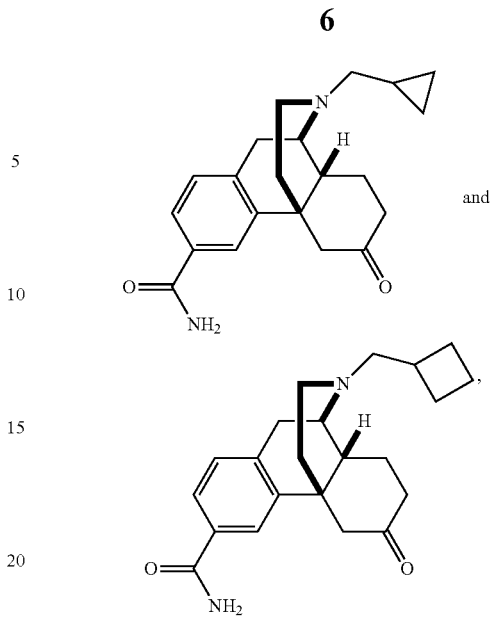

or a pharmaceutically acceptable salt thereof.

In one particular aspect, provided herein is a compound selected from or a pharmaceutically acceptable salt thereof.

In certain embodiments of the above-described aspects, the compound is a μ opioid receptor agonist having an Emax of 5% to 45% in a GTPγS binding assay. In particular embodiments, the Emax is 15% to 35% in a GTPγS binding assay. In other embodiments, the agonist has a low risk of opioid dependence, opioid addiction, and/or symptoms of opioid withdrawal.

In certain embodiments of the above-described aspects, the compound exhibits a maximal dopamine efflux in the nucleus accumbens of 125% to 300% over baseline in a rat. In particular embodiments, the compound exhibits a maximal dopamine efflux in the nucleus accumbens of 200% to 300% over baseline in a rat.

In other embodiments of the above-described aspects, the compound does not attenuate thermal pain in a rodent hot plate model when administered at a dose of at least 1 mg/kg. In particular embodiments, the compound does not attenuate thermal pain in a rodent hot plate model when administered at a dose of at least 3 mg/kg. In other embodiments, the compound does not attenuate thermal pain in a rodent hot plate model when administered at a dose of 10 mg/kg.

In another aspect, provided herein is a pharmaceutical composition comprising a pharmaceutically acceptable carrier and the compound of the above-described aspects.

In still another aspect, provided herein is a method of treating a depressive symptom in a subject in need thereof, wherein the method comprises administering to the subject an effective amount of a μ opioid receptor agonist that exhibits an Emax of 5% to 45% in a GTPγS binding assay. In particular embodiments, the Emax is 15% to 35% in a GTPγS binding assay. In other embodiment, said agonist has a low risk of opioid dependence, opioid addiction, and/or symptoms of opioid withdrawal.

In another aspect, provided herein is a method of treating a depressive symptom in a subject in need thereof, wherein the method comprises administering to the subject an effective amount of a compound having a maximal dopamine efflux in the nucleus accumbens of 125% to 300% over base line in a rat. In particular embodiments, the compound has a maximal dopamine efflux in the nucleus accumbens of 200% to 300% over base line in a rat.

In still another aspect, provided herein is a method of treating a depressive symptom in a subject in need thereof, wherein the method comprises administering to the subject an effective amount of a compound that does not attenuate thermal pain in a rodent hot plate model when administered at a dose of at least 1 mg/kg. In particular embodiments, the compound does not attenuate thermal pain in a rodent hot plate model when administered at a dose of at least 3 mg/kg. In other embodiments, the compound does not attenuate thermal pain in a rodent hot plate model when administered at a dose of 10 mg/kg.

In yet another aspect, provided herein is a method of treating a depressive symptom in a subject in need thereof, wherein the method comprises administering to the subject any one of the compounds provided herein, or a pharmaceutically acceptable salt thereof.

In certain embodiments of the methods provided herein, the depressive symptom is depressed mood, loss of pleasure, loss of appetite, sleep disturbance, psychomotor changes, fatigue, and/or post-partum depression.

In other embodiments, the depressive symptom is associated with a mental condition, wherein the mental condition is schizoaffective disorder, and/or seasonal affective disorder.

In still other embodiments, the depressive symptom is acute stress disorder, adjustment disorders with depressed mood, Asperger syndrome, attention deficit, bereavement, bipolar I disorder, bipolar II disorder, borderline and personality disorder, cyclothymia and dysthymia, depression such as major depressive disorder (MDD) and treatment-resistant disorder (TRD), Dysthymic disorder, hyperactivity disorder, impulse control disorder, mixed mania, obsessive-compulsive personality disorder (OCD), paranoid, post-traumatic stress disorder, seasonal affective disorder, self-injury separation, sleep disorder, substance-induced mood disorder, Tourette syndrome and tic disorder, and/or Trichotillomania.

In yet other embodiments, the depressive symptom is an anxiety disorder, wherein the anxiety disorder is generalized anxiety disorder, panic, agoraphobia, acute stress, and/or post-traumatic stress disorder.

In certain embodiments, the depressive symptom is associated with chronic or recurrent depression.

Furthermore, provided herein is a method of treating a disease or condition associated with the group consisting of pain, pruritis, diarrhea, irritable bowel syndrome, gastrointestinal motility disorder, obesity, respiratory depression, convulsions, coughing, hyperalgesia, and drug addiction in a subject, which comprises administering to the subject a pharmaceutical composition comprising any one of the compounds disclosed herein or a pharmaceutically acceptable salt thereof. In one embodiment, the drug addiction is selected from heroin, cocaine, nicotine, amphetamine and alcohol addiction.

Also provided herein is a method of treating a disease or condition in a subject by altering a response mediated by an opioid receptor, wherein the method comprises bringing into contact with the opioid receptor an effective amount of any one of the compounds provided herein.

In preferred embodiments of all of the methods disclosed herein, the subject is a human.

BRIEF DESCRIPTION OF THE DRAWINGS

FIG. 9 depicts the results of in vivo Forced Swim Test measuring reduction of immobility in rats induced by different doses of Compound A, B or C.

DETAILED DESCRIPTION

Compounds of the Invention

Figure 1:
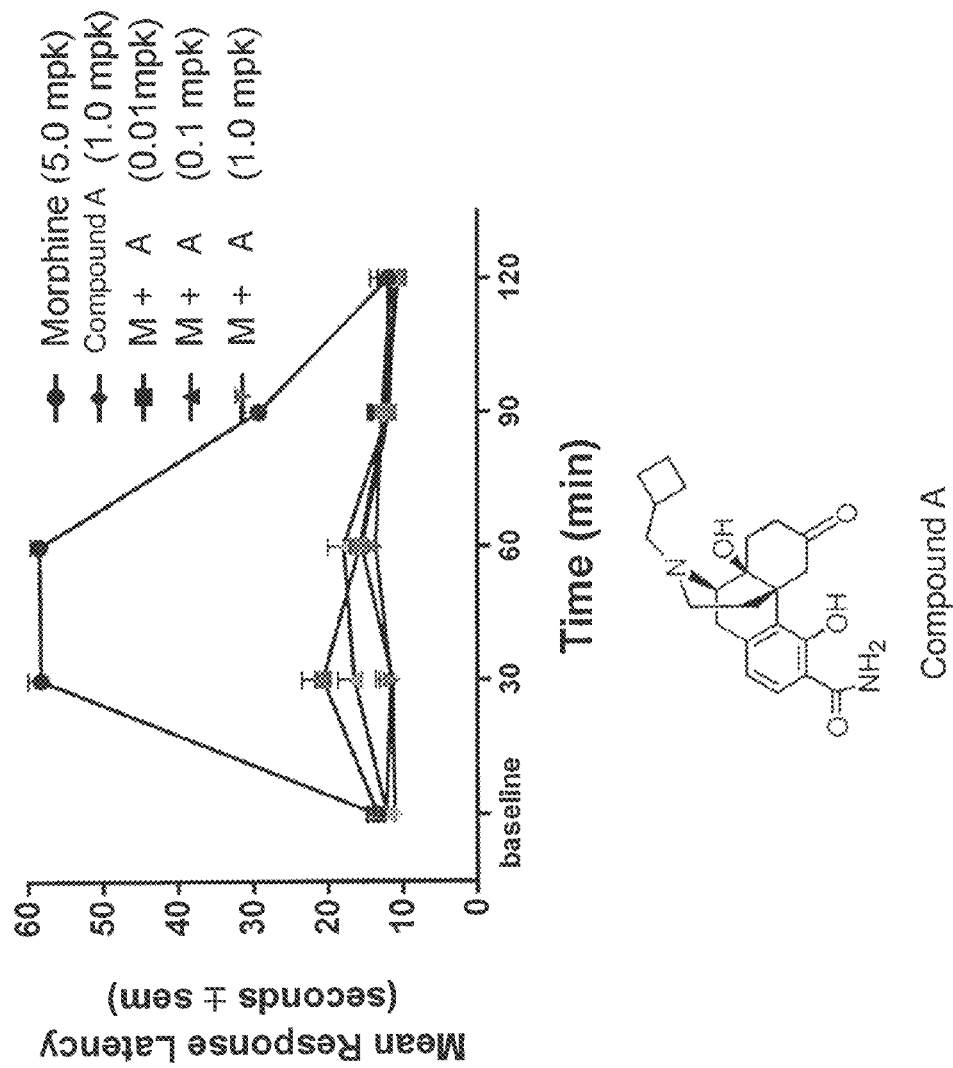
FIG. 1 depicts the results of experiments measuring the antinociceptive effects of Compound A, either alone or in combination with morphine, using a rat hot plate assay.

This disclosure is directed toward morphan and morphinan analogues, and pharmaceutical compositions thereof for use in treatment of a disease or condition. Provided herein are compounds and compositions thereof useful to treat a depressive symptom, such as depressed mood, loss of pleasure, loss of appetite, sleep disturbance, psychomotor changes, fatigue, and/or post-partum depression. Provided herein are also compounds and compositions thereof useful in treating pain, pruritis, diarrhea, irritable bowel syndrome, gastrointestinal motility disorder, obesity, to respiratory depression, convulsions, coughing, hyperalgesia, and/or drug addiction. In one particular embodiment, provided herein are compounds and compositions thereof useful to treat depression.

In one aspect, provided herein is a compound of the Formula I:

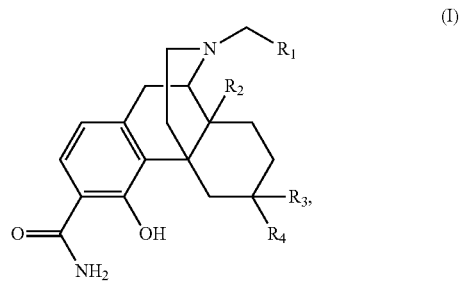

or a pharmaceutically acceptable salt thereof, wherein:

R$_1$ is cyclobutyl or

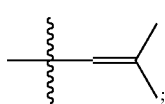 [SMILES: *C=C(C)C]

;

R$_2$ is H or methoxy; and

R$_3$ and R$_4$ are each, independently, H, hydroxyl, or NR$_5$R$_6$ wherein R$_5$ and R$_6$ are each independently H, alkyl, or substituted acyl, or alternatively, R$_3$ and R$_4$, together with the carbon atom to which they are attached, form C=O or C=CH$_2$.

In one embodiment of Formula I, substituted acyl is defined as follows:

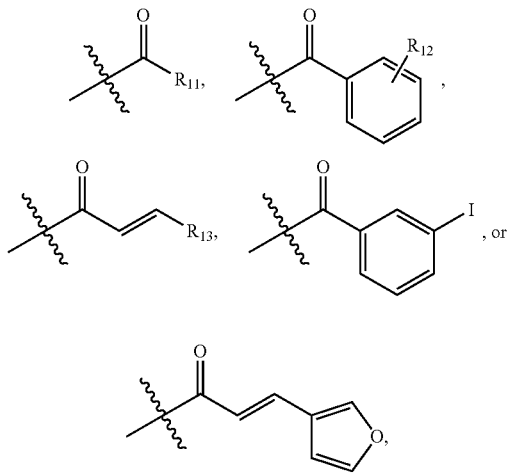

wherein R$_{11}$ is linear or branched C$_1$-C$_6$ alkyl; R$_{12}$ is halo, C$_1$-C$_6$ alkyl, or C$_1$-C$_6$ alkoxy; and R$_{13}$ is aryl or heteroaryl.

In another embodiment of Formula I, R$_1$ is cyclobutyl.

In another embodiment of Formula I, R$_2$ is methoxy. In another embodiment, R$_2$ is H.

In still another embodiment, R$_3$ or R$_4$, but not both, is hydroxyl, or alternatively, R$_3$ and R$_4$, together with the carbon atom to which they are attached, form C=O.

In another aspect, provided herein is a compound of Formula Ia:

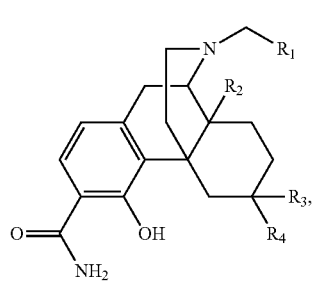

(Ia)

or a pharmaceutically acceptable salt thereof, wherein:

R$_1$ is cyclobutyl, cyclopentyl,

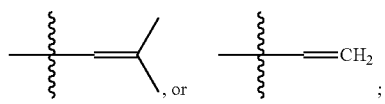

;

R$_2$ is H, hydroxyl, or methoxy; and

R$_3$ and R$_4$ are each, independently, H, hydroxyl, or NR$_5$R$_6$ wherein R$_5$ and R$_6$ are each independently H, alkyl, or substituted acyl, or alternatively, R$_3$ and R$_4$, together with the carbon atom to which they are attached, form C=O or C=CH$_2$.

In one embodiment of Formula Ia, R$_1$ is cyclobutyl,

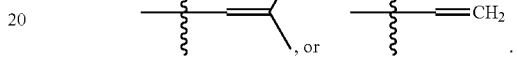

.

In one embodiment of Formula Ia, substituted acyl is defined as follows:

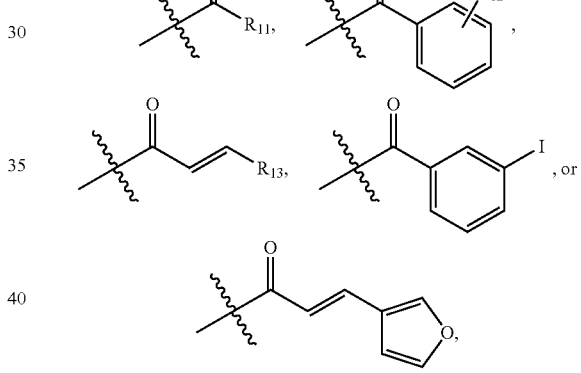

wherein R$_{11}$ is linear or branched C$_1$-C$_6$ alkyl; R$_{12}$ is halo, C$_1$-C$_6$ alkyl, or C$_1$-C$_6$ alkoxy; and R$_{13}$ is aryl or heteroaryl.

In one embodiment of Formula Ia, R$_1$ is cyclobutyl.

In another embodiment of Formula Ia, R$_2$ is H.

In still another embodiment of Formula Ia, R$_3$ or R$_4$, but not both, is hydroxyl, or alternatively, R$_3$ and R$_4$, together with the carbon atom to which they are attached, form C=O.

In one aspect, provided herein is a compound of the Formula Ib:

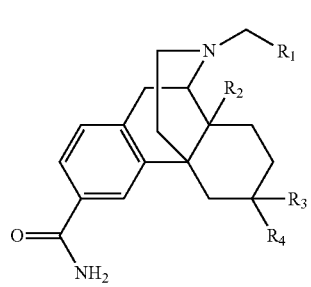

(Ib)

or a pharmaceutically acceptable salt thereof, wherein:
$R_1$ is cyclopropyl, cyclobutyl, cyclopentyl,

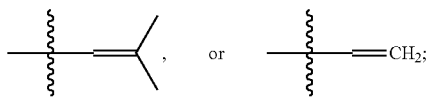

$R_2$ is H, hydroxyl, or methoxy; and
$R_3$ is H or hydroxyl, and
$R_4$ is hydroxyl, or $NR_5R_6$ wherein $R_5$ and $R_6$ are each independently H, alkyl, or substituted acyl;
or alternatively, $R_3$ and $R_4$, together with the carbon atom to which they are attached, form C=O or C=CH$_2$.

In one embodiment of Formula Ib, $R_1$ is cyclobutyl or

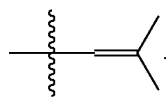 [SMILES: *C=C(C)C]

In one embodiment of Formula Ib, $R_1$ is cyclobutyl.
In another embodiment of Formula Ib, $R_2$ is methoxy. In another embodiment, $R_2$ is H.
In another embodiment of Formula Ib, substituted acyl is defined as follows:

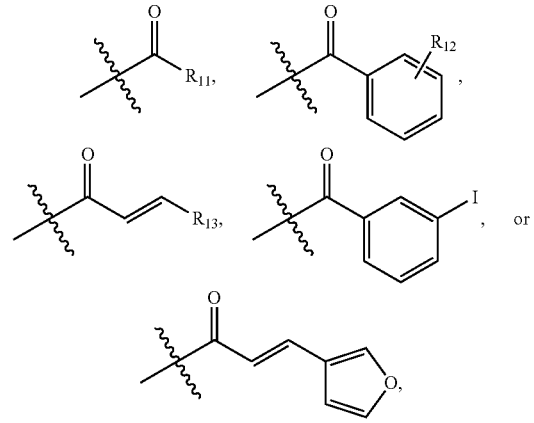

wherein $R_{11}$ is linear or branched $C_1$-$C_6$ alkyl; $R_{12}$ is halo, $C_1$-$C_6$ alkyl, or $C_1$-$C_6$ alkoxy; and $R_{13}$ is aryl or heteroaryl.

In still another embodiment, $R_3$ is H and $R_4$ is hydroxyl, or alternatively, $R_3$ and $R_4$, together with the carbon atom to which they are attached, form C=O or C=CH$_2$.

In another aspect, provided herein is a compound of Formula Ic:

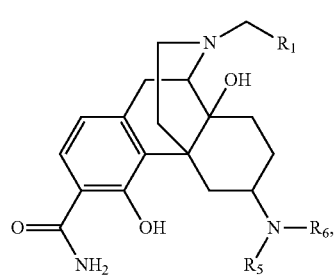

(Ic)

or a pharmaceutically acceptable salt thereof, wherein:
$R_1$ is cyclobutyl, cyclopentyl,

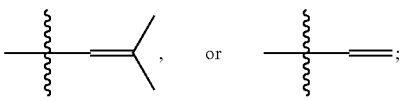

$R_5$ and $R_6$ are each independently H, alkyl, or substituted acyl, wherein the substituted acyl is:

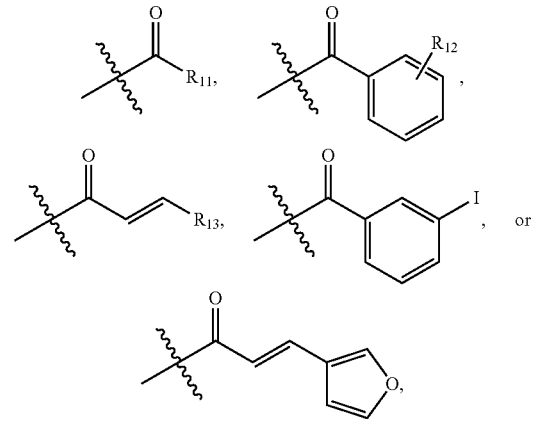

wherein $R_{11}$ is $C_1$-$C_6$ linear or branched alkyl; $R_{12}$ is H, halo, $C_1$-$C_6$ alkyl, or $C_1$-$C_6$ alkoxy; and $R_{13}$ is H, aryl, or heteroaryl.

In one embodiment of Formula Ic, $R_1$ is cyclobutyl. In another embodiment, $R_1$ is cyclopentyl.

In another aspect, provided herein is a compound of Formula II:

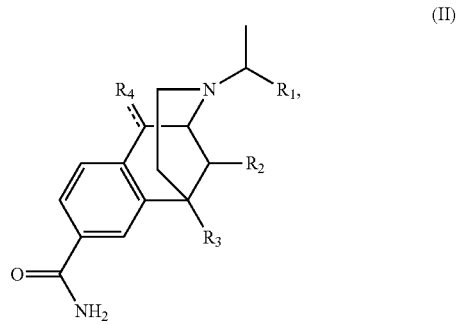

(II)

or a pharmaceutically acceptable salt thereof, wherein:
$R_1$ is $C_1$-$C_6$ alkyl, $C_2$-$C_6$ alkenyl, cycloalkyl, heterocyclyl, hydroxyalkyl, or alkoxyalkyl;
$R_2$ and $R_3$ are each $C_1$-$C_4$ alkyl, or alternatively, $R_2$ and $R_3$, together with the carbon atoms to which they are attached, form a 6-membered carbocyclic ring, wherein the carbocyclic ring is optionally substituted with a ketone, a hydroxyl, or a $NR_5R_6$ group wherein $R_5$ and $R_6$ are each independently H, alkyl, or substituted acyl;
when ====== is a single bond, $R_4$ is H; and
when ====== is a double bond, $R_4$ is O.

In one embodiment of Formula (II), $R_1$ is $C_2$-$C_6$ alkenyl or cycloalkyl. In a particular embodiment, $R_1$ can be cyclopropyl or cyclobutyl.

In another embodiment of Formula II, substituted acyl is defined as follows:

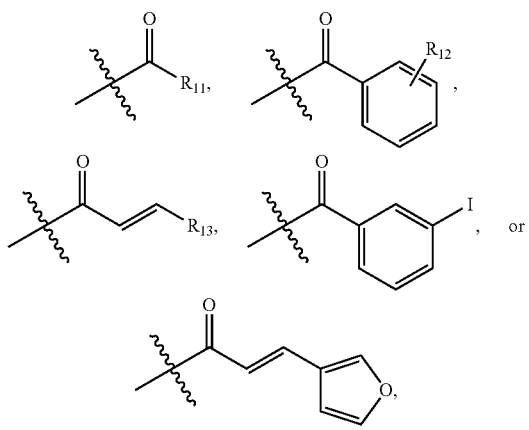

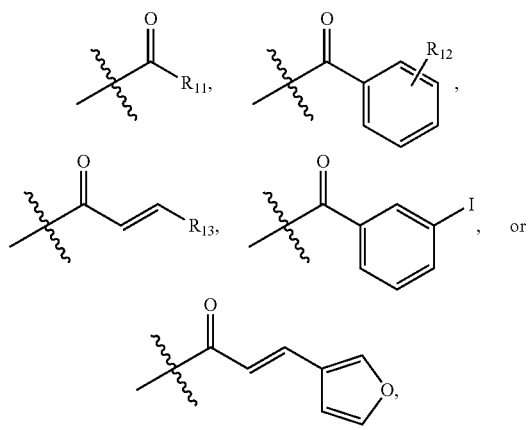

wherein $R_{11}$ is linear or branched $C_1$-$C_6$ alkyl; $R_{12}$ is halo, $C_1$-$C_6$ alkyl, or $C_1$-$C_6$ alkoxy; and $R_{13}$ is aryl or heteroaryl.

In another embodiment of Formula (II), $R_2$ and $R_3$ are each methyl.

In still another embodiment of Formula (II), ====== is a single bond, and $R_4$ is H.

In another aspect, provided herein is a compound of Formula IIa:

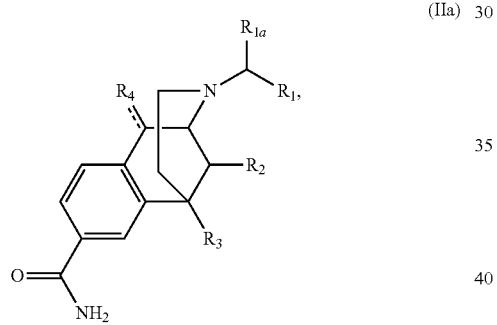

or a pharmaceutically acceptable salt thereof, wherein:

$R_1$ is $C_1$-$C_6$ alkyl, $C_2$-$C_6$ alkenyl, hydroxyalkyl, alkoxyalkyl, cyclobutyl, or cyclopentyl;

$R_{1a}$ is H or methyl;

$R_2$ and $R_3$ are each $C_1$-$C_4$ alkyl, or alternatively, $R_2$ and $R_3$, together with the carbon atoms to which they are attached, form a 6-membered carbocyclic ring, wherein the carbocyclic ring is substituted with a ketone, or a hydroxyl, or a $NR_5R_6$ group, wherein $R_5$ and $R_6$ are each independently H, alkyl or substituted acyl;

when ====== is a single bond, $R_4$ is H; and
when ====== is a double bond, $R_4$ is O.

In one embodiment of Formula (IIa), $R_1$ is cyclobutyl, cyclopentyl,

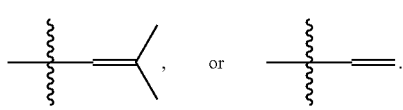

In one embodiment of Formula (IIa), substituted acyl is defined as follows:

wherein $R_{11}$ is linear or branched $C_1$-$C_6$ alkyl; $R_{12}$ is halo, $C_1$-$C_6$ alkyl, or $C_1$-$C_6$ alkoxy; and $R_{13}$ is aryl or heteroaryl.

In one embodiment of Formula (IIa), $R_1$ is cyclobutyl. In another embodiment, $R_1$ is cyclopentyl. In still another embodiment, $R_1$ is

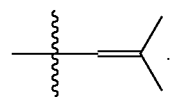

In one embodiment of Formula (IIa), $R_2$ and $R_3$ are each methyl. In another embodiment, $R_2$ and $R_3$, together with the carbon atoms to which they are attached, form a 6-membered carbocyclic ring, wherein the carbocyclic ring is substituted with a ketone, or a hydroxyl, or a $NR_5R_6$ group.

In another embodiment, $R_{1a}$ is H.

In still another embodiment of Formula (IIa), ====== is a single bond, and $R_4$ is H.

In yet another embodiment of Formula (IIa), ====== is a double bond, and $R_4$ is O.

In still another aspect, provided herein is a compound of Formula III:

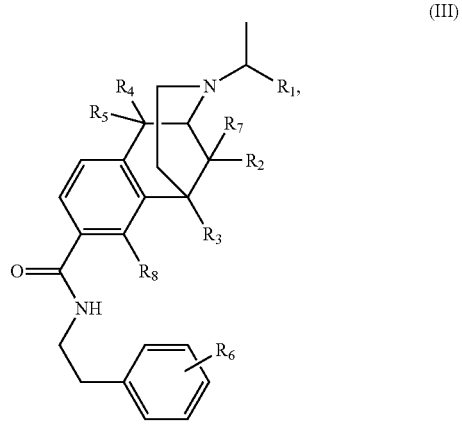

or a pharmaceutically acceptable salt thereof, wherein:

$R_1$ is $C_1$-$C_6$ alkyl, $C_2$-$C_6$ alkenyl, cycloalkyl, heterocyclyl, hydroxyalkyl, or alkoxyalkyl;

$R_2$ and $R_3$ are each H or $C_1$-$C_4$ alkyl, or alternatively, $R_2$ and $R_3$, together with the carbon atoms to which they are attached, form a 6-membered unsubstituted carbocyclic ring, or a 6-membered carbocyclic ring optionally substituted with a hydroxyl, a ketone, or a NR$_{50}$R$_{60}$ group, wherein R$_{50}$ and R$_{60}$ are each independently H, alkyl, or substituted acyl;

R$_4$ and R$_5$ are each, independently, H, hydroxyl, or taken together with the carbon atom to which they are attach to form a C═O group;

R$_6$ is unsubstituted or substituted C$_6$-C$_{10}$ aryl, or substituted or unsubstituted heteroaryl comprising one or two 5- or 6-membered rings and 1-4 heteroatoms selected from N, O and S; and R$_7$ and R$_8$ are each, independently, H or hydroxyl.

In one embodiment of Formula (III), R$_1$ is C$_2$-C$_6$ alkenyl or cycloalkyl. In a particular embodiment, R$_1$ can be cyclopropyl or cyclobutyl.

In another embodiment of Formula (III), R$_2$ and R$_3$ are each H, methyl or ethyl.

In another embodiment of Formula (III), R$_2$ and R$_3$, together with the carbon atoms to which they are attached, form a 6-membered unsubstituted carbocyclic ring or a 6-membered carbocyclic ring substituted with a hydroxyl or a ketone.

In another embodiment of Formula (III), substituted acyl is defined as follows:

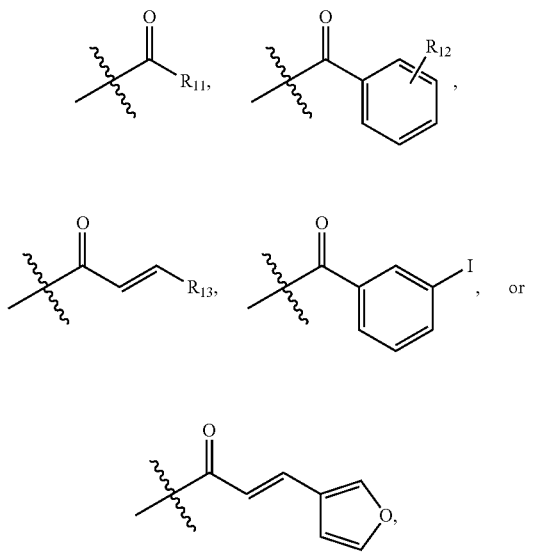

wherein R$_{11}$ is linear or branched C$_1$-C$_6$ alkyl; R$_{12}$ is halo, C$_1$-C$_6$ alkyl, or C$_1$-C$_6$ alkoxy; and R$_{13}$ is aryl or heteroaryl.

In another embodiment of Formula (III), R$_4$ and R$_5$, taken together with the carbon atom to which they are attached, form a C═O group.

In another embodiment of Formula (III), R$_4$ and R$_5$ are each, independently, H or hydroxyl.

In still another embodiment of Formula (III), R$_6$ is substituted heteroaryl comprising one or two 5- or 6-membered rings and 1-4 heteroatoms selected from N, O and S.

In yet another embodiment of Formula (III), R$_6$ is unsubstituted or substituted C$_6$-C$_{10}$ aryl.

In another aspect, provided herein is a compound of Formula IV:

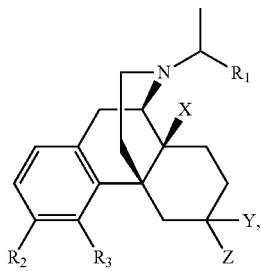

or a pharmaceutically acceptable salt thereof, wherein:

R$_1$ is cyclopropyl or cyclobutyl;

X is H, hydroxyl, or methoxy;

Y and Z are each, independently, H, hydroxyl, or NR$_5$R$_6$ wherein R$_5$ and R$_6$ are each independently H, alkyl or substituted acyl, or alternatively, Y and Z, together with the carbon atom to which they are attached, form C═O or C═CH$_2$;

R$_3$ is H or hydroxyl; and

R$_2$ is —C(O)NH$_2$, or —NH—CH$_2$-phenyl, wherein the phenyl can be substituted.

In one embodiment of Formula IV, substituted acyl is defined as follows:

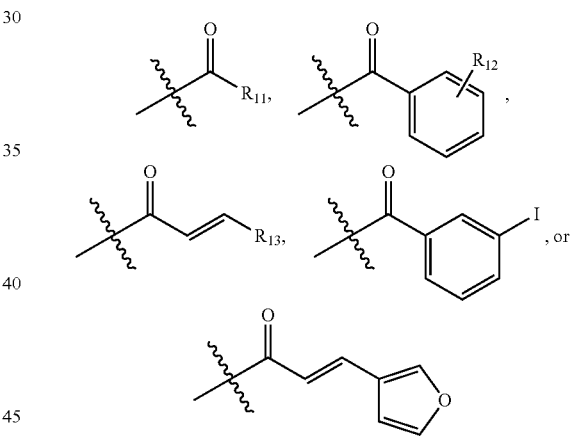

wherein R$_{11}$ is linear or branched C$_1$-C$_6$ alkyl; R$_{12}$ is halo, C$_1$-C$_6$ alkyl, or C$_1$-C$_6$ alkoxy; and R$_{13}$ is aryl or heteroaryl.

In one embodiment of Formula (IV), R$_1$ is cyclopropyl.

In another embodiment of Formula (IV), X is H or hydroxyl.

In still another embodiment of Formula (IV), Y and Z are each, independently, H or hydroxyl, or alternatively, Y and Z, together with the carbon atom to which they are attached, form C═O or C═CH$_2$.

In another embodiment of Formula (IV), R$_2$ is —NH—CH$_2$-phenyl, wherein the phenyl can be substituted. In a particular embodiment, the phenyl of —NH—CH$_2$— phenyl can have one to three substituents independently selected from the group consisting of hydroxyl, alkyl, and alkoxy.

In yet another embodiment of Formula (IV), R$_2$ is —C(O) NH$_2$.

In another aspect, provided herein is a compound of Formula IVa:

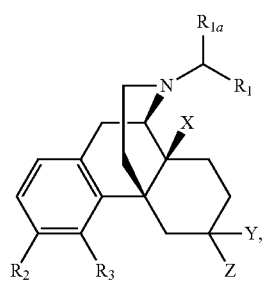

(IVa)

or a pharmaceutically acceptable salt thereof, wherein:

$R_1$ is $C_1$-$C_6$ alkyl, $C_2$-$C_6$ alkenyl, $C_3$ or $C_5$-$C_{10}$ cycloalkyl, heterocyclyl, hydroxyalkyl, or alkoxyalkyl;

$R_{1a}$ is H or methyl;

X is H, hydroxyl, or methoxy;

Y and Z are each, independently, H, hydroxyl, or $NR_5R_6$ wherein $R_5$ and $R_6$ are each independently H, alkyl or substituted acyl, or alternatively, Y and Z, together with the carbon atom to which they are attached, form C=O or C=CH$_2$;

$R_3$ is H or hydroxyl; and $R_2$ is —NH—CH$_2$-phenyl, wherein the phenyl can be further substituted.

In one embodiment of Formula (IVa), $R_1$ is cyclopropyl.

In one embodiment of Formula (Iva), substituted acyl is defined as follows:

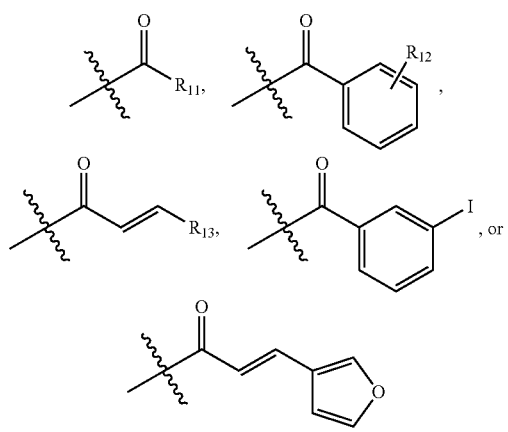

wherein $R_{11}$ is linear or branched $C_1$-$C_6$ alkyl; $R_{12}$ is halo, $C_1$-$C_6$ alkyl, or $C_1$-$C_6$ alkoxy; and $R_{13}$ is aryl or heteroaryl.

In another embodiment of Formula (IVa), X is H or hydroxyl.

In still another embodiment of Formula (IVa), Y and Z are both H, or alternatively, Y and Z, together with the carbon atom to which they are attached, form C=O or C=CH$_2$.

In another embodiment of Formula (Iva), Y is H, and Z is hydroxyl or $NR_5R_6$.

In another embodiment of Formula (IVa), the phenyl of —NH—CH$_2$-phenyl can have one to three substituents independently selected from the group consisting of hydroxyl, alkyl, and alkoxy.

In yet another embodiment of Formula (IVa), $R_{1a}$ is H.

In still another aspect, provided herein is a compound selected from

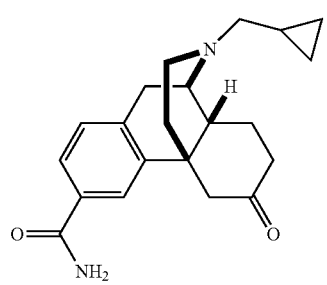

and

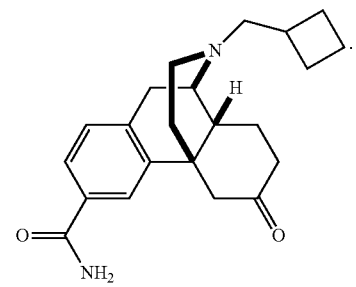

In yet another aspect, provided herein is a compound of Formula V

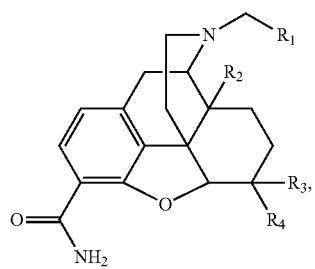

(V)

or a pharmaceutically acceptable salt thereof, wherein:

$R_1$ is cyclobutyl, cyclopropyl,

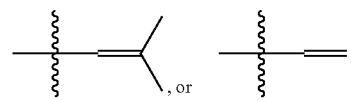

, or ;

$R_2$ is H, OH, or methoxy; and $R_3$ and $R_4$ are each, independently, H, hydroxyl or $NR_5R_6$ wherein $R_5$ and $R_6$ are each independently H, alkyl or substituted acyl, or alternatively, $R_3$ and $R_4$, together with the carbon atom to which they are attached, form C=O or C=CH$_2$.

In one embodiment of Formula V, substituted acyl is defined as follows:

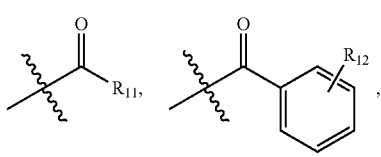

-continued

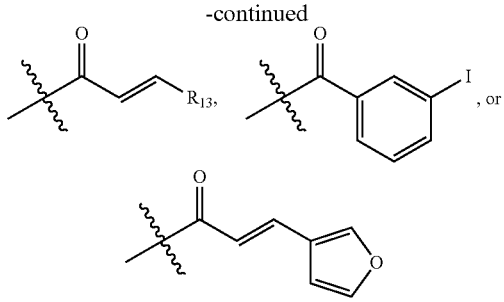

wherein $R_{11}$ is linear or branched $C_1$-$C_6$ alkyl; $R_{12}$ is halo, $C_1$-$C_6$ alkyl, or $C_1$-$C_6$ alkoxy; and $R_{13}$ is aryl or heteroaryl.

In one embodiment of Formula V, $R_3$ and $R_4$, together with the carbon atom to which they are attached, form C=O or C=CH$_2$.

In another embodiment of Formula V, $R_3$ is H, and $R_4$ is hydroxyl or $NR_5R_6$.

In one embodiment of Formula V, $R_3$ is H, and $R_4$ is hydroxyl.

In another embodiment, provided herein are the compounds shown in Table A, or pharmaceutically acceptable salts thereof.

TABLE A

Compound 1
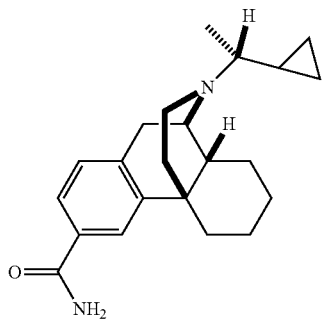

Compound 2
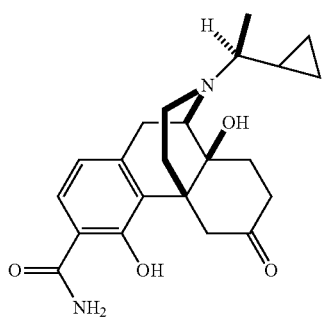

Compound 3
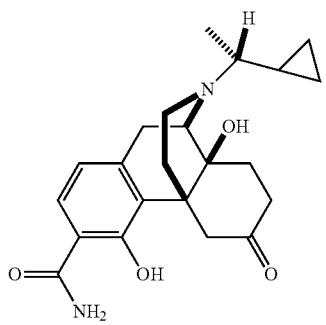

TABLE A-continued

Compound 4
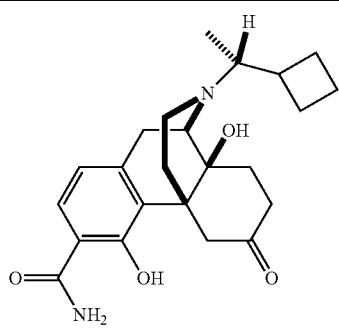

Compound 5
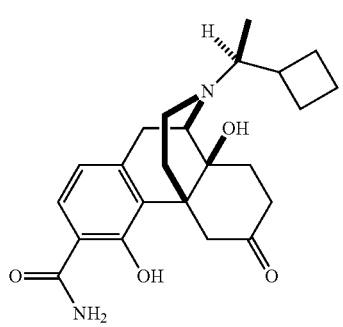

Compound 6
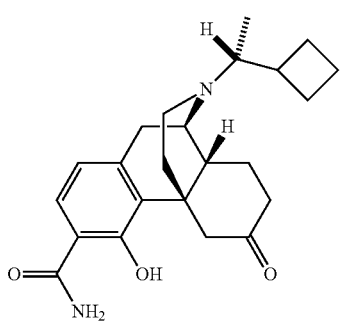 [SMILES: C[C@H](C1CCC1)N1CC[C@]23CC(=O)CC[C@H]2[C@H]1Cc1ccc(C(N)=O)c(O)c13]

Compound 7
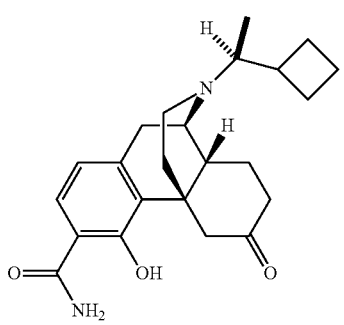 [SMILES: C[C@@H](C1CCC1)N1CC[C@]23CC(=O)CC[C@H]2[C@H]1Cc1ccc(C(N)=O)c(O)c13]

Compound 8
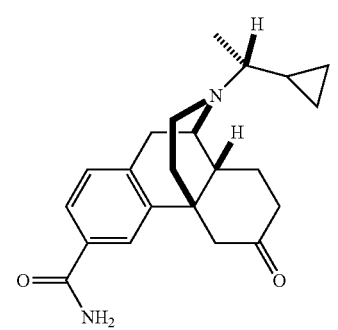

TABLE A-continued
Compound 9
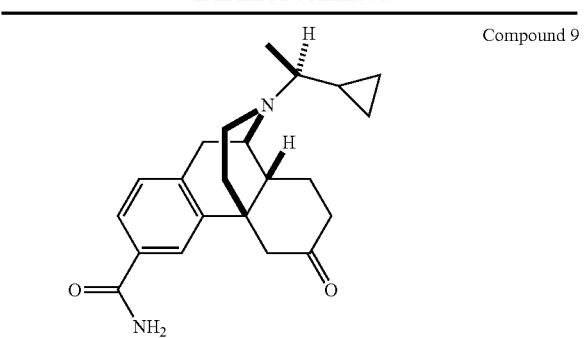
Compound 10
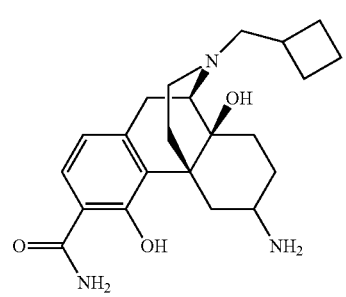 [SMILES: NC(=O)c1ccc2c(c1O)[C@]13CCN(CC4CCC4)[C@H](C2)[C@]1(O)CCC(N)C3]
Compound 11
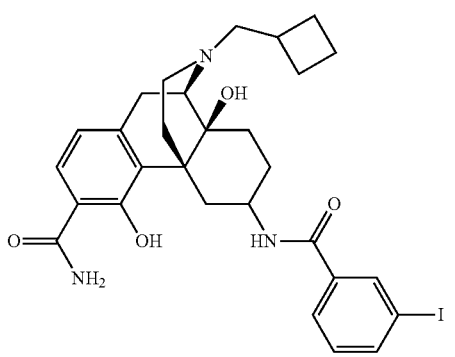 [SMILES: NC(=O)c1ccc2c(c1O)[C@]13CCN(CC4CCC4)[C@H](C2)[C@]1(O)CCC(NC(=O)c1cccc(I)c1)C3]
Compound 12
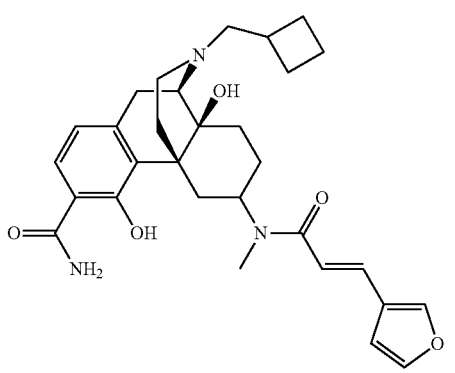 [SMILES: CN(C(=O)/C=C/c1ccoc1)C1CC[C@@]2(O)[C@H]3Cc4ccc(C(N)=O)c(O)c4[C@@]2(CCN3CC2CCC2)C1]
Compound 13
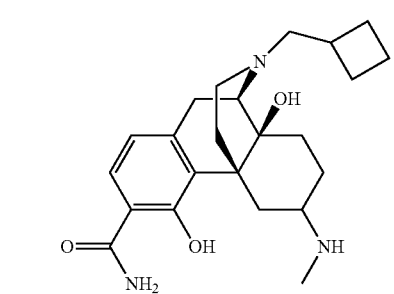 [SMILES: CNC1CC[C@@]2(O)[C@H]3Cc4ccc(C(N)=O)c(O)c4[C@@]2(CCN3CC2CCC2)C1]
TABLE A-continued
Compound 14
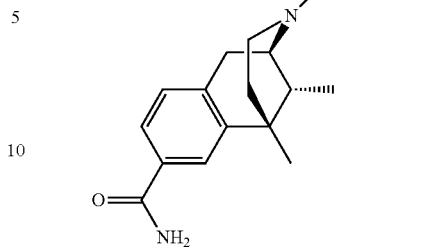
Compound 15
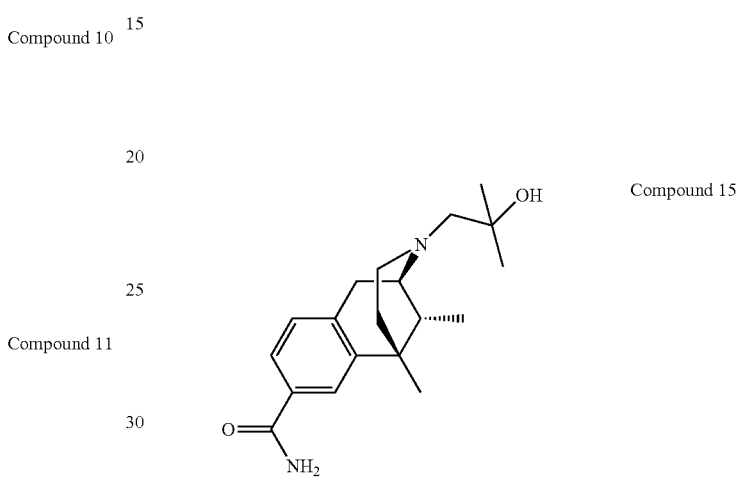
Compound 16
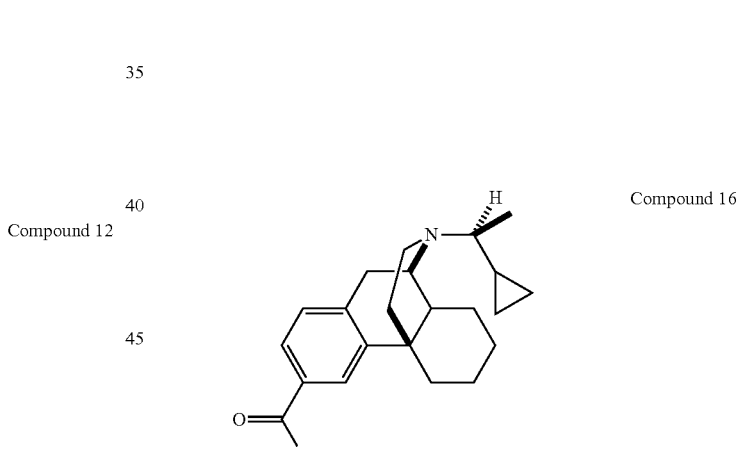
Compound 17
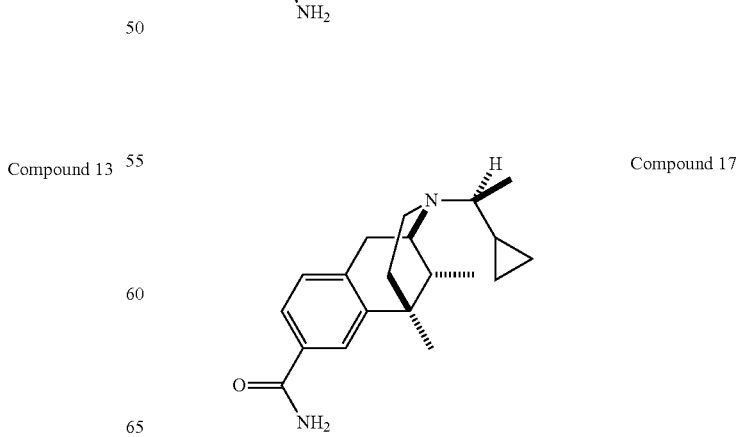

TABLE A-continued
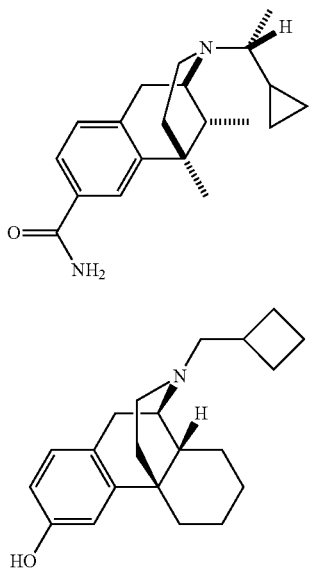
Compound 18
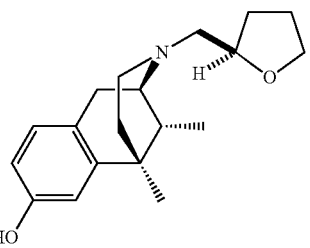
Compound 20
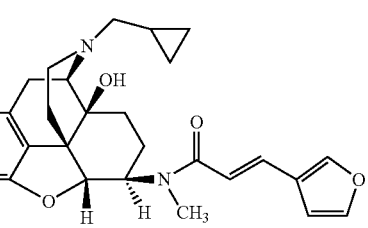
Compound 21
Compound 19
In another embodiment, provided herein are the compounds shown in Table B, or pharmaceutically acceptable salts thereof.
TABLE B
| Structure | mu_Ki | mu_EC50 | mu_Emax | mu_IC50 | mu_Imax |
|---|---|---|---|---|---|
| 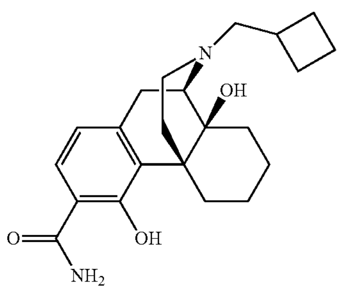 [SMILES: NC(=O)c1ccc2c(c1O)[C@@]13CCCC[C@@]1(O)[C@@H](C2)N(CC1CCC1)CC3] | 0.28 | 1.4 ± 0.06 | 30 ± 2.2 | 4.2 ± 0.6 | 71 ± 0.8 |
| 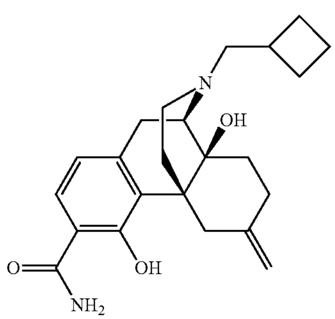 [SMILES: C=C1CC[C@@]2(O)[C@H]3Cc4ccc(C(N)=O)c(O)c4[C@@]2(CCN3CC2CCC2)C1] | 0.11 | 1.1 ± 0.3 | 29 ± 1 | 2.0 ± 0.3 | 74 ± 2 |
| 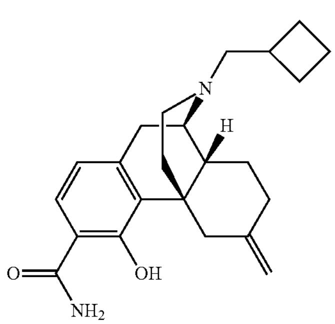 [SMILES: C=C1CC[C@H]2[C@H]3Cc4ccc(C(N)=O)c(O)c4[C@@]2(CCN3CC2CCC2)C1] | 0.097 | 0.53 | 28 | 1.3 | 65 |

TABLE B-continued

| Structure | mu_Ki | mu_EC50 | mu_Emax | mu_IC50 | mu_Imax |
|---|---|---|---|---|---|
| (structure) | 0.22 | 3.3 | 33 | 14 | 69 |
| (structure) | 0.097 | 0.39 | 42 | 1.1 | 54 |
| (structure) | 0.12 | 2.1 | 38 | 5 | 63 |
| (structure) | 0.13 | 1.5 | 44 | 3.7 | 66 |
| (structure) | 0.56 | 4.2 | 49 | 34 | 54 |

TABLE B-continued
| Structure | mu_Ki | mu_EC50 | mu_Emax | mu_IC50 | mu_Imax |
|---|---|---|---|---|---|
| 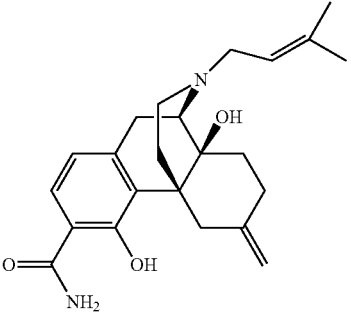 [SMILES: C=C1CC[C@@]2(O)[C@H]3Cc4ccc(C(N)=O)c(O)c4[C@@]2(CCN3CC=C(C)C)C1] | 0.5 | 15 | 35 | 51 | 70 |
| 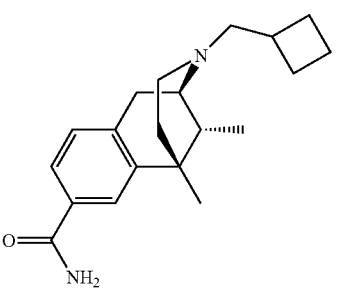 [SMILES: C[C@H]1[C@H]2Cc3ccc(C(N)=O)cc3[C@]1(C)CCN2CC1CCC1] | 0.19 | 2.3 | 36 | 14 | 55 |
| 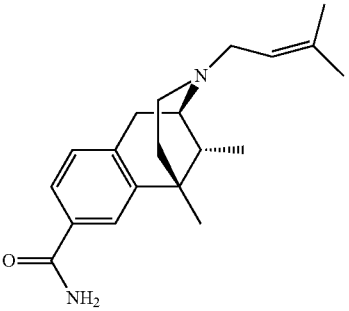 [SMILES: CC(C)=CCN1CC[C@@]2(C)c3cc(C(N)=O)ccc3C[C@@H]1[C@@H]2C] | 2.1 | 110 (12) | 43 (7) | >1300 (280) | 53% @ 10 uM |
| 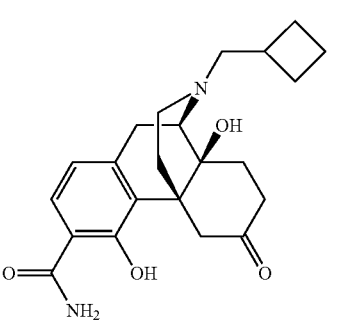 | 0.16 | 1 ± 0.11 | 31 ± 1 | 2.2 ± 0.5 | 69 ± 1.5 |
| 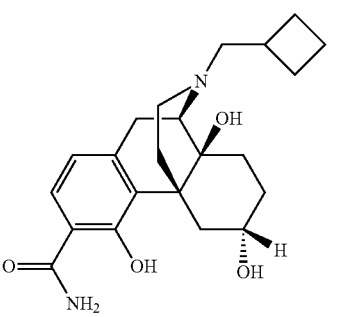 [SMILES: NC(=O)c1ccc2c(c1O)[C@]13CCN(CC4CCC4)[C@H](C2)[C@]1(O)CC[C@H](O)C3] | 0.59 ± 0.07 | 2.8 ± 0.3 | 18 ± 1 | 47 | 78.5 ± 4.5 |

TABLE B-continued

| Structure | mu_Ki | mu_EC50 | mu_Emax | mu_IC50 | mu_Imax |
|---|---|---|---|---|---|
| (structure) | 0.10 ± 0.04 | 0.98 ± 0.12 | 18 ± 5 | 3.8 | 80 ± 1 |

In another embodiment, provided herein are the compounds shown in Table C, or pharmaceutically acceptable salts thereof.

TABLE C

| Structure | mu_Ki | mu_EC50 | mu_Emax | mu_IC50 | mu_Imax |
|---|---|---|---|---|---|
| (structure) | 0.1 | 3.5 | 32 | 3.3 | 73 |
| (structure) | 22 | 60 | 27 | 950 | 65 |
| (structure) | 0.82 | 13 | 26 | 85 | 76 |
| (structure) | 4.6 | 84 | 23 | 210 | 74 |

TABLE C-continued
| Structure | mu_Ki | mu_EC50 | mu_Emax | mu_IC50 | mu_Imax |
|---|---|---|---|---|---|
| 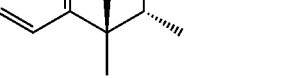 | 0.11 | 4.8 | 53 | 26 | 37 |
| 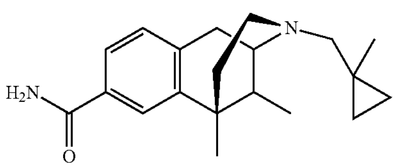 | 1.2 | | 16 | 44 | 85 |
| 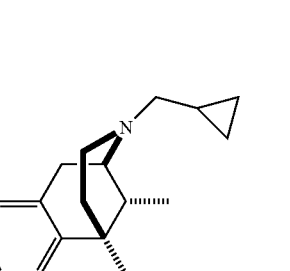 | 0.68 | 22 | 25 | 47 | 83 |
| 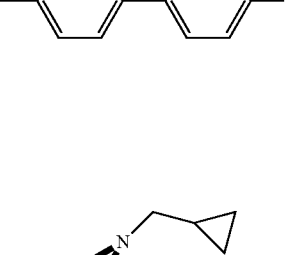 | 0.27 | 5.2 | 32 | 18 | 59 |

TABLE C-continued

| Structure | mu_Ki | mu_EC50 | mu_Emax | mu_IC50 | mu_Imax |
|---|---|---|---|---|---|
| (structure) | 0.37 | 2.9 | 46 | 1.5 | 43 |
| (structure) | 2.3 | 62 | 18 | 170 | 87 |
| Rac (structure) | 3 | 41 | 19 | 170 | 83 |
| (structure) | 23 | 190 | 35 | >3000 | 57 @ 10 uM |
| (structure) | 4.4 | 20 | 20 | 340 | 76 |
| (structure) | 1.2 | | 1.6 | 44 | 85 |

In yet another embodiment, provided herein are the compounds shown in Table E, or pharmaceutically acceptable salts thereof.

TABLE E

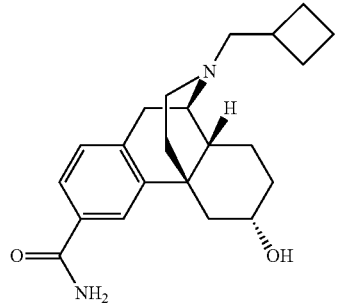 [SMILES: NC(=O)c1ccc2c(c1)[C@]13CCN(CC4CCC4)[C@H](C2)[C@@H]1CC[C@H](O)C3]

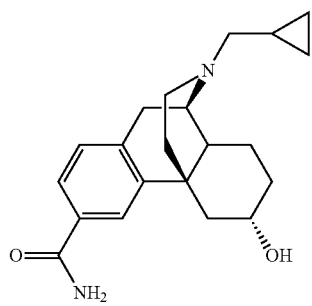 [SMILES: NC(=O)c1ccc2c(c1)[C@]13CCN(CC4CC4)[C@H](C2)C1CC[C@H](O)C3]

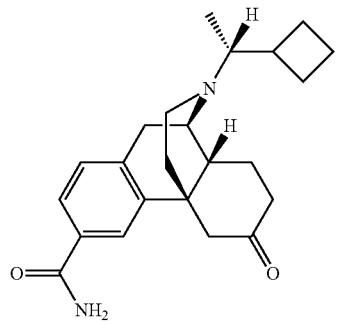 [SMILES: C[C@H](C1CCC1)N1CC[C@]23CC(=O)CC[C@H]2[C@H]1Cc1ccc(C(N)=O)cc13]

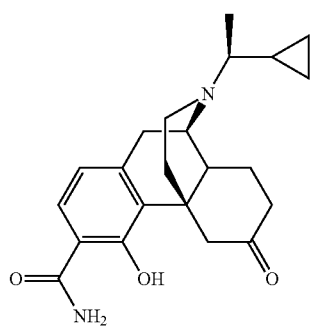 [SMILES: C[C@@H](C1CC1)N1CC[C@]23CC(=O)CCC2[C@H]1Cc1ccc(C(N)=O)c(O)c13]

TABLE E-continued

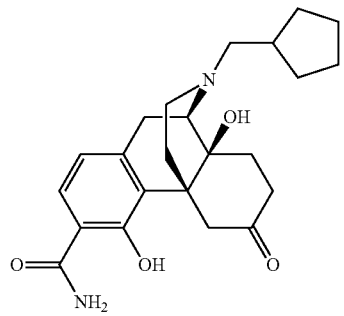 [SMILES: NC(=O)c1ccc2c(c1O)[C@]13CCN(CC4CCCC4)[C@H](C2)[C@]1(O)CCC(=O)C3]

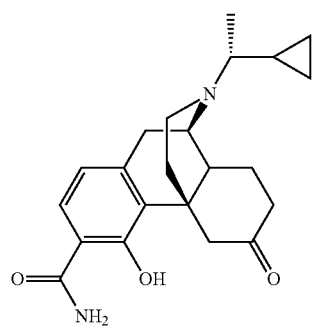 [SMILES: C[C@H](C1CC1)N1CC[C@]23CC(=O)CCC2[C@H]1Cc1ccc(C(N)=O)c(O)c13]

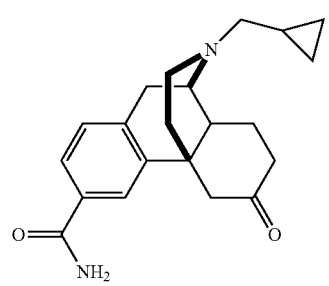

Compound B
mu_Ki: 0.083
mu_EC50: 0.98
mu_Emax: 37
mu_IC50: 2
mu_Imax: 70

The compounds of the present invention are useful for treating a disease or condition by altering a response of an opioid receptor. It has been discovered that compounds having an Emax of 5% to 45% (e.g., 15% to 35%) in a GTPγS binding assay are particularly suitable for treating a depressive symptom. Such compounds are particularly advantageous in that they have a low risk of opioid dependence, opioid addiction and or symptoms of opioid withdrawal.

Accordingly, in certain embodiments of Formulas (I), (Ia), (Ib), (Ic), (II), (IIa), (III), (IV), (IVa), or (V), provided herein is a compound that is a µ opioid receptor to agonist having an Emax of 5% to 45% (e.g., 5, 10, 15, 20, 25, 30, 35, 40, or 45%) in a GTPγS binding assay. In one embodiment, the agonist exhibits an Emax of 15% to 35% in the GTPγS binding assay. In another embodiment, said agonist has a low risk of opioid dependence, opioid addiction and/or symptoms of opioid withdrawal.

It has also been discovered that compounds eliciting a maximal dopamine efflux in the nucleus accumbens in a rat of 125% to 300% over base line are particularly suitable for treating a depressive symptom. Such compounds are particularly advantageous in that they have a low risk of opioid dependence, opioid addiction and/or symptoms of opioid withdrawal.

Accordingly, in certain embodiments of Formulas (I), (Ia), (Ib), (Ic), (II), (IIa), (III), (IV), (IVa), or (V), provided here is a compound that exhibits a maximal dopamine efflux in the nucleus accumbens in a rat of 125% to 300% (e.g., 125, 150, 175, 200, 225, 250, 275, or 300%) over base line. In one embodiment, the maximal dopamine efflux in the nucleus accumbens of a rat is 200% to 300% over base line.

It has further been discovered that compounds that do not attenuate thermal pain in a rodent hot plate model when administered at a dose of at least 1 mg/kg (e.g., 1, 2, 3, 4, 5, 6, 7, 8, 9, 10 mg/kg) are particularly suitable for treatment of a depressive symptom. Such compounds are particularly advantageous in that they have a low risk of opioid dependence, opioid addiction and/or symptoms of opioid withdrawal.

Accordingly, in certain embodiments of Formulas (I), (Ia), (Ib), (Ic), (II), (IIa), (III), (IV), (IVa), or (V), provided herein is a compound that does not attenuate thermal pain in a rodent hot plate model when administered at a dose of at least 1 mg/kg (e.g., 1, 2, 3, 4, 5, 6, 7, 8, 9, or 10 mg/kg). In one embodiment, the compound does not attenuate thermal pain in a rodent hot plate model when administered at a dose of 1-10 mg/kg (e.g., 1, 2, 3, 4, 5, 6, 7, 8, 9, or 10 mg/kg). In one embodiment, the compound does not attenuate thermal pain in a rodent hot plate model when administered at a dose of at least 3 mg/kg. In another embodiment, the compound does not attenuate thermal pain in a rodent hot plate model when administered at a dose of 10 mg/kg. Such compounds are particularly advantageous in that they have a low risk of opioid dependence, opioid addiction and/or symptoms of opioid withdrawal.

Methods of Treatment

The compounds of Formulas (I), (Ia), (Ib), (Ic), (II), (IIa), (III), (IV), (IVa), or (V), provided herein, are particularly suitable for treating a depressive symptom. The depressive symptom can be depressed mood, loss of pleasure, loss of appetite, sleep disturbance, psychomotor changes, fatigue, and/or post-partum depression. The depressive symptom can be associated with a mental condition, wherein the mental condition is schizoaffective disorder, and/or seasonal affective disorder.

The depressive symptom can be acute stress disorder, adjustment disorders with depressed mood, Asperger syndrome, attention deficit, bereavement, bipolar I disorder, bipolar II disorder, borderline and personality disorder, cyclothymia and dysthymia, depression such as major depressive disorder (MDD) and treatment-resistant disorder (TRD), Dysthymic disorder, hyperactivity disorder, impulse control disorder, mixed mania, obsessive-compulsive personality disorder (OCD), paranoid, post-traumatic stress disorder, seasonal affective disorder, self-injury separation, sleep disorder, substance-induced mood disorder, Tourette syndrome and tic disorder, and/or Trichotillomania.

The depressive symptom can also be an anxiety disorder, wherein the anxiety disorder is generalized anxiety disorder, panic, agoraphobia, acute stress, and/or post-traumatic stress disorder.

The depressive symptom can be associated with chronic or recurrent depression.

Accordingly, in one aspect, provided herein is a method of treating a depressive symptom in a subject in need thereof, comprising administering to the subject the compound of Formulas (I), (Ia), (Ib), (Ic), (II), (IIa), (III), (IV), (IVa), or (V), or a pharmaceutically acceptable salt thereof.

In one embodiment, provided herein is a method of treating a depressive symptom in a subject in need thereof, comprising administering to the subject the compound of Formula (I) or a pharmaceutically acceptable salt thereof.

In another embodiment, provided herein is a method of treating a depressive symptom in a subject in need thereof, comprising administering to the subject the compound of Formula (Ia) or a pharmaceutically acceptable salt thereof.

In another embodiment, provided herein is a method of treating a depressive symptom in a subject in need thereof, comprising administering to the subject the compound of Formula (Ib) or a pharmaceutically acceptable salt thereof.

In another embodiment, provided herein is a method of treating a depressive symptom in a subject in need thereof, comprising administering to the subject the compound of Formula (Ic) or a pharmaceutically acceptable salt thereof.

In another embodiment, provided herein is a method of treating a depressive symptom in a subject in need thereof, comprising administering to the subject the compound of Formula (II) or a pharmaceutically acceptable salt thereof.

In another embodiment, provided herein is a method of treating a depressive symptom in a subject in need thereof, comprising administering to the subject the compound of Formula (IIa) or a pharmaceutically acceptable salt thereof.

In still another embodiment, provided herein is a method of treating a depressive symptom in a subject in need thereof, comprising administering to the subject the compound of Formula (III) or a pharmaceutically acceptable salt thereof.

In yet another embodiment, provided herein is a method of treating a depressive symptom in a subject in need thereof, comprising administering to the subject the compound of Formula (IV) or a pharmaceutically acceptable salt thereof.

In yet another embodiment, provided herein is a method of treating a depressive symptom in a subject in need thereof, comprising administering to the subject the compound of Formula (IVa) or a pharmaceutically acceptable salt thereof.

In yet another embodiment, provided herein is a method of treating a depressive symptom in a subject in need thereof, comprising administering to the subject the compound of Formula (V) or a pharmaceutically acceptable salt thereof.

In another aspect, provided herein is a method of treating depression in a subject in need thereof, comprising administering to the subject the compound of Formulas (I), (Ia), (Ib), (Ic), (II), (IIa), (III), (IV), (IVa), or (V), or a pharmaceutically acceptable salt thereof.

In one embodiment, provided herein is a method of treating depression in a subject in need thereof, comprising administering to the subject the compound of Formula (I) or a pharmaceutically acceptable salt thereof.

In another embodiment, provided herein is a method of treating depression in a subject in need thereof, comprising administering to the subject the compound of Formula (Ia) or a pharmaceutically acceptable salt thereof.

In another embodiment, provided herein is a method of treating depression in a subject in need thereof, comprising administering to the subject the compound of Formula (Ib) or a pharmaceutically acceptable salt thereof.

In another embodiment, provided herein is a method of treating depression in a subject in need thereof, comprising administering to the subject the compound of Formula (Ic) or a pharmaceutically acceptable salt thereof.

In another embodiment, provided herein is a method of treating depression in a subject in need thereof, comprising administering to the subject the compound of Formula (II) or a pharmaceutically acceptable salt thereof.

In another embodiment, provided herein is a method of treating depression in a subject in need thereof, comprising administering to the subject the compound of Formula (IIa) or a pharmaceutically acceptable salt thereof.

In still another embodiment, provided herein is a method of treating depression in a subject in need thereof, comprising administering to the subject the compound of Formula (III) or a pharmaceutically acceptable salt thereof.

In yet another embodiment, provided herein is a method of treating depression in a subject in need thereof, comprising administering to the subject the compound of Formula (IV) or a pharmaceutically acceptable salt thereof.

In yet another embodiment, provided herein is a method of treating depression in a subject in need thereof, comprising administering to the subject the compound of Formula (IVa) or a pharmaceutically acceptable salt thereof.

In yet another embodiment, provided herein is a method of treating depression in a subject in need thereof, comprising administering to the subject the compound of Formula (V) or a pharmaceutically acceptable salt thereof.

In one specific embodiment, provided herein is a method of treating depression and/or a depressive symptom in a subject in need thereof, comprising administering to the subject the compound:

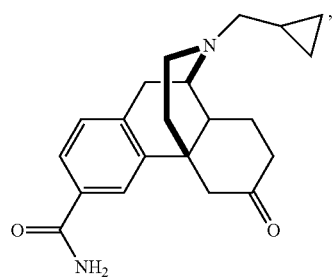

or a pharmaceutically acceptable salt thereof.

It has been discovered that Emax value in a GTPγS binding assay can be used to select μ opioid receptor agonists for treatment of a depressive symptom. In particular, it has been discovered that compounds with an Emax of 5% to 45% in a GTPγS binding assay are especially suitable for treating depressive symptoms. Thus, in another aspect, provided herein is a method of treating a depressive symptom in a subject in need thereof comprising administering to the subject an effective amount of a μ opioid receptor agonist that exhibits an Emax of 5% to 45% (e.g., 5, 10, 15, 20, 25, 30, 35, 40, or 45%) in a GTPγS binding assay. In a particular embodiment, the Emax of the agonist is 15% to 35% in the GTPγS binding assay. In another embodiment, the agonist has a low risk of opioid dependence, opioid addiction and or symptoms of opioid withdrawal. Non-limiting examples of such a μ opioid receptor agonists are the compounds of Formulas (I), (Ia), (Ib), (Ic), (II), (IIa), (III), (IV), (IVa), and (V).

It has also been discovered that a compound that exhibits a maximal dopamine efflux in the nucleus accumbens in a rat of 125% to 300% over base line is particularly suitable for treatment of depressive symptoms. Thus, in another aspect, provided herein is a method of treating a depressive symptom in a subject in need thereof comprising administering to the subject an effective amount of a compound that exhibits a maximal dopamine efflux in the nucleus accumbens in a rat of 125% to 300% (e.g., 125, 150, 175, 200, 225, 250, 275, or 300%) over base line. In particular embodiments, the maximal dopamine efflux in the nucleus accumbens in a rat is 200% to 300% over base line. Non-limiting examples of such compounds are the compounds of Formulas (I), (Ia), (Ib), (Ic), (II), (IIa), (III), (IV), (IVa), and (V).

In still another aspect, provided herein is a method of treating a depressive symptom in a subject in need thereof comprising administering to the subject an effective amount of a compound that does not attenuate thermal pain in a rodent hot plate model when administered at of dose of at least 1 mg/kg (e.g., 1, 2, 3, 4, 5, 6, 7, 8, 9, or 10 mg/kg). In one embodiment, the compound does not attenuate thermal pain in a rodent hot plate model when administered at a dose of 1-10 mg/kg (e.g., 1, 2, 3, 4, 5, 6, 7, 8, 9, or 10 mg/kg). In one embodiment, the compound does not attenuate thermal pain in a rodent hot plate model when administered at a dose of at least 3 mg/kg. In another embodiment, the compound does not attenuate thermal pain in a rodent hot plate model when administered at a dose of 10 mg/kg. Non-limiting examples of such a μ opioid receptor agonists are the compounds of Formulas (I), (Ia), (Ib), (Ic), (II), (IIa), (III), (IV), (IVa), and (V).

In certain embodiments of the methods described above, the depressive symptom is depressed mood, loss of pleasure, loss of appetite, sleep disturbance, psychomotor changes, fatigue, and/or post-partum depression.

In another embodiment, the depressive symptom is associated with a mental condition, wherein the mental condition is schizoaffective disorder, and/or seasonal affective disorder.

In still another embodiment, the depressive symptom is acute stress disorder, adjustment disorders with depressed mood, Asperger syndrome, attention deficit, bereavement, bipolar I disorder, bipolar II disorder, borderline and personality disorder, cyclothymia and dysthymia, depression such as major depressive disorder (MDD) and treatment-resistant disorder (TRD), Dysthymic disorder, hyperactivity disorder, impulse control disorder, mixed mania, obsessive-compulsive personality disorder (OCD), paranoid, post-traumatic stress disorder, seasonal affective disorder, self-injury separation, sleep disorder, substance-induced mood disorder, Tourette syndrome and tic disorder, and/or Trichotillomania.

In yet another embodiment, the depressive symptom is an anxiety disorder, wherein the anxiety disorder is generalized anxiety disorder, panic, agoraphobia, acute stress and/or post-traumatic stress disorder. In another embodiment, the depressive symptom is associated with chronic or recurrent depression.

In another aspect, provided herein is a method of treating a disease or condition associated with the group consisting of pain, pruritis, diarrhea, irritable bowel syndrome, gastrointestinal motility disorder, obesity, respiratory depression, convulsions, coughing, hyperalgesia, and drug addiction in a subject comprising administering to the subject a pharmaceutical composition comprising the compound of Formulas (I), (Ia), (Ib), (Ic), (II), (IIa), (III), (IV), (IVa), or (V) as defined above, or a pharmaceutically acceptable salt thereof.

In one embodiment, the drug addiction is selected from heroin, cocaine, nicotine, amphetamine and alcohol addiction.

In a further aspect, the invention is a method of treating a disease or condition in a subject by altering a response mediated by an opioid receptor comprising bringing into contact with the opioid receptor an effective amount of the compound of Formulas (I), (Ia), (Ib), (Ic), (II), (IIa), (III), (IV), (IVa), or (V) as defined above.

In preferred embodiments of the methods described above, the subject is a human.

Definitions

The term "treat," "treated," "treating" or "treatment" includes the diminishment or alleviation of at least one symptom associated or caused by the state, disorder or disease being treated. In certain embodiments, the treatment comprises bringing into contact with the opioid receptor an effective amount of a μ opioid receptor agonist, such as a compound of Formulas (I), (Ia), (Ib), (Ic), (II), (IIa), (III) or (IV), (IVa), or (V).

The term "subject" is intended to be a mammal Examples of subjects include humans, dogs, cows, horses, pigs, sheep, goats, cats, mice, rabbits, rats, and transgenic non-human animals. In preferred embodiments, the subject is a human, e.g., a human suffering from a depressive symptom, pain, pruritis, diarrhea, irritable bowel syndrome, gastrointestinal motility disorder, obesity, respiratory depression, convulsions, coughing, hyperalgesia, or drug addiction.

As used to herein, the term "GTPγS binding assay" refers to the GTPγS binding assay described in Example B1, herein. This GTPγS binding assay is performed under conditions such that the observed Emax value for buprenorphine (CAS#52485-79-7) in this assay is at least 50% compared to baseline.

As used to herein, the term "Emax" refers to the maximal observed effect of a compound. In certain embodiments, the Emax is the maximal percentage increase of [35S]GTPγS binding induced by an agonist relative to basal [35S]GTPγS binding in the absence of any drug.

As used to herein, the term "EC50" refers to the concentration of a compound required to achieve an effect that is 50% of the Emax.

As used to herein, the term "rodent hot plate model" refers to the thermal pain assay described in Example B2, herein.

As used herein the term "low risk of opioid dependence, opioid addiction and or symptoms of opioid withdrawal" refers to low "abuse liability." Drugs with "abuse liability" are those associated with physical and/or psychological dependence in humans, or with a probability for diversion from the intended medical condition for recreational use. There are a variety of animal models that can be used to assess the abuse liability of drugs. In general, these models use comparator drugs with known high abuse potential. For the opioid class of compounds, the most common comparator drug is morphine. Morphine has been shown clinically to have a high potential for abuse. Morphine produces a "drug high," dependency when the drug is repeatedly administered, and withdrawal when the drug use is abruptly stopped. Each of these traits can be evaluated in animal models for a given experimental drug to determine its relative risk compared to morphine. For example, efflux of nucleus accumbens dopamine can be evaluated as a predictor of the high or euphoria following administration of the drug. A reduction in the maximal possible observed increase in dopamine efflux would be correlated with a significantly lower degree of euphoria and a reduction in the abuse liability associated with drug-liking. Similarly, the potential for dependence and withdrawal can be determined in standard animal models in which the drug is administer 1-3 times per day, or by continual infusion for 5 to 14 days, followed by abrupt withdrawal. For addictive opioids, abrupt cessation of administration of the drug will cause withdrawal characterized by such traits as weight-loss associated with excessive urination and defecation, increased shaking behavior, increased "jumping" activity, and reduced body temperature. These are quantitative measures that can be used to evaluate the relative risk for dependency compared to morphine. The ability of a drug to induce withdrawal in opioid-dependent patients will also lead to a reduced abuse liability associated with diversion of the drug. This feature can also be directly assessed in animals by making them dependent on morphine, or another opioid agonist, and then precipitating withdrawal by the administration of the drug. In certain embodiments, the compounds disclosed herein have a lower abuse liability (e.g., a lower risk of opioid dependence, opioid addiction and or symptoms of opioid withdrawal) than buprenorphine.

As used herein, the term "alkyl" refers to a fully saturated branched or unbranched hydrocarbon moiety. Preferably the alkyl comprises 1 to 20 carbon atoms, more preferably 1 to 16 carbon atoms, 1 to 10 carbon atoms, 1 to 7 carbon atoms, 1 to 6 carbons, 1 to 4 carbons, or 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. Furthermore, the expression "$C_x$-$C_y$-alkyl", wherein x is 1-5 and y is 2-10 indicates a particular alkyl group (straight- or branched-chain) of a particular range of carbons. For example, the expression $C_1$-$C_4$-alkyl includes, but is not limited to, methyl, ethyl, propyl, butyl, isopropyl, tert-butyl and isobutyl.

The term "alkenyl," alone or in combination refers to a straight-chain, cyclic or branched hydrocarbon residue comprising at least one olefinic bond and the indicated number of carbon atoms. Preferred alkenyl groups have up to 8, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl, isobutenyl, 1-cyclohexenyl, 1-cyclopentenyl.

As used herein, the term "cycloalkyl" or "carbocyclic" refers to saturated or unsaturated monocyclic, bicyclic or tricyclic hydrocarbon groups of 3-12 carbon atoms, preferably 3-9, or 3-7 carbon atoms. Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

"Alkoxyalkyl" refers to a group having the formula —$R^i$—$OR^{ii}$, wherein $R^i$ is an alkyl group as defined above, and $OR^{ii}$ is an alkoxy group as defined below.

"Alkoxy" refers to those alkyl groups, having from 1 to 10 carbon atoms, attached to the remainder of the molecule via an oxygen atom. Alkoxy groups with 1-8 carbon atoms are preferred. The alkyl portion of an alkoxy may be linear, cyclic, or branched, or a combination thereof. Examples of alkoxy groups include methoxy, ethoxy, isopropoxy, butoxy, cyclopentyloxy, and the like. An alkoxy group can also be represented by the following formula: —$OR^i$, where $R^i$ is the "alkyl portion" of an alkoxy group.

The term "hydroxyalkyl" refers to a group having the formula —$R^{iii}$—OH, wherein $R^{iii}$ is an alkyl group as defined above.

The term "aryl" includes aromatic monocyclic or multicyclic e.g., tricyclic, bicyclic, hydrocarbon ring systems consisting only of hydrogen and carbon and containing from six to nineteen carbon atoms, or six to ten carbon atoms, where the ring systems may be partially saturated. Aryl groups include, but are not limited to, groups such as phenyl, tolyl, xylyl, anthryl, naphthyl and phenanthryl. Aryl groups can also be fused or bridged with alicyclic or heterocyclic rings which are not aromatic so as to form a polycycle (e.g., tetralin).

The term "heteroaryl," as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

The term "heterocycle" or "heterocyclyl" refers to a five-member to ten-member, fully saturated or partially unsaturated nonaromatic heterocylic groups containing at least one heteroatom such as O, S or N. The most frequent examples are piperidinyl, morpholinyl, piperazinyl, pyrrolidinyl or pirazinyl. Attachment of a heterocyclyl substituent can occur via a carbon atom or via a heteroatom.

Moreover, the alkyl, alkenyl, cycloalkyl, cycloalkenyl, alkoxy, aryl, heteroaryl, and heterocycle groups described above can be "unsubstituted" or "substituted." The term "substituted" is intended to describe moieties having substituents replacing a hydrogen on one or more atoms, e.g. C, O or N, of a molecule. Such substituents can independently include, for example, one or more of the following: straight or branched alkyl (preferably $C_1$-$C_5$), cycloalkyl (preferably $C_3$-$C_8$), alkoxy (preferably $C_1$-$C_6$), thioalkyl (preferably $C_1$-$C_6$), alkenyl (preferably $C_2$-$C_6$), alkynyl (preferably $C_2$-$C_6$), heterocyclic, carbocyclic, aryl (e.g., phenyl), aryloxy (e.g., phenoxy), aralkyl (e.g., benzyl), aryloxyalkyl (e.g., phenyloxyalkyl), arylacetamidoyl, alkylaryl, heteroaralkyl, alkylcarbonyl and arylcarbonyl or other such acyl group, heteroarylcarbonyl, or heteroaryl group, $(CR'R'')_{0-3}NR'R''$ (e.g., $-NH_2$), $(CR'R'')_{0-3}CN$ (e.g., $-CN$), $-NO_2$, halogen (e.g., $-F$, $-Cl$, $-Br$, or $-I$), $(CR'R'')_{0-3}C(halogen)_3$ (e.g., $-CF_3$), $(CR'R'')_{0-3}CH(halogen)_2$, $(CR'R'')_{0-3}CH_2(halogen)$, $(CR'R'')_{0-3}CONR'R''$, $(CR'R'')_{0-3}(CNH)NR'R''$, $(CR'R'')_{0-3}S(O)_{1-2}NR'R''$, $(CR'R'')_{0-3}CHO$, $(CR'R'')_{0-3}O(CR'R'')_{0-3}H$, $(CR'R'')_{0-3}S(O)_{0-3}R'$ (e.g., $-SO_3H$, $-OSO_3H$), $(CR'R'')_{0-3}O(CR'R'')_{0-3}H$ (e.g., $-CH_2OCH_3$ and $-OCH_3$), $(CR'R'')_{0-3}S(CR'R'')_{0-3}H$ (e.g., $-SH$ and $-SCH_3$), $(CR'R'')_{0-3}OH$ (e.g., $-OH$), $(CR'R'')_{0-3}COR'$, $(CR'R'')_{0-3}$ (substituted or unsubstituted phenyl), $(CR'R'')_{0-3}(C_3$-$C_8$ cycloalkyl), $(CR'R'')_{0-3}CO_2R'$ (e.g., $-CO_2H$), or $(CR'R'')_{0-3}OR'$ group, or the side chain of any naturally occurring amino acid; wherein R' and R'' are each independently hydrogen, a $C_1$-$C_5$ alkyl, $C_2$-$C_5$ alkenyl, $C_2$-$C_5$ alkynyl, or aryl group.

As used herein, the term "acyl" refers to an organic radical linked to a carbonyl.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17.sup.th ed., Mack Publishing Company, Easton, Pa., 1985, p. 1418 and Journal of Pharmaceutical Science, 66, 2 (1977), each of which is incorporated herein by reference in its entirety.

The description of the disclosure herein should be construed in congruity with the laws and principals of chemical bonding. For example, it may be necessary to remove a hydrogen atom in order accommodate a substituent at any given location. Furthermore, it is to be understood that definitions of the variables (i.e., "R groups"), as well as the bond locations of the generic formulae of the invention (e.g., Formulas I, Ia, Ib, Ic, II, IIa, III, IV, IVa, or V), will be consistent with the laws of chemical bonding known in the art. It is also to be understood that all of the compounds of the invention described above will further include bonds between adjacent atoms and/or hydrogens as required to satisfy the valence of each atom. That is, bonds and/or hydrogen atoms are added to provide the following number of total bonds to each of the following types of atoms:carbon:four bonds; nitrogen: three bonds; oxygen: two bonds; and sulfur: two-six bonds.

The compounds of this invention may include asymmetric carbon atoms. It is to be understood accordingly that the isomers arising from such asymmetry (e.g., all enantiomers, stereoisomers, rotamers, tautomers, diastereomers, or racemates) are included within the scope of this invention. Such isomers can be obtained in substantially pure form by classical separation techniques and by stereochemically controlled synthesis. Furthermore, the structures and other compounds and moieties discussed in this application also include all tautomers thereof. Compounds described herein may be obtained through art recognized synthesis strategies.

It will also be noted that the substituents of some of the compounds of this invention include isomeric cyclic structures. It is to be understood accordingly that constitutional isomers of particular substituents are included within the scope of this invention, unless indicated otherwise. For example, the term "tetrazole" includes tetrazole, 2H-tetrazole, 3H-tetrazole, 4H-tetrazole and 5H-tetrazole.

Pharmaceutical Compositions

The compounds of the present invention are suitable as active agents in pharmaceutical compositions that are efficacious particularly for treating a depressive symptom, e.g. depressed mood, loss of pleasure, loss of appetite, sleep disturbance, psychomotor changes, fatigue, or post-partum depression, or combinations thereof. The compounds of the present invention are also suitable as active agents in pharmaceutical compositions that are efficacious particularly for treating pain, pruritis, diarrhea, irritable bowel syndrome, gastrointestinal motility disorder, obesity, to respiratory depression, convulsions, coughing, hyperalgesia, and/or drug addiction. The pharmaceutical composition in various embodiments has a pharmaceutically effective amount of the present active agent along with other pharmaceutically acceptable excipients, carriers, fillers, diluents and the like.

The language "pharmaceutically effective amount" or "pharmaceutically acceptable amount" of the compound is that amount necessary or sufficient to treat the corresponding disease or condition, e.g. treating a depressive symptom in a subject in need of, or treating in a subject in need of a disease or condition associated with pain, pruritis, diarrhea, irritable bowel syndrome, gastrointestinal motility disorder, obesity, respiratory depression, convulsions, coughing, hyperalgesia, or drug addiction, or combinations thereof. In an example, an effective amount of a compound of the invention is the amount sufficient to alter a response of an opioid receptor in a subject. The effective amount can vary depending on such factors as the size and weight of the subject, the type of illness, or the particular compound of the invention. For example, the choice of the compound of the invention can affect what constitutes an "effective amount." One of ordinary skill in the art would be able to study the factors contained herein and make the determination regarding the effective amount of the compounds of the invention without undue experimentation.

The regimen of administration can affect what constitutes a pharmaceutically effective amount. A compound of the invention can be administered to the subject either prior to or after the onset of a disease or condition provided herein. Further, several divided dosages, as well as staggered dosages can be administered daily or sequentially, or the dose can be continuously infused, or can be a bolus injection. Further, the dosages of the compound(s) of the invention can be proportionally increased or decreased as indicated by the exigencies of the therapeutic or prophylactic situation.

In one non-limiting embodiment, the phrase "pharmaceutically effective amount" refers to the amount of a compound of the present invention that, when administered to a subject, is effective to (1) at least partially alleviate, inhibit, prevent and/or ameliorate a condition, or a disorder or a disease mediated by an opioid receptor, or (2) altering a response of an opioid receptor. In another non-limiting embodiment, the phrase "pharmaceutically effective amount" refers to the amount of a compound of the present invention that, when administered to a subject, is effective to at least partially alleviate, inhibit, prevent and/or ameliorate a depressive symptom, to such as depressed mood, loss of pleasure, loss of appetite, sleep disturbance, psychomotor changes, fatigue, and/or post-partum depression. In still another non-limiting embodiment, the term "pharmaceutically effective amount" refers to the amount of a compound of the present invention that, when administered to a subject, at least partially alleviate, inhibit, prevent and/or ameliorate a disease or condition associated with the group consisting of pain, pruritis, diarrhea, irritable bowel syndrome, gastrointestinal motility disorder, obesity, respiratory depression, convulsions, coughing, hyperalgesia, and/or drug addiction.

The effective amount can vary depending on such factors as the size and weight of the subject, the type of illness, or the particular organic compound. For example, the choice of the organic compound can affect what constitutes an "effective amount." One of ordinary skill in the art would be able to study the aforementioned factors and make the determination regarding the acceptable amount of the organic compound without undue experimentation.

Compounds of the invention may be used in the treatment of states, disorders or diseases as described herein, or for the manufacture of pharmaceutical compositions for use in the treatment of these diseases.

The language "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1 to 99.5% (more preferably, 0.5 to 90%) of active ingredient in combination with a pharmaceutically acceptable carrier.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; to malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, buccal, sublingual, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and to then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be to reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissue.

The preparations of the present invention may be given orally, parenterally, topically, or rectally. They are of course given by forms suitable for each to administration route. For example, they are administered in tablets or capsule form, by injection, inhalation, eye lotion, ointment, suppository, etc., administration by injection, infusion or inhalation; topical by lotion or ointment; and rectal by suppositories. Oral and/or IV administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the to treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 1.0 to about 100 mg per kg per day. An effective amount is that amount treats a protein kinase-associated disorder.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

EXEMPLIFICATION OF THE INVENTION

The invention is further illustrated by the following examples, which should not be construed as further limiting. The practice of the present invention will employ, unless otherwise indicated, conventional techniques of cell biology, cell culture, molecular biology, transgenic biology, microbiology and immunology, which are within the skill of the art.

Part A. Synthetic Procedures

Synthesis procedures for preparation of the compounds of the invention are readily available to the ordinary skilled artisan. For example, U.S. Pat. No. 7,262,298 and PCT publication WO2012/088494 illustrate synthesis methods for the compounds of Formulas (I), (Ia), (Ib), and (Ic), which are morphinan analogues;

U.S. Pat. No. 8,252,929 provides synthesis methods for the compounds of Formulas (II) and (IIa), which are morphan analogues;

U.S. Pat. No. 8,026,252 provides synthesis methods for the compounds of Formula (III), which are morphan and morphinan analogues with large substituents attached to the phenyl;

Neumeyer et al. (Journal of Med. Chem. 2012, p 3878) shows exemplary synthesis methods for the compounds of Formulas (IV) and (Iva), which are morphinan analogues and can have a —NH—CH$_2$-phenyl substitution group on the phenyl; and U.S. Pat. No. 8,252,929 provides synthesis methods for the compounds of Formula (V), which are morphine analogues.

All of the above-referenced patents and literatures are incorporated herein by reference in their entirety.

General Procedure to Synthesize a NH Core Compound

Synthesis of (4R,4aR,7aR,12bS)-3-methyl-1,2,3,4,4a,5,6,7a-octahydrospiro[4,12-methanobenzofuro[3,2-e]isoquinoline-7,2'-[1,3]dioxolan]-9-ol

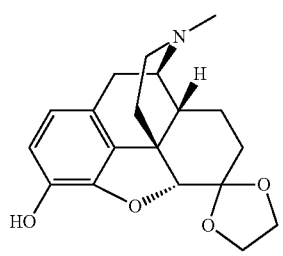

To Hydromorphone HCl (15.0 g, 46.7 mmol) was added ethylene glycol (80 mL) and methane sulfonic acid (10 mL) and the reaction heated at 80° C. overnight. The reaction was cooled to room temperature and poured into ice/NH$_{3(aq)}$ (~350 mL). The product was extracted with dichloromethane and dried over MgSO$_4$ before concentration under reduced pressure to give (4R,4aR,7aR,12bS)-3-methyl-1,2,3,4,4a,5,6,7a-octahydrospiro[4,12-methanobenzofuro[3,2-e]isoquinoline-7,2'-[1,3]dioxolan]-9-ol (19 g, 99.9% LCMS); [M+H]+ 330.5. This was taken onto the next step without purification.

Synthesis of (4R,4aR,7aR,12bS)-3-methyl-1,2,3,4,
4a,5,6,7a-octahydrospiro[4,12-methanobenzofuro[3,
2-e]isoquinoline-7,2'-[1,3]dioxolan]-9-yl trifluoromethanesulfonate

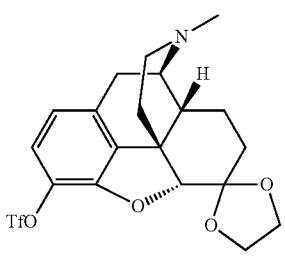

To a mixture of (4R,4aR,7aR,12bS)-3-methyl-1,2,3,4,4a,5,6,7a-octahydrospiro[4,12-methanobenzofuro[3,2-e]isoquinoline-7,2'-[1,3]dioxolan]-9-ol (21.54 g, 46.73 mmol) and triethylamine (20 mL, 140.2 mmol) in dichloromethane (600 mL) was added N-Phenylbis(trifluoromethanesulfonamide) (17.53 g, 49.0 mmol) and the mixture stirred at room temperature overnight. The solvent was concentrated under reduced pressure and the residue taken up in 20% hexane in ethyl acetate (1 L) and washed with water (×5). The organic phase was dried (MgSO$_4$). Filtration and removal of the solvent under reduced pressure gave (4R,4aR,7aR,12bS)-3-methyl-1,2,3,4,4a,5,6,7a-octahydrospiro[4,12-methanobenzofuro[3,2-e]isoquinoline-7,2'-[1,3]dioxolan]-9-yltrifluoromethanesulfonate (20.77 g, 96% pure LCMS); [M+H]+ 462.1.

Synthesis of (4R,4aR,7aR,12bS)-3-methyl-1,2,3,4,
4a,5,6,7a-octahydrospiro[4,12-methanobenzofuro[3,
2-e]isoquinoline-7,2'-[1,3]dioxolane]-9-carbonitrile

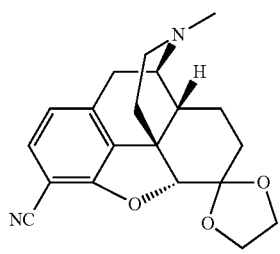 [SMILES: CN1CC[C@]23c4c5ccc(O)c4O[C@H]2C2(CC[C@H]3[C@H]1C5)OCCO2]

To a solution of (4R,4aR,7aR,12bS)-3-methyl-1,2,3,4,4a,5,6,7a-octahydrospiro[4,12-methanobenzofuro[3,2-e]isoquinoline-7,2'-[1,3]dioxolan]-9-yl trifluoromethanesulfonate (20.77 g, 45.0 mmol) in degassed dimethylformamide (400 mL) was added tetrakis(triphenylphosphine)palladium(0) (5.21 g, 4.50 mmol). After heating to 40° C., zinc cyanide (3.18 g, 27.0 mmol) was added and the reaction mixture heated at 110° C. for 6 hours. The reaction mixture was cooled to room to temperature and diluted with ethyl acetate and filtered through a pad of celite. The filtrate was diluted further with ethyl acetate and washed with water (3×500 mL). The aqueous phase was basified with sodium hydrogen carbonate solution and re-extracted with ethyl acetate and the combined organics dried (MgSO$_4$), filtered and concentrated under reduced pressure. Purification by silica chromatography (100% dichloromethane to 5% NH$_3$/methanol in dichloromethane) gave (4R,4aR,7aR,12bS)-3-methyl-1,2,3,4,4a,5,6,7a-octahydrospiro[4,12-methanobenzofuro[3,2-e]isoquinoline-7,2'-[1,3]dioxolane]-9-carbonitrile (10.0 g, 91% pure LCMS, 63% yield over three steps); [M+H]+ 339.1.

Synthesis of (4R,4aR,7aR,12bS)-1,2,3,4,4a,5,6,7a-octahydrospiro[4,12-methanobenzofuro[3,2-e]isoquinoline-7,2'-[1,3]dioxolane]-9-carbonitrile

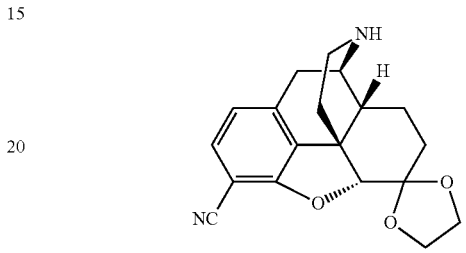

To a suspension of (4R,4aR,7aR,12bS)-3-methyl-1,2,3,4,4a,5,6,7a-octahydrospiro[4,12-methanobenzofuro[3,2-e]isoquinoline-7,2'-[1,3]dioxolane]-9-carbonitrile (5.0 g, 17.8 mmol) in dimethylformamide (50 mL) was added diisopropyl azodicarboxylate (5.4 mL, 27.5 mmol). The reaction was heated to 55° C. for 3 hours until the starting material was consumed. To the reaction was added dimedone (5.8 g, 41.4 mmol) and methanol (1.75 mL, 54.8 mmol) and the reaction heated to 60° C. for 3 hours. The reaction was allowed to cool to room temperature and poured into 0.5 M HCl$_{(aq)}$ (50 mL). The aqueous phase was washed with diethyl ether: ethyl acetate (3:1). The organic phase was back extracted with 0.5 M HCl$_{(aq)}$ and acidic phases combined before basifying with 2M NaOH until pH9. The aqueous phase was extracted with ethyl acetate (×3). The combined organic phases were washed with water/brine (×3) before drying over MgSO$_4$ and concentrating under reduced pressure. The residue was purified by silica chromatography (5% methanol in dichloromethane to 5% NH$_3$/methanol in dichloromethane) to give to (4R,4aR,7aR,12bS)-1,2,3,4,4a,5,6,7a-octahydrospiro[4,12-methanobenzofuro[3,2-e]isoquinoline-7,2'-[1,3]dioxolane]-9-carbonitrile as a pale yellow solid (3.90 g, 95% pure LCMS, 81% yield); [M+H]+ 325.1.

General Procedure to Synthesize a Deoxygenated Core Compound

Synthesis of (4R,4aR,7aR,12bS)-9-(benzyloxy)-3-methyl-2,3,4,4a,5,6-hexahydro-1H-4,12-methanobenzofuro[3,2-e]isoquinolin-7(7aH)-one

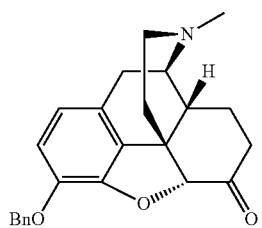

To Hydromorphone HCl (50.0 g, 155.3 mmol) in dimethylformamide (500 mL) was added sodium hydride (14.30 g, 357.4 mmol) portionwise with cooling. The addition was conducted over 25 minutes. The reaction was stirred at room temperature for 1.5 hours before the addition of benzyl chloride (17.88 mL, 357.4 mmol) over 10 minutes with cooling. The reaction was allowed to warm to room temperature and stirred for 40 hours. The reaction was incomplete so additional benzyl chloride (1.79 mL, 15.5 mmol) was added. After 4 hours, the reaction was quenched with water (60 mL), acidified with aqueous HCl (2M, 800 mL) and washed with ethyl acetate/diethyl ether (3:1) (2×800 mL). The aqueous phase was basified with aqueous NaOH (2M, 800 mL) and extracted with ethyl acetate (2×1 L). The organic phases were combined, washed with water/brine (1:1) (2×800 mL) and dried over MgSO$_4$ before concentration under reduced pressure. The residue was taken up in ethyl acetate and washed with water/brine (2×500 mL), dried over MgSO$_4$ before concentration under reduced pressure to give (4R,4aR,7aR,12bS)-9-(benzyloxy)-3-methyl-2,3,4,4a,5,6-hexahydro-1H-4,12-methanobenzofuro[3,2-e]isoquinolin-7(7aH)-one (47.9 g, 95% pure by NMR, 82% yield); [M+H]$^+$ 376.2. This was taken onto the next step without purification.

Synthesis of (4bS,8aR,9R)-3-(benzyloxy)-4-hydroxy-11-methyl-8,8a,9,10-tetrahydro-5H-9,4b-(epiminoethano)phenanthren-6(7H)-one

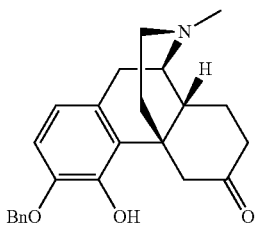

To (4R,4aR,7aR,12bS)-9-(benzyloxy)-3-methyl-2,3,4,4a,5,6-hexahydro-1H-4,12-methanobenzofuro[3,2-e]isoquinolin-7(7aH)-one (58.32 g, 0.16 mol) in ethanol (1.55 L) was added ammonium chloride (124.65 g, 2.33 mol) and zinc powder (101.59 g, 1.55 mol). The reaction was heated to reflux and monitored by TLC. Once complete, the reaction was allowed to cool and filtered through a pad of celite. The pad was washed thoroughly with ethanol (1 L) and methanol (1 L). The filtrate was concentrated under reduced pressure. The residue was taken up in dichloromethane and aqueous ammonia (~15%, 1 L) before the product was extracted with dichloromethane (3×700 mL). The dichloromethane phases were combined, washed with brine and dried over MgSO$_4$ before being concentrated under reduced pressure. The residue was purified by silica chromatography eluted with 10% methanol, 5% Et$_3$N in dichloromethane to give (4bS,8aR,9R)-3-(benzyloxy)-4-hydroxy-11-methyl-8,8a,9,10-tetrahydro-5H-9,4b-(epiminoethano)phenanthren-6(7H)-one (50.4 g, 74.3% pure LCMS, 64% yield); [M+H]$^+$ 378.2.

Synthesis of (4bS,8aR,9R)-3-(benzyloxy)-11-methyl-6-oxo-6,7,8,8a,9,10-hexahydro-5H-9,4b-(epiminoethano)phenanthren-4-yltrifluoromethanesulfonate

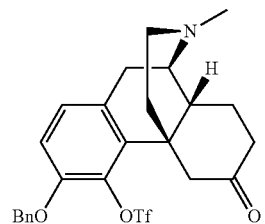

To a solution of (4bS,8aR,9R)-3-(benzyloxy)-4-hydroxy-11-methyl-8,8a,9,10-tetrahydro-5H-9,4b-(epiminoethano)phenanthren-6(7H)-one (28.2 g, 74.7 mmol) in tetrahydrofuran under an atmosphere of argon at 0° C. was added sodium hydride (4.48 g, 112.1 mmol) portionwise. The reaction was stirred for 30 minutes before N-Phenylbis(trifluoromethanesulfonamide) (40.03 g, 112.1 mmol) was added. The reaction was left to warm to room temperature overnight. The reaction was cooled to 0° C. and quenched with IPA followed by water. The solution was diluted with ethyl acetate/heptanes (1:1) and aqueous ammonia (30%, 400 mL) added. The phases were separated and the organic phase washed with aqueous ammonia (15%) twice before being washed with brine, dried over MgSO$_4$ and concentrated under reduced pressure. The residue was purified by silica chromatography eluted with a gradient from 2.5-10% methanol/dichloromethane to give (4bS,8aR,9R)-3-(benzyloxy)-11-methyl-6-oxo-6,7,8,8a,9,10-hexahydro-5H-9,4b-(epiminoethano)phenanthren-4-yl trifluoromethanesulfonate (31.6 g, 81% pure LCMS, 67% yield); [M+H]$^+$ 510.2.

Synthesis of (4bS,8aR,9R)-3-(benzyloxy)-11-methyl-8,8a,9,10-tetrahydro-5H-9,4b-(epiminoethano)phenanthren-6(7H)-one

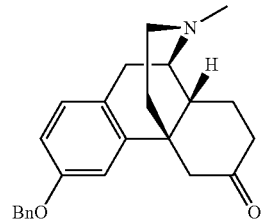

To a solution of (4bS,8aR,9R)-3-(benzyloxy)-11-methyl-6-oxo-6,7,8,8a,9,10-hexahydro-5H-9,4b-(epiminoethano)phenanthren-4-yltrifluoromethanesulfonate (31.9 g, 62.6 mmol) in degassed dimethylformamide (320 mL) was added Pd(OAc)$_2$ (1.405 g, 6.6 mmol), 1,3-bis(diphenylphosphino)propane (2.58 g, 6.3 mmol) and triethylsilane (100 mL, 626.0 mmol). The reaction was heated to 86° C. under argon for 4 hours. The reaction was cooled to room temperature, quenched with 2M HCl and extracted with diethyl ether: ethyl acetate (1:1). The organic phase was washed with 2M HCl. The acid phases were combined and washed with diethyl ether:ethyl acetate (1:1) (×3). The aqueous phase was basified with 2M NaOH and extracted with ethyl acetate (×3). The organic phase was washed with water (×3) and then brine before being dried over MgSO$_4$ and concentrated under reduced pressure to give (4bS,8aR,9R)-3-(benzyloxy)-11-methyl-8,8a,9,10-tetrahydro-5H-9,4b-(epiminoethano) phenanthren-6(7H)-one (20.2 g, 85% pure LCMS); [M+H]$^+$ 362.3. This was taken onto the next step without purification.

Synthesis of (4bS,8aR,9R)-3-(benzyloxy)-11-methyl-5,7,8,8a,9,10-hexahydrospiro[9,4b-(epiminoethano)phenanthrene-6,2'-[1,3]dioxolane]

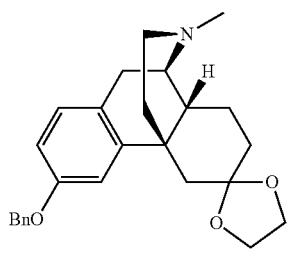

To a suspension of (4bS,8aR,9R)-3-(benzyloxy)-11-methyl-8,8a,9,10-tetrahydro-5H-9,4b-(epiminoethano)phenanthren-6(7H)-one (20.2 g, 55.9 mmol) in ethylene glycol (280 mL) was added methane sulfonic acid (14.5 mL, 223.5 mmol). The reaction went into solution and was stirred at room temperature for 16 hours. The reaction was poured into aqueous ammonia/ice and was extracted with ethyl acetate (×3). The organics were combined, washed with water/brine (×3) and dried over MgSO$_4$ and concentrated under reduced pressure to give (4bS,8aR,9R)-3-(benzyloxy)-11-methyl-5,7,8,8a,9,10-hexahydrospiro[9,4b-(epiminoethano)phenanthrene-6,2'-[1,3]dioxolane](18.6 g, 84% pure UPLC); [M+H]$^+$ 406.3. This was taken onto the next step without purification.

Synthesis of (4bS,8aR,9R)-11-methyl-5,7,8,8a,9,10-hexahydrospiro[9,4b-(epiminoethano)phenanthrene-6,2'-[1,3]dioxolan]-3-ol

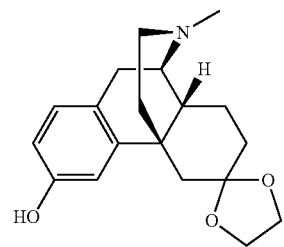

To a solution of (4bS,8aR,9R)-3-(benzyloxy)-11-methyl-5,7,8,8a,9,10-hexahydrospiro[9,4b-(epiminoethano)phenanthrene-6,2'-[1,3]dioxolane](21.8 g, 53.8 mmol) in ethanol (545 mL) was added 10% palladium on carbon (2.2 g, 0.1 eq by weight) and the reaction placed under an atmosphere of hydrogen. The reaction was stirred for 16 hours at room temperature. The reaction was filtered through a pad of celite and the filtrate concentrated under reduced pressure to give (4bS,8aR,9R)-11-methyl-5,7,8,8a,9,10-hexahydrospiro[9,4b-(epiminoethano)phenanthrene-6,2'-[1,3]dioxolan]-3-ol (16.9 g, 73% pure LCMS); [M+H+H]316.2. This was taken onto the next step without purification.

Synthesis of (4bS,8aR,9R)-11-methyl-5,7,8,8a,9,10-hexahydrospiro[9,4b-(epiminoethano)phenanthrene-6,2'-[1,3]dioxolan]-3-yl trifluoromethanesulfonate

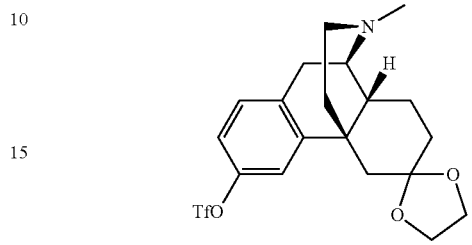

To a mixture of (4bS,8aR,9R)-11-methyl-5,7,8,8a,9,10-hexahydrospiro[9,4b-(epiminoethano)phenanthrene-6,2'-[1,3]dioxolan]-3-ol (16.95 g, 53.7 mmol) and triethylamine (22.5 mL, 161.2 mmol) in dichloromethane (400 mL) was added N-Phenylbis(trifluoromethanesulfonamide) (19.77 g, 55.4 mmol) and the mixture stirred at room temperature overnight. The solvent was concentrated under reduced pressure and the residue taken up in ethyl acetate. The organic phase was washed with aqueous ammonia/water (1:1×3) before washing with brine. The organic phase was dried over MgSO$_4$ and concentrated under reduced pressure. The residue was purified by silica chromatography eluted with 0-10% methanol in dichloromethane to give (4bS,8aR,9R)-11-methyl-5,7,8,8a,9,10-hexahydrospiro[9,4b-(epiminoethano)phenanthrene-6,2'-[1,3]dioxolan]-3-yl trifluoromethanesulfonate (18.7 g, 76.8% pure LCMS, 57.7% over 4 steps,); [M+H+H]$^+$ 448.2.

Synthesis of (4bS,8aR,9R)-11-methyl-5,7,8,8a,9,10-hexahydrospiro[9,4b-(epiminoethano)phenanthrene-6,2'-[1,3]dioxolane]-3-carbonitrile

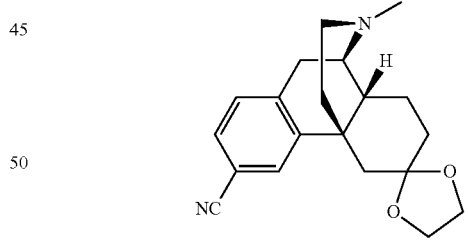

To a solution of (4bS,8aR,9R)-11-methyl-5,7,8,8a,9,10-hexahydrospiro[9,4b-(epiminoethano)phenanthrene-6,2'-[1,3]dioxolan]-3-yl trifluoromethanesulfonate (18.7 g, 41.8 mmol) in degassed dimethylformamide (250 mL) was added tetrakis(triphenylphosphine)palladium(0) (4.83 g, 4.2 mmol). After heating to 40° C., zinc cyanide (2.94 g, 25.0 mmol) was added and the reaction mixture heated at 130° C. for 24 hours. Reaction incomplete so cooled to room temperature and tetrakis(triphenylphosphine)palladium(0) (4.83 g, 4.2 mmol) was added and the reaction heated to 135° C. for 4 hours. The reaction mixture was cooled to room temperature and diluted with ethyl acetate and quenched with sodium hydrogen carbonate solution. The mixture was filtered through a pad of celite. The phases were separated and the product extracted with ethyl acetate (×3). The organic phases were combined, washed with water/brine (×3), dried over MgSO$_4$ and concentrated under reduced pressure. Purification by silica chromatography (100% dichloromethane to 5% NH$_3$/methanol in dichloromethane) gave (4bS,8aR,9R)-11-methyl-5,7,8,8a,9,10-hexahydrospiro[9,4b-(epiminoethano)phenanthrene-6,2'-[1,3]dioxolane]-3-carbonitrile (8.26 g, 89% pure LCMS). [M+H]$^+$ 325.2.

Synthesis of (4bS,8aR,9R)-5,7,8,8a,9,10-hexahydrospiro[9,4b-(epiminoethano)phenanthrene-6,2'-[1,3]dioxolane]-3-carbonitrile

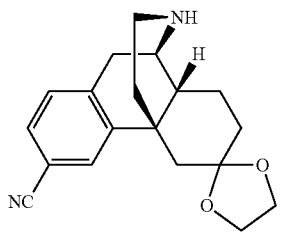

To a suspension of (4bS,8aR,9R)-11-methyl-5,7,8,8a,9,10-hexahydrospiro[9,4b-(epiminoethano)phenanthrene-6,2'-[1,3]dioxolane]-3-carbonitrile (8.26 g, 25.5 mmol) in dimethylformamide (65 mL) was added diisopropyl azodicarboxylate (9.32 mL, 47.4 mmol). The reaction was heated to 55° C. for 4 hours until starting material is consumed. To the reaction was added dimedone (9.99 g, 71.3 mmol) and methanol (3.1 mL, 94.2 mmol) and the reaction heated to 60° C. for 3 hours. The reaction was allowed to cool to room temperature overnight. The reaction was poured into 0.5 M HCl$_{(aq)}$ (250 mL) and washed with diethyl ether: ethyl acetate (3:1). The organic phase was back extracted with 0.5 M HCl$_{(aq)}$ (250 mL) and the acidic phases combined before basifying with 2M NaOH until pH9. The aqueous phase was extracted with ethyl acetate (×3). The combined organic phases were washed with water/brine (×3) before drying over MgSO$_4$ and concentrating under reduced pressure. The residue was purified by silica chromatography (100% dichloromethane to 10% NH$_3$/methanol in dichloromethane) to give (4bS,8aR,9R)-5,7,8,8a,9,10-hexahydrospiro[9,4b-(epiminoethano)phenanthrene-6,2'-[1,3]dioxolane]-3-carbonitrile (5.95 g, 42% yield over two steps, 92% pure LCMS); [M+H]$^+$ 311.2.

A1. Experimental Procedure for Compound A and a Hydrochloride Salt Thereof

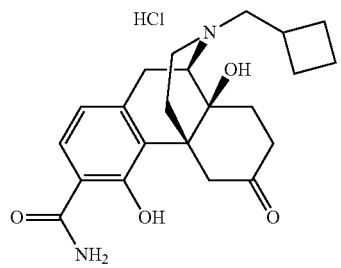

Chemical Formula: C$_{22}$H$_{29}$ClN$_2$O$_4$
Exact Mass: 420.18
Molecular Weight: 420.93

2-Cyclobutanecarbaldehyde

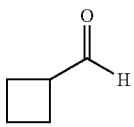

Chemical Formula: C$_5$H$_8$O
Exact Mass: 84.06
Molecular Weight: 84.12

To a mixture of Pyridinium chlorochromate (41.3 g, 191.6 mmol) in dichloromethane (120 mL) was added Cyclobutanemethanol (7.5 g, 87.1 mmol). The mixture was stirred for 1.5 hours then filtered through a pad of silica and rinsed with further dichloromethane (300 mL). The solvent was removed under reduced pressure to give 2-cyclobutylcarbaldehyde (10.0 g, contains residual dichloromethane) that was used without further purification.

(4R,4aS,7aR,12bS)-3-(cyclobutylmethyl)-4a,9-dihydroxy-2,3,4,4a,5,6-hexahydro-1H-4,12-methanobenzofuro[3,2-e]isoquinolin-7(7aH)-one

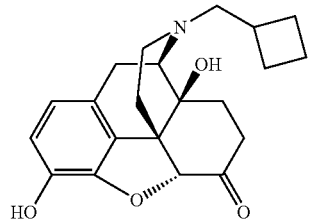

Chemical Formula: C$_{21}$H$_{25}$NO$_4$
Exact Mass: 355.18
Molecular Weight: 355.43

A mixture of Noroxymorphone (8.8 g, 30.6 mmol) in methanol (250 mL) was degassed for 20 minutes. 2-cyclobutanecarbaldehyde (7.7 g, 91.5 mmol) was added and the mixture heated at reflux for 1 hour. The reaction mixture was cooled to ambient temperature. In a separate flask formic acid (14.0 g, 306 mmol) was added slowly to a solution of triethylamine (12.4 g, 123 mmol) in methanol (40 mL). The formic acid solution was stirred for 5 minutes before being added to the solution containing Noroxymorphone along with dichloro(p-cymene)ruthenium(II) dimer (53 mg). The reaction was heated at reflux for a further 2.5 hours. The reaction was concentrated under reduced pressure then partitioned between ethyl acetate and saturated sodium bicarbonate solution. The aqueous phase was extracted with further ethyl acetate then the organic layers combined and dried (MgSO$_4$). Filtration and removal of the solvent under reduced pressure gave (4R,4aS,7aR,12bS)-3-(cyclobutylmethyl)-4a,9-dihydroxy-2,3,4,4a,5,6-hexahydro-1H-4,12-methanobenzofuro[3,2-e]isoquinolin-7(7aH)-one (10.2 g, 94% yield); LC/MS (M+H)$^+$=356.2.

(4R,4aS,7aR,12bS)-3-(cyclobutylmethyl)-4a-hydroxy-7-oxo-2,3,4,4a,5,6,7,7a-octahydro-1H-4,12-methanobenzofuro[3,2-e]isoquinolin-9-yl trifluoromethanesulfonate

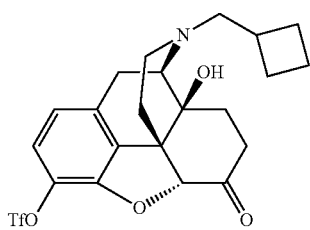

Chemical Formula: C₂₂H₂₄F₃NO₆S
Exact Mass: 487.13
Molecular Weight: 487.49

To a solution of (4R,4aS,7aR,12bS)-3-(cyclobutylmethyl)-4a,9-dihydroxy-2,3,4,4a,5,6-hexahydro-1H-4,12-methanobenzofuro[3,2-e]isoquinolin-7(7aH)-one (10.2 g, 28.7 mmol) and triethylamine (12.2 mL, 88.3 mmol) in dichloromethane (200 mL) was added N-Phenylbis(trifluoromethanesulfonamide) (11.0 g, 30.9 mmol) and the mixture stirred at room temperature overnight. The solvent was concentrated under reduced pressure and the residue partitioned between 20% hexane in ethyl acetate (500 mL) and water (300 mL). The organic layer was washed twice more with water and dried (MgSO₄). Filtration and removal of the solvent under reduced pressure gave (4R,4aS,7aR,12bS)-3-(cyclobutylmethyl)-4a-hydroxy-7-oxo-2,3,4,4a,5,6,7,7a-octahydro-1H-4,12-methanobenzofuro[3,2-e]isoquinolin-9-yl trifluoromethanesulfonate (14.3 g, 100% yield); LC/MS (M+H)⁺=488.1.

(4R,4aS,7aR,12bS)-3-(cyclobutylmethyl)-N-(2,4-dimethoxybenzyl)-4a-hydroxy-7-oxo-2,3,4,4a,5,6,7,7a-octahydro-1H-4,12-methanobenzofuro[3,2-e]isoquinoline-9-carboxamide

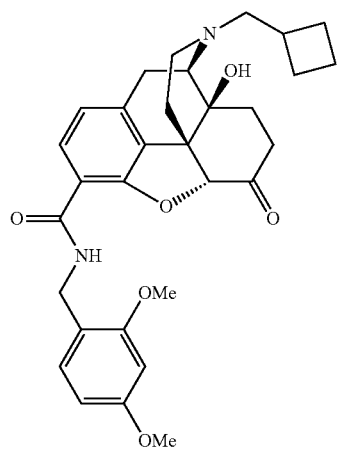

Chemical Formula: C₃₁H₃₆N₂O₆
Exact Mass: 532.26
Molecular Weight: 532.63

To a solution of (4R,4aS,7aR,12bS)-3-(cyclobutylmethyl)-4a-hydroxy-7-oxo-2,3,4,4a,5,6,7,7a-octahydro-1H-4,12-methanobenzofuro[3,2-e]isoquinolin-9-yl trifluoromethanesulfonate (14.3 g, 29.3 mmol) in degassed dimethyl sulfoxide (185 mL), was added N-hydroxysuccinimide (6.8 g, 58.7 mmol), palladium acetate (0.66 g, 2.93 mmol), triethylamine (8.2 mL, 58.7 mmol) and 4,5-bis(diphenylphosphino)-9,9-dimethylxanthene (1.7 g, 2.93 mmol). The reaction mixture was heated with carbon monoxide (1 atm) at 75° C. overnight. The reaction mixture was cooled to ambient temperature and 2,4-dimethoxybenzylamine (4.9 g, 29.3 mmol) added. The mixture was stirred for 1 hour before partitioning between water (2 L) and ethyl acetate (1 L). The aqueous phase was extracted twice more with ethyl acetate. The combined organic phase was dried (MgSO₄), filtered, and the solvent removed under reduced pressure. The crude material was purified by silica chromatography (3% methanol in dichloromethane) to give (4R,4aS,7aR,12bS)-3-(cyclobutylmethyl)-N-(2,4-dimethoxybenzyl)-4a-hydroxy-7-oxo-2,3,4,4a,5,6,7,7a-octahydro-1H-4,12-methanobenzofuro[3,2-e]isoquinoline-9-carboxamide (14.4 g, 55% yield); LC/MS (M+H)⁺=533.3.

(4R,4aS,7aR,12bS)-3-(cyclobutylmethyl)-4a-hydroxy-7-oxo-2,3,4,4a,5,6,7,7a-octahydro-1H-4,12-methanobenzofuro[3,2-e]isoquinoline-9-carboxamide

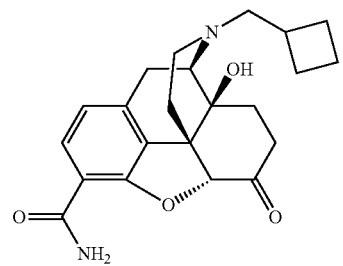

Chemical Formula: C₂₂H₂₆N₂O₄
Exact Mass: 382.19
Molecular Weight: 382.45

A mixture of (4R,4aS,7aR,12bS)-3-(cyclobutylmethyl)-N-(2,4-dimethoxybenzyl)-4a-hydroxy-7-oxo-2,3,4,4a,5,6,7,7a-octahydro-1H-4,12-methanobenzofuro[3,2-e]isoquinoline-9-carboxamide (14.4 g, 27.0 mmol) in trifluoroacetic acid was stirred at ambient temperature for 2 hours. The trifluoroacetic acid was removed under reduced pressure and the residue quenched with 300 mL of ammonium hydroxide (6%). The product was extracted twice into dichloromethane (300 mL), the organic phases combined and dried (MgSO₄). Filtration and removal of to the solvent under reduced pressure gave (4R,4aS,7aR,12bS)-3-(cyclobutylmethyl)-4a-hydroxy-7-oxo-2,3,4,4a,5,6,7,7a-octahydro-1H-4,12-methanobenzofuro[3,2-e]isoquinoline-9-carboxamide (9.0 g, 87% yield); LC/MS (M+H)⁺=383.2.

(4bR,8aS,9R)-11-(cyclobutylmethyl)-4,8a-dihydroxy-6-oxo-6,7,8,8a,9,10-hexahydro-5H-9,4b-(epiminoethano)phenanthrene-3-carboxamide (Compound A)

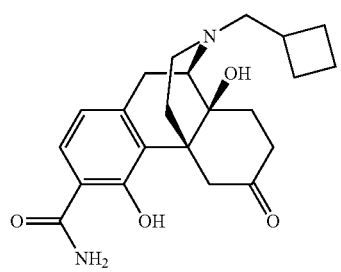

Chemical Formula: $C_{22}H_{28}N_2O_4$
Exact Mass: 384.20
Molecular Weight: 384.47

To a mixture of (4R,4aS,7aR,12bS)-3-(cyclobutylmethyl)-4a-hydroxy-7-oxo-2,3,4,4a,5,6,7,7a-octahydro-1H-4,12-methanobenzofuro[3,2-e]isoquinoline-9-carboxamide (4.5 g, 11.8 mmol), and zinc powder (29.0 g, 444 mmol) in acetic acid (135 mL) was added conc. HCl (25.5 mL). The mixture was heated to 125° C. for 2 hours. The reaction mixture was cooled to ambient temperature and quenched into ice/ammonium hydroxide solution (1 L, 28%). The product was extracted into dichloromethane (1 L) and dried ($MgSO_4$). Filtration and removal of the solvent under reduced pressure gave the crude material which was purified by silica chromatography (7.5% methanol/ammonia in DCM) followed by recrystallisation from methanol to give (4bR,8aS,9R)-11-(cyclobutylmethyl)-4,8a-dihydroxy-6-oxo-6,7,8,8a,9,10-hexahydro-5H-9,4b-(epiminoethano)phenanthrene-3-carboxamide (2.1 g, 46% yield); LC/MS $(M+H)^+$=385.2.

(4bR,8aS,9R)-11-(cyclobutylmethyl)-4,8a-dihydroxy-6-oxo-6,7,8,8a,9,10-hexahydro-5H-9,4b-(epiminoethano)phenanthrene-3-carboxamide hydrochloride

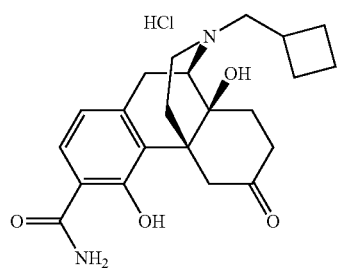

Chemical Formula: $C_{22}H_{29}ClN_2O_4$
Exact Mass: 420.18
Molecular Weight: 420.93

To a solution of (4bR,8aS,9R)-11-(cyclobutylmethyl)-4,8a-dihydroxy-6-oxo-6,7,8,8a,9,10-hexahydro-5H-9,4b-(epiminoethano)phenanthrene-3-carboxamide (2.1 g, 5.46 mmol) in ethyl acetate (100 mL) was added 2N HCl/ether (6 mL, 12 mmol) and the mixture stirred for 4 hours. The solvent was removed under reduced pressure and dried (55° C.) giving (4bR,8aS,9R)-11-(cyclobutylmethyl)-4,8a-dihydroxy-6-oxo-6,7,8,8a,9,10-hexahydro-5H-9,4b-(epiminoethano)phenanthrene-3-carboxamide hydrochloride (2.25 g, 98% yield); LC/MS $(M+H)^+$=385.2. $^1$H-NMR (400 MHz, DMSO) δ 8.98 (br s, 1H), 8.45 (s, 1H), 7.96 (s, 1H), 7.68 (d, 1H), 6.64 (d, 1H), 6.33 (s, 1H), 3.85 (d, 1H), 3.45 (br s, 1H), 3.29 (br s, 3H+$H_2O$), 3.15-2.91 (m, 2H), 2.74-2.60 (m, 3H), 2.40-2.10 (m, 2H), 2.12-1.55 (m, 10H).

A2. Experimental Procedure for Compound D and a Hydrochloride Salt Thereof

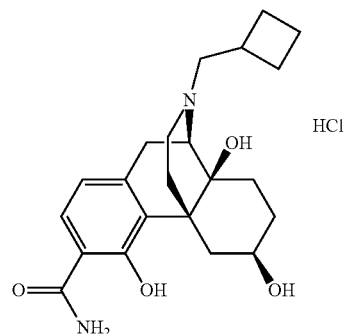

Chemical Formula: $C_{22}H_{31}ClN_2O_4$
Exact Mass: 422.20
Molecular Weight: 422.95

(4bR,6R,8aS,9R)-11-(cyclobutylmethyl)-4,6,8a-trihydroxy-6,7,8,8a,9,10-hexahydro-5H-9,4b-(epiminoethano)phenanthrene-3-carboxamide (Compound D)

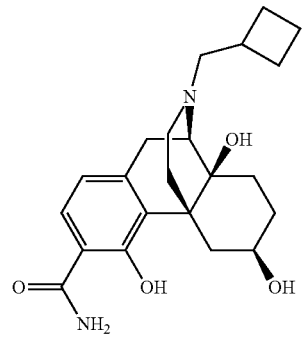

Chemical Formula: $C_{22}H_{30}N_2O_4$
Exact Mass: 386.22
Molecular Weight: 386.48

A solution of formamidinesulfinic acid (1.12 g, 10.4 mmol, 4.00 eq.) in 0.5 M aqueous sodium hydroxide (20 mL) was added dropwise over 10 minutes to a stirred to solution of (4bR,8aS,9R)-11-(cyclobutylmethyl)-4,8a-dihydroxy-6-oxo-6,7,8,8a,9,10-hexahydro-5H-9,4b-(epiminoethano)phenanthrene-3-carboxamide (1.00 g, 2.60 mmol, 1.00 eq.) in 0.5 N NaOH$_{(aq)}$ (30 mL) at ambient temperature under argon. The mixture was heated to 80° C. under argon for 12 hours and then cooled to room temperature. The precipitated solid was collected by filtration and then washed with water (2×10 mL) and diethyl ether (2×20 mL). The solid was recrystallised in methanol and then dried at 50° C. under vacuum for 3 hours to leave (4bR,6R,8aS,9R)-11-(cyclobutylmethyl)-4,6,8a-trihydroxy-6,7,8,8a,9,10-hexahydro-5H-9,4b-(epiminoethano)phenanthrene-3-carboxamide as colourless crystals (400 mg, 40% yield); LC/MS $(M+H)^+$=387.26.

63

(4bR,6R,8aS,9R)-11-(cyclobutylmethyl)-4,6,8a-trihydroxy-6,7,8,8a,9,10-hexahydro-5H-9,4b-(epiminoethano)phenanthrene-3-carboxamide hydrochloride

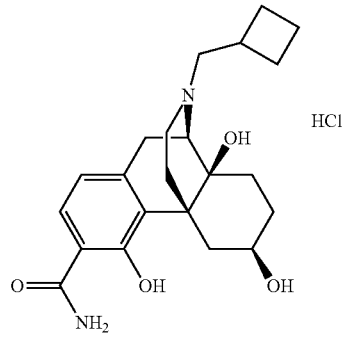

Chemical Formula: $C_{22}H_{31}ClN_2O_4$
Exact Mass: 422.20
Molecular Weight: 422.95

A solution of hydrochloric acid (0.40 mL, 2.0 M in diethyl ether) was added dropwise over 5 minutes to a stirred solution of (4bR,6R,8aS,9R)-11-(cyclobutylmethyl)-4,6,8a-trihydroxy-6,7,8,8a,9,10-hexahydro-5H-9,4b-(epiminoethano) phenanthrene-3-carboxamide (400 mg, 1.03 mmol, 1.00 eq.) in ethyl acetate (4 mL) at ambient temperature under argon. The mixture was stirred at ambient temperature under argon for 3 hours and then concentrated under reduced pressure. The solid was dried at 50° C. under vacuum for 1 hour, and then freeze dried to leave (4bR,6R,8aS,9R)-11-(cyclobutylmethyl)-4,6,8a-trihydroxy-6,7,8,8a,9,10-hexahydro-5H-9,4b-(epiminoethano)phenanthrene-3-carboxamide hydrochloride as a colourless solid (379 mg, 87%); LC/MS (M+H)$^+$ =387.26. $^1$H NMR (300 MHz, CDCl3, 614-181-1_1H-1.jdf): 14.43 (s, 1H), 8.80 (br. s, 1H), 8.47 (s, 1H), 7.95 (s, 1H), 7.69 (d, J=8.3 Hz, 1H), 6.63 (d, J=8.3 Hz, 1H), 5.69 (s, 1H), 4.45 (s, 1H), 3.31-3.08 (m, 6H), 3.00-2.81 (m, 2H), 2.70-2.57 (m, 1H), 2.40-2.23 (m, 1H), 2.17-1.91 (m, 3H), 1.90-1.70 (m, 4H), 1.67-1.31 (m, 6H).

A3. Experimental Procedure for Compound C and a Hydrochloride Salt Thereof

64

(4bR,6S,8aS,9R)-11-(cyclobutylmethyl)-4,6,8a-trihydroxy-6,7,8,8a,9,10-hexahydro-5H-9,4b-(epiminoethano)phenanthrene-3-carboxamide (Compound C)

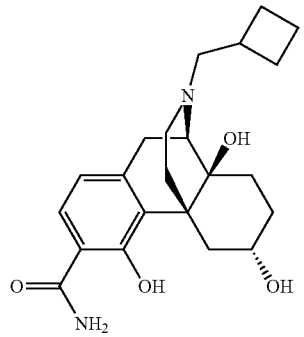

Chemical Formula: $C_{22}H_{30}N_2O_4$
Exact Mass: 386.22
Molecular Weight: 386.48

A solution of K-selectride (7.80 mL, 7.80 mmol, 3.00 eq., 1.0 M in tetrahydrofuran) was added dropwise over 15 minutes to a stirred solution of (4bR,8aS,9R)-11-(cyclobutylmethyl)-4,8a-dihydroxy-6-oxo-6,7,8,8a,9,10-hexahydro-5H-9,4b-(epiminoethano) phenanthrene-3-carboxamide (1.00 g, 2.60 mmol, 1.00 eq.) in tetrahydrofuran (50 mL) at 0° C. under argon. The mixture was stirred at 0° C. under argon for 2 hours and then water (20 mL) and methanol (50 mL) were carefully added dropwise over 15 minutes. The mixture was neutralised to pH 7 by addition of 2N HCl$_{(aq)}$. The mixture was concentrated under reduced pressure and the solid residue recrystallised in methanol. The solid was washed with methanol (4 mL) and diethyl ether (2×10 mL), and then dried at 50° C. under vacuum for 3 hours to leave (4bR,6S,8aS,9R)-11-(cyclobutylmethyl)-4,6,8a-trihydroxy-6,7,8,8a,9,10-hexahydro-5H-9,4b-(epiminoethano)phenanthrene-3-carboxamide as colourless crystals (750 mg, 74%); LC/MS (M+H)$^+$=387.3.

(4bR,6S,8aS,9R)-11-(cyclobutylmethyl)-4,6,8a-trihydroxy-6,7,8,8a,9,10-hexahydro-5H-9,4b-(epiminoethano)phenanthrene-3-carboxamide hydrochloride

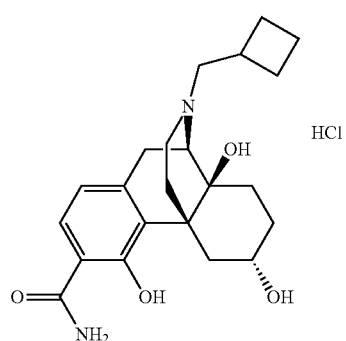

Chemical Formula: $C_{22}H_{31}ClN_2O_4$
Exact Mass: 422.20
Molecular Weight: 422.95

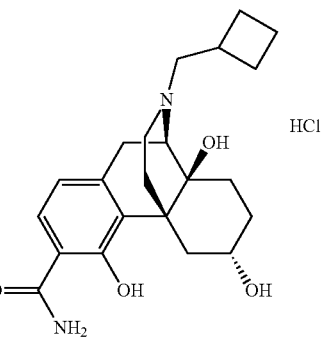

Chemical Formula: $C_{22}H_{31}ClN_2O_4$
Exact Mass: 422.20
Molecular Weight: 422.95

A solution of hydrochloric acid (0.75 mL, 2.0 M in diethyl ether) was added dropwise over 5 minutes to a stirred solution of (4bR,6S,8aS,9R)-11-(cyclobutylmethyl)-4,6,8a-trihydroxy-6,7,8,8a,9,10-hexahydro-5H-9,4b-(epiminoethano)phenanthrene-3-carboxamide (750 mg, 1.94 mmol) in ethyl acetate (10 mL) at ambient temperature under argon. The mixture was stirred at ambient temperature under argon for 3 hours and then concentrated under reduced pressure. The solid was triturated with diethyl ether (2×10 mL), dried at 50° C. under vacuum for 1 hour, then freeze dried to leave (4bR,6S,8aS,9R)-11-(cyclobutylmethyl)-4,6,8a-trihydroxy-6,7,8,8a,9,10-hexahydro-5H-9,4b-(epiminoethano)phenanthrene-3-carboxamide hydrochloride as a colourless solid (695 mg, 85% yield); LC/MS (M+H)$^+$=387.3. $^1$H NMR (300 MHz, DMSO): δ 14.26 (s, 1H), 8.82 (br. s, 1H), 8.36 (s, 1H), 7.79 (s, 1H), 7.60 (d, J=8.3 Hz, 1H), 6.56 (d, J=8.3 Hz, 1H), 5.63 (s, 1H), 3.83 (s, 1H), 3.63 (s, 1H), 3.49-3.36 (m, 1H), 3.29-3.08 (m, 4H), 2.97-2.80 (m, 2H), 2.72-2.58 (m, 1H), 2.36-2.20 (m, 1H), 2.14-1.70 (m, 9H), 1.68-1.49 (m, 2H), 1.38-1.22 (m, 2H).

A4. Experimental Procedure for

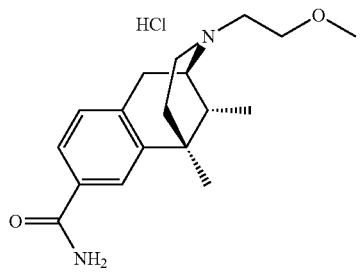

Chemical Formula: C$_{18}$H$_{27}$ClN$_2$O$_2$
Exact Mass: 338.18
Molecular Weight: 338.87

(2R,6R,11R)-tert-butyl-8-hydroxy-6,11-dimethyl-1,2,5,6-tetrahydro-2,6-methanobenzo[d]azocine-3(4H)-carboxylate

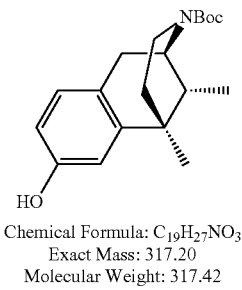

Chemical Formula: C$_{19}$H$_{27}$NO$_3$
Exact Mass: 317.20
Molecular Weight: 317.42

A mixture of (−)-Normetazocine (5.0 g, 23.0 mmol), di-tert-butyl dicarbonate to (7.53 g, 34.5 mmol), and sodium hydrogen carbonate (5.80 g, 69.0 mmol), in dichloromethane (170 mL), tetrahydrofuran (170 mL), methanol (85 mL) and water (500 mL) was stirred at ambient temperature overnight. The organic phase was separated and the aqueous phase washed twice with dichloromethane (500 mL). The combined organic phases were dried (MgSO$_4$). Filtration and removal of the solvent under reduced pressure gave oil that was dissolved in industrial methylated spirits (250 mL) and stirred with imidazole (3.0 g, 44.1 mmol) for 1 hour. The solvent was removed under reduced pressure and the residue partitioned between dichloromethane (250 mL) and 0.5N HCl$_{(aq)}$ (250 mL). The organic phase was washed with further acid (250 mL), brine (100 mL), and dried (MgSO$_4$). Filtration and removal of the solvent under reduced pressure gave (2R,6R,11R)-tert-butyl 8-hydroxy-6,11-dimethyl-1,2,5,6-tetrahydro-2,6-methanobenzo[d]azocine-3(4H)-carboxylate (3.9 g, 53% yield); LC/MS (M+H)$^+$=318.5.

(2R,6R,11R)-tert-butyl 6,11-dimethyl-8-(((trifluoromethyl)sulfonyl)oxy)-1,2,5,6-tetrahydro-2,6-methanobenzo[d]azocine-3(4H)-carboxylate

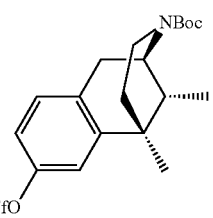

Chemical Formula: C$_{20}$H$_{26}$F$_3$NO$_5$S
Exact Mass: 449.15
Molecular Weight: 449.48

To a solution of (2R,6R,11R)-tert-butyl 8-hydroxy-6,11-dimethyl-1,2,5,6-tetrahydro-2,6-methanobenzo[d]azocine-3(4H)-carboxylate (3.9 g, 12.3 mmol) and triethylamine (5.1 mL, 36.9 mmol) in dichloromethane (100 mL) was added N-Phenylbis(trifluoromethanesulfonamide) (4.61 g, 12.9 mmol) and the mixture stirred to at ambient temperature for 4 hours. The solvent was concentrated under reduced pressure and the residue partitioned between 20% hexane in ethyl acetate (500 mL) and water (400 mL). The organic layer was washed four more times more with water and dried (MgSO$_4$). Filtration and removal of the solvent under reduced pressure gave (2R,6R,11R)-tert-butyl 6,11-dimethyl-8-(((trifluoromethyl)sulfonyl)oxy)-1,2,5,6-tetrahydro-2,6-methanobenzo[d]azocine-3(4H)-carboxylate (5.32 g, 96% yield); LC/MS (M+H)$^+$=450.4.

(2R,6R,11R)-tert-butyl 8-((2,4-dimethoxybenzyl)carbamoyl)-6,11-dimethyl-1,2,5,6-tetrahydro-2,6-methanobenzo[d]azocine-3(4H)-carboxylate

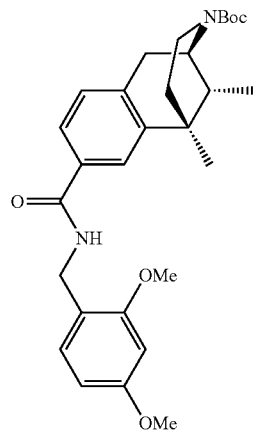

Chemical Formula: C$_{29}$H$_{33}$N$_2$O$_5$
Exact Mass: 494.28
Molecular Weight: 494.62

To a solution of (2R,6R,11R)-tert-butyl 6,11-dimethyl-8-(((trifluoromethyl)sulfonyl)oxy)-1,2,5,6-tetrahydro-2,6-methanobenzo[d]azocine-3(4H)-carboxylate (5.32 g, 11.8 mmol) in degassed dimethyl sulfone (50 mL), was added N-hydroxysuccinimide (2.73 g, 23.7 mmol), palladium acetate (265 mg, 1.18 mmol), triethylamine (3.3 mL, 23.7 mmol) and 4,5-bis(diphenylphosphino)-9,9-dimethylxanthene (683 mg, 1.18 mmol). The reaction mixture was heated with carbon monoxide (1 atm) at 70° C. overnight. The reaction mixture was cooled to ambient temperature and 2,4-dimethoxybenzylamine (2.17 mg, 13.0 mmol) added. The mixture was stirred for 2 hours diluted with ethyl acetate (800 mL), and filtered through celite. The organic solution was washed twice with water (800 mL), brine (300 mL), and dried (MgSO$_4$). Filtration and removal of the solvent under reduced pressure gave crude material that was purified by silica chromatography (EtOAc(1):heptanes(1)) to give (2R,6R,11R)-tert-butyl 84(2,4-dimethoxybenzyl)carbamoyl)-6,11-dimethyl-1,2,5,6-tetrahydro-2,6-methanobenzo[d]azocine-3(4H)-carboxylate (4.0 g, 68% yield); LC/MS(M+H)$^+$=495.3.

(2R,6R,11R)-N-(2,4-dimethoxybenzyl)-6,11-dimethyl-1,2,3,4,5,6-hexahydro-2,6-methanobenzo[d]azocine-8-carboxamide hydrochloride

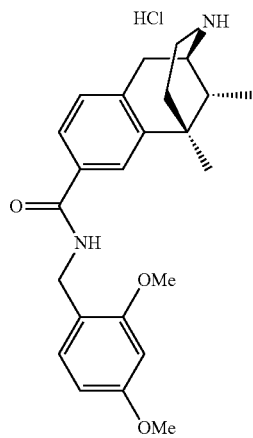

Chemical Formula: C$_{24}$H$_{31}$ClN$_2$O$_3$
Exact Mass: 430.20
Molecular Weight: 430.97

A mixture of (2R,6R,11R)-tert-butyl 8-((2,4-dimethoxybenzyl)carbamoyl)-6,11-dimethyl-1,2,5,6-tetrahydro-2,6-methanobenzo[d]azocine-3(4H)-carboxylate (4.00 g, 8.09 mmol) in 4N HCl/dioxane was stirred at ambient temperature overnight. The majority of the solvent was decanted and the residue washed with diethyl ether (500 mL). The resulting solid was dried under reduced pressure giving (2R,6R,11R)-N-(2,4-dimethoxybenzyl)-6,11-dimethyl-1,2,3,4,5,6-hexahydro-2,6-methanobenzo[d]azocine-8-carboxamide hydrochloride (3.35 g, 96% yield); LC/MS (M+H)$^+$=395.5.

(2R,6R,11R)-N-(2,4-dimethoxybenzyl)-3-(2-methoxyethyl)-6,11-dimethyl-1,2,3,4,5,6-hexahydro-2,6-methanobenzo[d]azocine-8-carboxamide

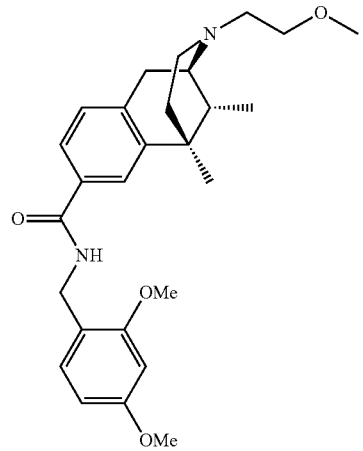

Chemical Formula: C$_{27}$H$_{36}$N$_2$O$_4$
Exact Mass: 452.27
Molecular Weight: 452.59

A mixture of 2R,6R,11R)-N-(2,4-dimethoxybenzyl)-6,11-dimethyl-1,2,3,4,5,6-hexahydro-2,6-methanobenzo[d]azocine-8-carboxamide hydrochloride (400 mg, 0.93 mmol), potassium carbonate (385 mg, 2.78 mmol), and bromoethyl methyl ether (142 mg, 1.02 mmol) in acetonitrile (15 mL) was heated at 65° C. overnight. Further bromoethyl methyl ether was added (70 mg, 0.50 mmol) and the to reaction heated at 65° C. for 24 hours. The reaction mixture was allowed to return to ambient temperature before partitioning between ethyl acetate (100 mL) and water (100 mL). The organic phase was dried (MgSO$_4$). Filtration and removal of the solvent under reduced pressure gave (2R,6R,11R)-N-(2,4-dimethoxybenzyl)-3-(2-methoxyethyl)-6,11-dimethyl-1,2,3,4,5,6-hexahydro-2,6-methanobenzo[d]azocine-8-carboxamide (360 mg, 86% yield); LC/MS (M+H)$^+$=453.2.

(2R,6R,11R)-3-(2-methoxyethyl)-6,11-dimethyl-1,2,3,4,5,6-hexahydro-2,6-methanobenzo[d]azocine-8-carboxamide

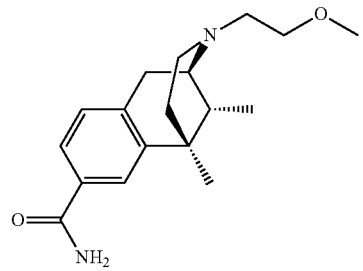

Chemical Formula: C$_{18}$H$_{26}$N$_2$O$_2$
Exact Mass: 302.20
Molecular Weight: 302.41

A mixture of (2R,6R,11R)-N-(2,4-dimethoxybenzyl)-3-(2-methoxyethyl)-6,11-dimethyl-1,2,3,4,5,6-hexahydro-2,6-methanobenzo[d]azocine-8-carboxamide (360 mg, 0.80 mmol) in trifluoroacetic acid (5 mL) was stirred at ambient temperature for 2 hours. The mixture was concentrated under reduced pressure before quenching with ice/ammonium hydroxide (28%) (25 mL). The crude product was extracted twice to using dichloromethane (100 mL) and the combined organic layers dried (MgSO$_4$). Filtration and removal of the solvent under reduced pressure gave the crude product that was purified by prep-HPLC giving (2R,6R,11R)-3-(2-methoxyethyl)-6,11-dimethyl-1,2,3,4,5,6-hexahydro-2,6-methanobenzo[d]azocine-8-carboxamide (130 mg, 54% yield); LC/MS (M+H)$^+$=303.2.

(2R,6R,11R)-3-(2-methoxyethyl)-6,11-dimethyl-1,2,3,4,5,6-hexahydro-2,6-methanobenzo[d]azocine-8-carboxamide hydrochloride

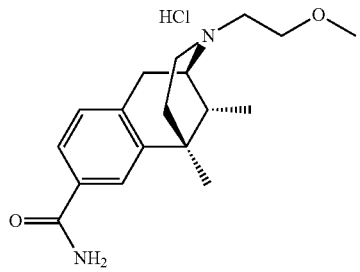

Chemical Formula: C$_{18}$H$_{27}$ClN$_2$O$_2$
Exact Mass: 338.18
Molecular Weight: 338.87

To a solution of (2R,6R,11R)-3-(2-methoxyethyl)-6,11-dimethyl-1,2,3,4,5,6-hexahydro-2,6-methanobenzo[d]azocine-8-carboxamide (130 mg, 0.43 mmol) in ethyl acetate (10 mL) was added 2N HCl/ether (320 μL, 0.64 mmol) and the mixture stirred for 1.5 hours. The solvent was removed under reduced pressure then freeze dried giving (2R,6R,11R)-3-(2-methoxyethyl)-6,11-dimethyl-1,2,3,4,5,6-hexahydro-2,6-methanobenzo[d]azocine-8-carboxamide hydrochloride (131 mg, 90% yield); LC/MS (M+H)$^+$=303.22. $^1$H-NMR (300 MHz, DMSO) δ 10.59-10.44 (br d, 1H), 7.96 (s, 1H), 7.78 (s, 1H), 7.68 (d, 1H), 7.31 (d, 1H), 7.20 (d, 1H), 3.84-3.49 (m, 3H), 3.49-2.95 (6H+H$_2$O), 2.43-2.20 (m, 2H), 2.16-1.97 (m, 2H), 1.54-1.23 (m, 2H), 0.87-0.66 (m, 3H).

A5. Experimental Procedure for Compound 1

(4bS,9R)-4-hydroxy-3-methoxy-11-methyl-8,8a,9,10-tetrahydro-5H-9,4b-(epiminoethano)phenanthren-6(7H)-one (A) and (4bR,9R)-3-methoxy-11-meth 6,7,8,8a,9,10-hexahydro-5H-9,4b-(epiminoethano) phenanthren-4-ol (B)

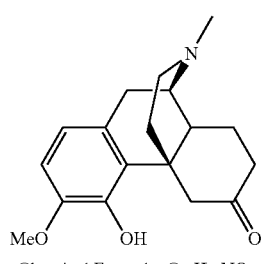

(A)

Chemical Formula: C$_{18}$H$_{23}$NO$_3$
Exact Mass: 301.17
Molecular Weight: 301.38

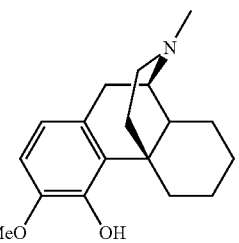

(B)

Chemical Formula: C$_{18}$H$_{25}$NO$_2$
Exact Mass: 287.19
Molecular Weight: 287.40

To a mixture of hydrocodone (2×22 g (2 batches), 147 mmol) and zinc powder (2×115 g, 3.46 mol) in acetic acid (2×1 L) was added conc. HCl (2×50 mL). The reaction was heated at 125° C. for 3 hours. Both reactions were combined and filtered. The zinc wash washed with industrial methylated spirits (1 L), and dichloromethane (1 L). Both organic washes and the acetic acid solution were concentrated under reduced pressure and the residue basified with ice/ammonium hydroxide (28%). The crude product was extracted into dichloromethane and dried (MgSO$_4$). Filtration and removal of the solvent under reduced pressure gave the crude products that were purified by silica chromatography (3% methanol/ammonia in dichloromethane) giving three batches of varying purity (2.4 g, (B); 20.5 g, 50% (A), 50% (B); 12.5 g, 65% (A), 10% (B)); LC/MS (M+H)$^+$=302.1 (A); LC/MS (M+H)$^+$=288.2 (B).

(4bS,9R)-3-methoxy-11-methyl-6-oxo-6,7,8,8a,9,10-hexahydro-5H-9,4b-(epiminoethano)phenanthren-4-yl trifluoromethanesulfonate (C) and (4bR,9R)-3-methoxy-11-methyl-6,7,8,8a,9,10-hexahydro-5H-9,4b-(epiminoethano)phenanthren-4-yl trifluoromethanesulfonate (D)

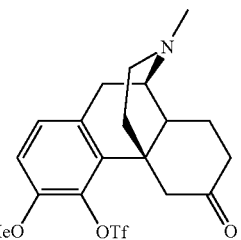

(C)

Chemical Formula: C$_{19}$H$_{22}$F$_3$NO$_5$S
Exact Mass: 433.12
Molecular Weight: 433.44

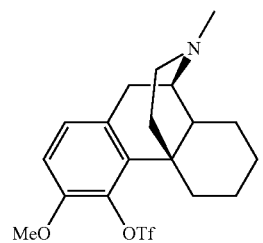

(D)

Chemical Formula: C$_{19}$H$_{24}$F$_3$NO$_4$S
Exact Mass: 419.14
Molecular Weight: 419.46

To a solution containing a (1:1) mixture of (4bS,9R)-4-hydroxy-3-methoxy-11-methyl-8,8a,9,10-tetrahydro-5H-9,4b-(epiminoethano)phenanthren-6(7H)-one (A) and (4bR,9R)-3-methoxy-11-methyl-6,7,8,8a,9,10-hexahydro-5H-9,4b-(epiminoethano)phenanthren-4-ol (B) (20.5 g, 69.4 mmol) in tetrahydrofuran at 0° C. under an argon atmosphere was added sodium hydride (4.18 g, 60% in mineral oil, 104.5 mmol). After 30 minutes N-Phenylbis(trifluoromethanesulfonamide) (37.3 g, 104.4 mmol) was added and the mixture allowed to slowly return to ambient temperature. The reaction was quenched with saturated aqueous sodium bicarbonate solution (500 mL) and extracted into ethyl acetate (1 L). The organic phase was washed with brine and dried ($MgSO_4$). Filtration and removal of the solvent under reduced pressure gave the crude product that was purified by silica chromatography (2.5% methanol/ammonia in dichloromethane) giving two batches of varying purity (11.0 g, (D); 15.1 g, 62% (C), 33% (D); LC/MS $(M+H)^+$=434.1 (C); LC/MS $(M+H)^+$=420.1 (D).

(4bR,9R)-3-methoxy-11-methyl-6,7,8,8a,9,10-hexahydro-5H-9,4b-(epiminoethano)phenanthrene

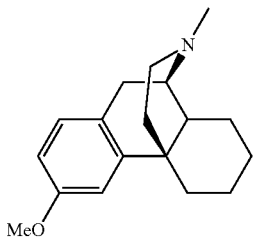

Chemical Formula: $C_{18}H_{25}NO$
Exact Mass: 271.19
Molecular Weight: 271.40

A mixture of (4bR,9R)-3-methoxy-11-methyl-6,7,8,8a,9,10-hexahydro-5H-9,4b-(epiminoethano)phenanthren-4-yl-trifluoromethanesulfonate (D) (11.0 g, 26.2 mmol), palladium acetate (590 mg, 2.63 mmol), 1,3-bis(diphenylphosphino)propane (1.08 g, 2.61 mmol) and triethylsilane (10.0 mL, 62.6 mmol) in dimethylformamide (degassed) was heated at 60° C. overnight under an argon atmosphere. The reaction to mixture was cooled to ambient temperature and partitioned between ethyl acetate (1 L) and water (1 L). The organic phase was washed twice more with water (2×500 mL). The combined aqueous phases were extracted using dichloromethane (2 L total). The organic phase containing dichloromethane and dimethyl formamide was concentrated under reduced pressure and the crude product purified by silica chromatography (3% methanol/ammonia in dichloromethane).

The same procedure was carried out with the 15.1 g batch (62% (C), 33% (D)). The material was purified as described above to give (4bR,9R)-3-methoxy-11-methyl-6,7,8,8a,9,10-hexahydro-5H-9,4b-(epiminoethano)phenanthrene (8.6 g); LC/MS $(M+H)^+$=272.0.

(4bR,9R)-3-methoxy-6,7,8,8a,9,10-hexahydro-5H-9,4b-(epiminoethano)phenanthrene

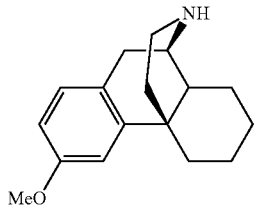

Chemical Formula: $C_{17}H_{23}NO$
Exact Mass: 257.18
Molecular Weight: 257.37

To a solution of (4bR,9R)-3-methoxy-11-methyl-6,7,8,8a,9,10-hexahydro-5H-9,4b-(epiminoethano)phenanthrene (5.0 g, 18.44 mmol) in dichloromethane (400 mL) was added a solution of CNBr (17 mL, 51 mmol, 3N in dichloromethane) under an argon atmosphere. The mixture was heated at reflux overnight. The solvent was removed under reduced pressure and to the residue was added diethyleneglycol (100 mL) and KOH (16.6 g, 296 mmol). The reaction mixture was heated at 160° C. for 2 hours, allowed to return to ambient temperature, then partitioned between dichloromethane (600 mL) and water (1 L). The aqueous phase was washed twice more with dichloromethane and the combined organic fractions dried ($MgSO_4$). Filtration and removal of the solvent under reduced pressure gave the crude product that was purified by silica chromatography (10% methanol/ammonia in DCM) giving (4bR,9R)-3-methoxy-6,7,8,8a,9,10-hexahydro-5H-9,4b-(epiminoethano)phenanthrene (4.02 g, 85% yield); LC/MS $(M+H)^+$=258.5.

(4b,9R)-11-(1-cyclopropylethyl)-3-methoxy-6,7,8,8a,9,10-hexahydro-5H-9,4b-(epiminoethano)phenanthrene

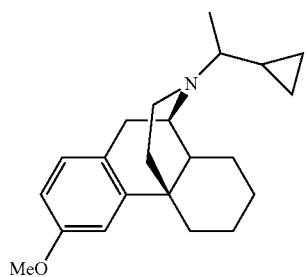

Chemical Formula: $C_{22}H_{31}NO$
Exact Mass: 325.24
Molecular Weight: 325.49

A mixture of (4bR,9R)-3-methoxy-6,7,8,8a,9,10-hexahydro-5H-9,4b-(epiminoethano)phenanthrene (1.41 g), methylcyclopropyl ketone (17 mL, 172 mmol), and acetic acid were heated at 70° C. for 1 hour. Sodium cyanoborohydride was added (830 mg, 13.2 mmol) and the mixture heated at 70° C. overnight. The reaction mixture was portioned between ethyl acetate (500 mL) and saturated sodium bicarbonate (500 mL). The organic phase was washed with brine and dried ($MgSO_4$). Filtration and removal of the solvent under reduced pressure gave the crude product that was purified by silica chromatography (2% methanol/ammonia in dichloromethane) giving (4bR,9R)-11-(1-cyclopropylethyl)-3-methoxy-6,7,8,8a,9,10-hexahydro-5H-9,4b-(epiminoethano)phenanthrene (0.75 g, 42% yield); LC/MS (M+H)$^+$=326.1.

(4bR,9R)-11-(1-cyclopropylethyl)-6,7,8,8a,9,10-hexahydro-5H-9,4b-(epiminoethano)phenanthren-3-ol

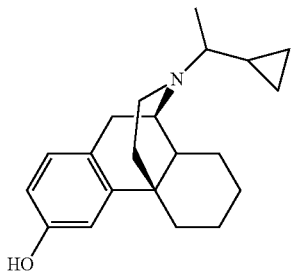

Chemical Formula: $C_{21}H_{29}NO$
Exact Mass: 311.22
Molecular Weight: 311.46

To an ice cooled solution of (4bR,9R)-11-(1-cyclopropylethyl)-3-methoxy-6,7,8,8a,9,10-hexahydro-5H-9,4b-(epiminoethano)phenanthrene (0.75 g, 2.31 mmol) in dichloromethane (50 mL) was added BBr$_3$ (0.9 mL, 9.23 mmol) dropwise under an argon atmosphere. The reaction was stirred for 3 hours then quenched with ammonia/methanol. The solvent was removed under reduced pressure giving (4bR,9R)-11-(1-cyclopropylethyl)-6,7,8,8a,9,10-hexahydro-5H-9,4b-(epiminoethano)phenanthren-3-ol (0.75 g, 100% yield); LC/MS (M+H)$^+$=312.1.

(4bR,9R)-11-(1-cyclopropylethyl)-6,7,8,8a,9,10-hexahydro-5H-9,4b-(epiminoethano)phenanthren-3-yl trifluoromethanesulfonate

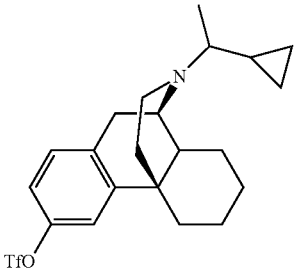

Chemical Formula: $C_{22}H_{28}F_3NO_3S$
Exact Mass: 443.17
Molecular Weight: 443.52

To a solution of (4bR,9R)-11-(1-cyclopropylethyl)-6,7,8,8a,9,10-hexahydro-5H-9,4b-(epiminoethano)phenanthren-3-ol (0.75 g, 2.41 mmol) and triethylamine (1.0 mL, 7.23 mmol) in dichloromethane (50 mL) was added N-Phenylbis(trifluoromethanesulfonamide) (0.95 g, 2.65 mmol) and the mixture stirred at room temperature overnight. The solvent was concentrated under reduced pressure to and the residue partitioned between 20% hexane in ethyl acetate (300 mL) and water (150 mL). The organic layer was washed four more times more with water and dried (MgSO$_4$). Filtration and removal of the solvent under reduced pressure gave (4bR,9R)-11-(1-cyclopropylethyl)-6,7,8,8a,9,10-hexahydro-5H-9,4b-(epiminoethano)phenanthren-3-yl trifluoromethanesulfonate (0.78 g, 73% yield); LC/MS (M+H)$^+$=444.1.

(4bR,9R)-11-(1-cyclopropylethyl)-N-(2,4-dimethoxybenzyl)-6,7,8,8a,9,10-hexahydro-5H-9,4b-(epiminoethano)phenanthrene-3-carboxamide

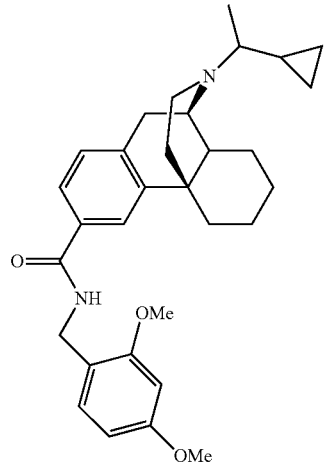

Chemical Formula: $C_{31}H_{40}N_2O_3$
Exact Mass: 488.30
Molecular Weight: 488.66

To a solution of (4bR,9R)-11-(1-cyclopropylethyl)-6,7,8,8a,9,10-hexahydro-5H-9,4b-(epiminoethano)phenanthren-3-yltrifluoromethanesulfonate (0.78 g, 1.76 mmol) in degassed dimethyl sulfoxide (15 mL), was added N-hydroxysuccinimide (405 mg, 3.52 mmol), palladium acetate (79 mg, 0.352 mmol), triethylamine (490 µL, to 3.52 mmol) and 4,5-bis(diphenylphosphino)-9,9-dimethylxanthene (203 mg, 0.352 mmol). The reaction mixture was heated with carbon monoxide (1 atm) at 75° C. overnight. The reaction mixture was cooled to ambient temperature and 2,4-dimethoxybenzylamine (294 mg, 1.76 mmol) added. The mixture was stirred for 1 hour before partitioning between water (300 mL) and ethyl acetate (400 mL). The aqueous phase was extracted twice more with ethyl acetate. The combined organic phase was dried (MgSO$_4$), filtered, and the solvent removed under reduced pressure. The crude material was purified by silica chromatography (3% methanol in dichloromethane) to give (4bR,9R)-11-(1-cyclopropylethyl)-N-(2,4-dimethoxybenzyl)-6,7,8,8a,9,10-hexahydro-5H-9,4b-(epiminoethano) phenanthrene-3-carboxamide (1.0 g, contains impurities—used directly in next step); LC/MS (M+H)$^+$=489.1.

(4bR,9R)-11-((R)-1-cyclopropylethyl)-6,7,8,8a,9,10-hexahydro-5H-9,4b-(epiminoethano)phenanthrene-3-carboxamide

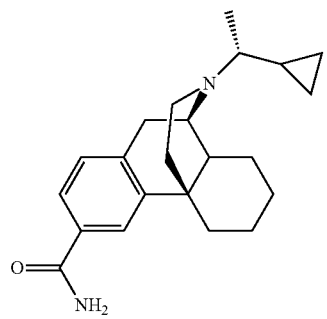

Chemical Formula: $C_{22}H_{30}N_2O$
Exact Mass: 338.24
Molecular Weight: 338.49

A mixture of (4bR,9R)-11-(1-cyclopropylethyl)-N-(2,4-dimethoxybenzyl)-6,7,8,8a,9,10-hexahydro-5H-9,4b-(epiminoethano)phenanthrene-3-carboxamide (1.0 g, 2.05 mmol) in trifluoroacetic acid (30 mL) was stirred at room temperature for 2 hours. The mixture was concentrated under reduced pressure before quenching with ice/ammonium hydroxide (28%) (50 mL). The crude product was extracted twice using dichloromethane (200 mL) and the combined organic layers dried (MgSO₄). Filtration and removal of the solvent under reduced pressure gave the crude product that was purified and separated from the (S)-diastereomer using prep-HPLC giving (4bR,9R)-11-((R)-1-cyclopropylethyl)-6,7,8,8a,9,10-hexahydro-5H-9,4b-(epiminoethano)phenanthrene-3-carboxamide (64 mg, 10% yield); LC/MS (M+H)⁺=339.3.

(4bR,9R)-11-((R)-1-cyclopropylethyl)-6,7,8,8a,9,10-hexahydro-5H-9,4b-(epiminoethano)phenanthrene-3-carboxamide hydrochloride

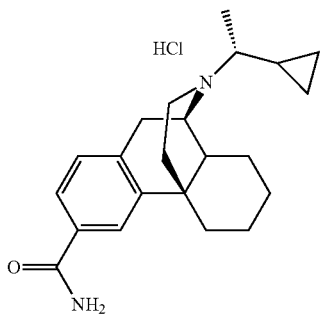

Chemical Formula: $C_{22}H_{31}ClN_2O$
Exact Mass: 374.21
Molecular Weight: 374.95

To a solution of (4bR,9R)-11-((R)-1-cyclopropylethyl)-6,7,8,8a,9,10-hexahydro-5H-9,4b-(epiminoethano)phenanthrene-3-carboxamide (64 mg, 0.19 mmol) in ethyl acetate (15 mL) was added 2N HCl/ether (140 µL, 0.28 mmol) and the mixture stirred for 30 minutes. The solvent was removed under reduced pressure then freeze dried giving (4bR,9R)-11-((R)-1-cyclopropylethyl)-6,7,8,8a,9,10-hexahydro-5H-9,4b-(epiminoethano)phenanthrene-3-carboxamide hydrochloride (71 mg, 100% yield); LC/MS (M+H)⁺=339.3. ¹H-NMR (400 MHz, DMSO) δ 10.41 (br s, 1H), 7.95 (s, 1H), 7.81 (s, 1H), 7.68 (d, 1H), 7.30 (s, 1H), 7.22 (d, 1H), 4.18 (s, 1H), 3.57-3.03 (m, 3H+H₂O), 2.95 (d, 1H), 2.55 (d, 1H), 2.37-2.16 (m, 2H), 2.08-1.87 (m, 1H), 2.68-0.51 (m, 15H), 0.20 (s, 1H).

A6. Experimental Procedure for Compound E and a Hydrochloride Salt Thereof

Synthesis of (4R,4aR,7aR,12bS)-3-(cyclobutylmethyl)-1,2,3,4,4a,5,6,7a-octahydrospiro[4,12-methanobenzofuro[3,2-e]isoquinoline-7,2'-[1,3]dioxolane]-9-carbonitrile

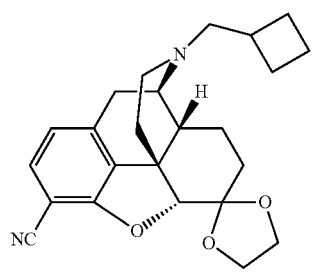 [SMILES: N#Cc1ccc2c3c1O[C@H]1C4(CC[C@H]5[C@@H](C2)N(CC2CCC2)CC[C@@]351)OCCO4]

To a solution of cyclobutane carboxaldehyde (19.45 g, 231.2 mmol) in dichloromethane (500 mL) was added (4R,4aR,7aR,12bS)-1,2,3,4,4a,5,6,7a-octahydrospiro[4,12-methanobenzofuro[3,2-e]isoquinoline-7,2'-[1,3]dioxolane]-9-carbonitrile (25 g, 77.1 mmol). The reaction was stirred for 60 minutes at room temperature before sodium triacetoxyborohydride (32.7 g, 154.0 mmol) was added portionwise over 20 minutes. After one hour, the reaction was quenched with NaHCO₃ solution and extracted with dichloromethane (×3). The dichloromethane phases were combined, washed with brine, dried over MgSO₄ and concentrated under reduced pressure. The residue was purified by silica chromatography eluted with dichloromethane to 7% methanol in dichloromethane to give (4R,4aR,7aR,12bS)-3-(cyclobutylmethyl)-1,2,3,4,4a,5,6,7a-octahydrospiro[4,12-methanobenzofuro[3,2-e]isoquinoline-7,2'-[1,3]dioxolane]-9-carbonitrile (31.1 g, 98% pure LCMS, assume quant.); [M+H]⁺ 393.1.

Synthesis of (4R,4aR,7aR,12bS)-3-(cyclobutylmethyl)-7-oxo-2,3,4,4a,5,6,7,7a-octahydro-1H-4,12-methanobenzofuro[3,2-e]isoquinoline-9-carbonitrile

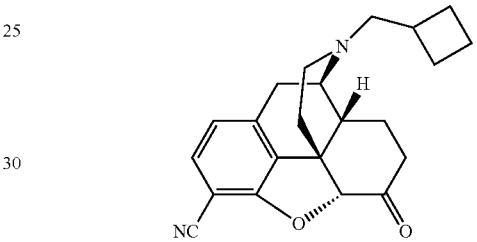

A suspension of (4R,4aR,7aR,12bS)-3-(cyclobutylmethyl)-1,2,3,4,4a,5,6,7a-octahydrospiro[4,12-methanobenzofuro[3,2-e]isoquinoline-7,2'-[1,3]dioxolane]-9-carbonitrile (31.1 g, 79.2 mmol) in 6M HCl(aq) (250 mL) was stirred at room temperature at room temperature for 24 hours. Further 6M HCl was added (25 mL) and stirred for an additional 24 hours. The reaction was poured onto ice/NH₃(aq) and stirred for 30 minutes and the solid collected by suction filtration and washed with water. The solid was dissolved in dichloromethane and washed with brine, dried over MgSO₄ and concentrated under reduced pressure to give (4R,4aR,7aR,12bS)-3-(cyclobutylmethyl)-7-oxo-2,3,4,4a,5,6,7,7a-octahydro-1H-4,12-methanobenzofuro[3,2-e]isoquinoline-9-carbonitrile (26.1 g, 96% pure LCMS, 95% yield); [M+H]⁺ 367.2.

Synthesis of (4R,4aR,7aR,12bS)-3-(cyclobutylmethyl)-7-oxo-2,3,4,4a,5,6,7,7a-octahydro-1H-4,12-methanobenzofuro[3,2-e]isoquinoline-9-carboxamide

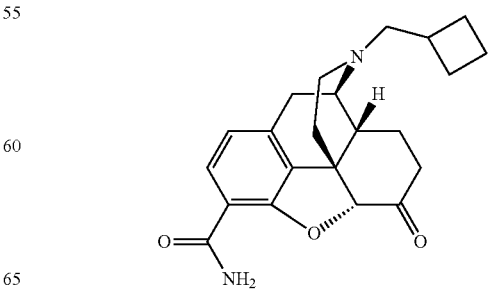

To a solution of (4R,4aR,7aR,12bS)-3-(cyclobutylmethyl)-7-oxo-2,3,4,4a,5,6,7,7a-octahydro-1H-4,12-methanobenzofuro[3,2-e]isoquinoline-9-carbonitrile (24 g, 68.9 mmol) in tert-butanol (240 mL) was added KOH (2.1 g, 37.1 mmol). The reaction was heated to 100° C. for 15 minutes. The reaction was allowed to cool to room temperature and concentrated to 50% volume. Diluted with water and extracted with ethyl acetate twice. The organic phases were combined, washed with to sodium hydrogen carbonate solution and brine and dried over MgSO$_4$ and concentrated under reduced pressure. The residue was purified by silica chromatography eluted with 4% methanol in dichloromethane to give to give (4R,4aR,7aR,12bS)-3-(cyclobutylmethyl)-7-oxo-2,3,4,4a,5,6,7,7a-octahydro-1H-4,12-methanobenzofuro[3,2-e]isoquinoline-9-carboxamide (14.2 g, 89% pure LCMS, 56% yield); [M+H]$^+$ 367.2.

Synthesis of (4bS,8aR,9R)-11-(cyclobutylmethyl)-4-hydroxy-6-oxo-6,7,8,8a,9,10-hexahydro-5H-9,4b-(epiminoethano)phenanthrene-3-carboxamide (Compound E)

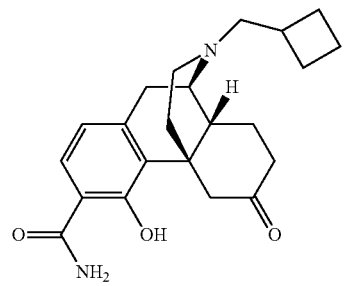 [SMILES: NC(=O)c1ccc2c(c1O)[C@]13CCN(CC4CCC4)[C@H](C2)[C@@H]1CCC(=O)C3]

To a solution of (4R,4aR,7aR,12bS)-3-(cyclobutylmethyl)-7-oxo-2,3,4,4a,5,6,7,7a-octahydro-1H-4,12-methanobenzofuro[3,2-e]isoquinoline-9-carboxamide (14.2 g, 38.75 mmol) in ethanol (500 mL) was added ammonium chloride (31.1 g, 581 mmol) followed by zinc powder (25.3 g, 388 mmol). The reaction was heated to reflux for 2.5 hours. The reaction was cooled to ~50° C. and filtered through a pad of celite. The celite was washed with ethanol/methanol. The filtrate was concentrated under reduced pressure. The residue was partitioned between dichloromethane and NH$_{3(aq)}$/H$_2$O (1:1) and the aqueous phase re-extracted with dichloromethane. The combined dichloromethane phase was washed with brine, dried over MgSO$_4$ and concentrated. The crude product was purified by silica chromatography and eluted with 3.5% NH$_3$/methanol in dichloromethane to give (4bS,8aR,9R)-11-(cyclobutylmethyl)-4-hydroxy-6-oxo-6,7,8,8a,9,10-hexahydro-5H-9,4b-(epiminoethano)phenanthrene-3-carboxamide (9.7 g, 98.5% pure LCMS, 68% yield); [M+H]$^+$ 369.2.

Synthesis of (4bS,6S,8aR,9R)-11-(cyclobutylmethyl)-4,6-dihydroxy-6,7,8,8a,9,10-hexahydro-5H-9,4b-(epiminoethano)phenanthrene-3-carboxamide hydrochloride

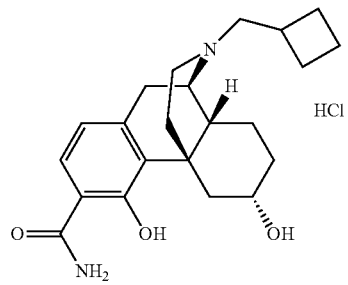 [SMILES: NC(=O)c1ccc2c(c1O)[C@]13CCN(CC4CCC4)[C@H](C2)[C@@H]1CC[C@H](O)C3 ; Cl]

1M K-selectride in tetrahydrofuran (49.9 mL) was added to a solution of (4bS,8aR,9R)-11-(cyclobutylmethyl)-4-hydroxy-6-oxo-6,7,8,8a,9,10-hexahydro-5H-9,4b-(epiminoethano)phenanthrene-3-carboxamide (9.2 g, 25.0 mmol) in tetrahydrofuran (150 mL) cooled in an ice bath. After 30 minutes a saturated solution of ammonium chloride was added and the reaction mixture extracted with ethyl acetate (×3). The combined organic phase was washed with sodium hydrogen carbonate solution and brine, dried over MgSO$_4$ and concentrated. The residue was taken up in 2M HCl aq and washed with ethyl acetate. The aqueous phase was basified with 2 M NaOH to pH 7 then sodium hydrogen carbonate solution was added. The aqueous solution was extracted with dichloromethane (×3) dried over MgSO$_4$, concentrated, and purified via prep HPLC (30-50% acetonitrile in 0.1% NH$_4$HCO$_3$ pH10 buffer) to give (4bS,8aR,9R)-11-(cyclobutylmethyl)-4-hydroxy-6-oxo-6,7,8,8a,9,10-hexahydro-5H-9,4b-(epiminoethano)phenanthrene-3-carboxamide (4.7 g, 99.76% pure LCMS, 51% yield); [M+H]$^+$ 371.19.

To a solution of (4bS,8aR,9R)-11-(cyclobutylmethyl)-4-hydroxy-6-oxo-6,7,8,8a,9,10-hexahydro-5H-9,4b-(epiminoethano)phenanthrene-3-carboxamide (4.6 g, 12.4 mmol) in ethyl acetate (30 mL) and dichloromethane (30 mL) was added 2M HCl in diethyl ether (7.45 mL, 14.9 mmol). After 2 hours, the liquors were removed under reduced pressure and the residue suspended in diethyl ether, collected by suction filtration and washed with diethyl ether. The solid was dissolved in 9:1 water/methanol and freeze dried to give(4bS,6S,8aR,9R)-11-(cyclobutylmethyl)-4,6-dihydroxy-6,7,8,8a,9,10-hexahydro-5H-9,4b-(epiminoethano)phenanthrene-3-carboxamide hydrochloride (4.7 g, 99.81% pure LCMS, 93% yield); [M+H]$^+$ 371.19. $^1$H NMR (300 MHz, D$_2$O) 7.37 (1H, d), 6.62 (1H, d), 3.99 (1H, br s), 3.66 (1H, br d), 3.51 (1H, br s), 2.91-3.27 (5H, m), 2.44-2.62 (2H, m), 1.23-2.05 (14H, m).

A7. Experimental Procedure for Compound B and a Hydrochloride Salt Thereof

Synthesis of (4bS,8aR,9R)-11-(cyclopropylmethyl)-5,7,8,8a,9,10-hexahydrospiro[9,4b-(epiminoethano)phenanthrene-6,2'-[1,3]dioxolane]-3-carbonitrile

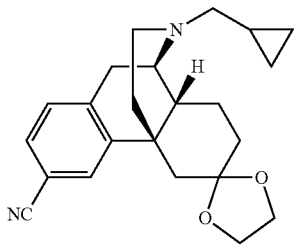 [SMILES: N#Cc1ccc2c(c1)[C@]13CCN(CC4CC4)[C@H](C2)[C@@H]1CCC1(C3)OCCO1]

To a solution of (4bS,8aR,9R)-5,7,8,8a,9,10-hexahydrospiro[9,4b-(epiminoethano)phenanthrene-6,2'-[1,3]dioxolane]-3-carbonitrile (3.58 g, 11.5 mmol) in dichloromethane (115 mL) was added cyclopropylcarboxaldehyde (2.55 mL, 34.6 mmol). The reaction was stirred for 60 minutes at room temperature before sodium triacetoxyborohydride (4.90 g, 23.1 mmol) was added portionwise. After one hour, the reaction was quenched with aqueous NaHCO$_3$ solution and extracted with dichloromethane (×3). The dichloromethane phases were combined, washed with brine, dried over MgSO$_4$ and concentrated under reduced pressure. The residue was purified by silica chromatography eluted with dichloromethane to 5% methanol in dichloromethane to give (4bS,8aR,9R)-11-(cyclopropylmethyl)-5,7,8,8a,9,10-hexahydrospiro[9,4b-(epiminoethano)phenanthrene-6,2'-[1,3]dioxolane]-3-carbonitrile (3.59 g, 98.5% pure LCMS, 86% yield); [M+H]$^+$ 365.2.

Synthesis of (4bS,8aR,9R)-11-(cyclopropylmethyl)-5,7,8,8a,9,10-hexahydrospiro[9,4b-(epiminoethano)phenanthrene-6,2'-[1,3]dioxolane]-3-carboxamide

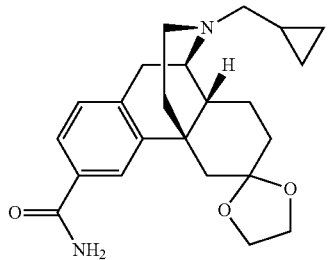

To a solution of (4bS,8aR,9R)-11-(cyclopropylmethyl)-5,7,8,8a,9,10-hexahydrospiro[9,4b-(epiminoethano)phenanthrene-6,2'-[1,3]dioxolane]-3-carbonitrile (3.95 g, 9.9 mmol) in dimethylsulfoxide (40 mL) was added potassium carbonate (4.09 g, 29.6 mmol). The reaction was cooled to 15° C. and hydrogen peroxide (12 mL, 35% aqueous solution) added dropwise maintaining the temperature between 15 and 20° C. After addition was complete, the reaction was allowed to warm to room temperature. The reaction was cooled to 0° C., quenched with water and extracted with ethyl acetate. The reaction was basified with sodium hydrogen carbonate solution to pH 10 and extracted with ethyl acetate (×3). The organics were combined, washed with water (×3), brine, dried over MgSO$_4$ and concentrated under reduced pressure. The product was purified by silica chromatography eluted with a gradient from 100% dichloromethane to 10% NH$_3$/methanol in dichloromethane to give (4bS,8aR,9R)-11-(cyclopropylm-ethyl)-5,7,8,8a,9,10-hexahydrospiro[9,4b-(epiminoethano)phenanthrene-6,2'-[1,3]dioxolane]-3-carboxamide (2.76 g, 98.3% pure LCMS, 73% yield); [M+1-1]$^+$383.2.

Synthesis of (4bS,8aR,9R)-11-(cyclopropylmethyl)-6-oxo-6,7,8,8a,9,10-hexahydro-5H-9,4b-(epiminoethano)phenanthrene-3-carboxamide hydrochloride

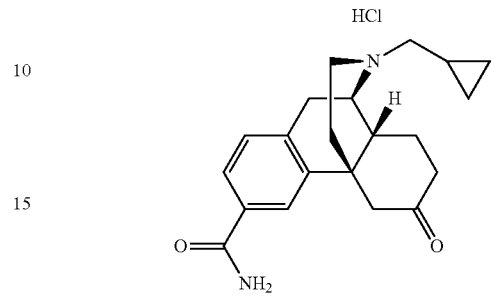

To (4bS,8aR,9R)-11-(cyclopropylmethyl)-5,7,8,8a,9,10-hexahydrospiro[9,4b-(epiminoethano)phenanthrene-6,2'-[1,3]dioxolane]-3-carboxamide (2.76 g, 7.2 mmol) was added 6M HCl (aq) (60 mL) with cooling. After an hour the reaction was poured onto ice/NH$_{3(aq)}$ and extracted with dichloromethane (×3). The dichloromethane phases were combined, washed with brine, dried over MgSO$_4$ and concentrated under reduced pressure. The residue was purified by silica chromatography eluted with 100% dichloromethane to 10% NH$_3$/methanol in dichloromethane to give Compound B: (4bS,8aR,9R)-11-(cyclopropylmethyl)-6-oxo-6,7,8,8a,9,10-hexahydro-5H-9,4b-(epiminoethano)phenanthrene-3-carboxamide (2.41 g, 97.5% pure LCMS, 96% yield).

To (4bS,8aR,9R)-11-(cyclopropylmethyl)-6-oxo-6,7,8,8a,9,10-hexahydro-5H-9,4b-(epiminoethano)phenanthrene-3-carboxamide (2.39 g, 7.1 mmol) in ethyl acetate (60 mL) was added 2M HCl in diethyl ether (3.87 mL, 7.8 mmol). The product precipitated from solution and was collected by filtration. The solid was washed with to ethyl acetate and diethyl ether before drying under vacuum. The product was dissolved in water and freeze dried to give (4bS,8aR,9R)-11-(cyclopropylmethyl)-6-oxo-6,7,8,8a,9,10-hexahydro-5H-9,4b-(epiminoethano)phenanthrene-3-carboxamide hydrochloride (2.62 g, 99.9% LCMS, 99% yield); [M+H]$^+$ 339.3. $^1$H NMR (300 MHz, D$_2$O) 7.60 (1H, s), 7.43 (1H, d), 7.17 (1H, d), 4.07 (0.8H, d), 3.97 (0.2H, d), 2.34-3.44 (10H, m), 1.74-2.18 (3H, m), 1.60 (0.8H, d), 1.44 (0.2H, d), 1.27 (1H, dq), 0.96 (1H, m), 0.59 (2H, d), 0.25 (2H, m).

A8. Experimental Procedure for

Synthesis of (4bS,8aR,9R)-11-(cyclobutylmethyl)-5,7,8,8a,9,10-hexahydrospiro[9,4b-(epiminoethano)phenanthrene-6,2'-[1,3]dioxolane]-3-carbonitrile

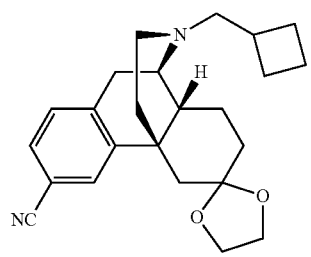

To a solution of cyclobutylmethanol (3.70 g, 42.9 mmol) in dichloromethane (100 mL) was added silica (25 g), followed by pyridinium chlorochromate (18.52 g, 85.9 mmol). The reaction mixture was stirred for 2 h and filtered through a plug of silica eluting with dichloromethane (300 mL). The resulting solution was concentrated to about 75 mL and (4bS,8aR,9R)-5,7,8,8a,9,10-hexahydrospiro[9,4b-(epiminoethano)phenanthrene-6,2'-[1,3]dioxolane]-3-carbonitrile (0.40 g, 0.13 mmol) added, followed by sodium triacetoxyborohydride (0.71 g, 0.34 mmol). The reaction mixture was stirred for 2 h, washed with aqueous sat. NaHCO$_3$ (100 mL) and dried over MgSO$_4$. After filtration and evaporation the residue was further purified by silica column chromatography eluting with 5-10% methanol/dichloromethane to give the desired product (4bS,8aR,9R)-11-(cyclobutylmethyl)-5,7,8,8a,9,10-hexahydrospiro[9,4b-(epiminoethano)phenanthrene-6,2'-[1,3]dioxolane]-3-carbonitrile as a yellow oil (0.48 g, 56% pure LCMS); [M+H]$^+$ 379.3. This was used in the next reaction without further purification.

Synthesis of (4bS,8aR,9R)-11-(cyclobutylmethyl)-5,7,8,8a,9,10-hexahydrospiro[9,4b-(epiminoethano)phenanthrene-6,2'-[1,3]dioxolane]-3-carboxamide

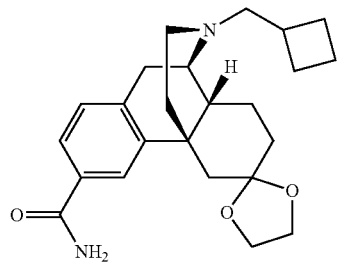

To (4bS,8aR,9R)-11-(cyclobutylmethyl)-5,7,8,8a,9,10-hexahydrospiro[9,4b-(epiminoethano)phenanthrene-6,2'-[1,3]dioxolane]-3-carbonitrile (0.48 g, 13 mmol) in dimethylsulfoxide (12 mL) was added potassium carbonate (0.53 g, 3.8 mmol). The reaction was cooled to 15° C. and hydrogen peroxide (2.0 mL, 35% aqueous solution) added dropwise maintaining the temperature between 15 and 20° C. After addition was complete, the reaction was allowed to warm to room temperature. The reaction was cooled to 0° C., quenched with water and extracted with ethyl acetate. The reaction was basified with sodium hydrogen carbonate solution and extracted with ethyl acetate (×3). The organics were combined, washed with water (×3), brine, dried over MgSO$_4$ and concentrated under reduced pressure. The product was purified by silica chromatography eluted with a gradient from 10% methanol in dichloromethane to 5% NH$_3$/methanol in dichloromethane to give (4bS,8aR,9R)-11-(cyclobutylmethyl)-5,7,8,8a,9,10-hexahydrospiro[9,4b-(epiminoethano)phenanthrene-6,2'-[1,3]dioxolane]-3-carboxamide (0.27 g, 94% pure LCMS, 54% yield over two steps); [M+H]$^+$ 397.3.

Synthesis of (4bS,8aR,9R)-11-(cyclobutylmethyl)-6-oxo-6,7,8,8a,9,10-hexahydro-5H-9,4b-(epiminoethano)phenanthrene-3-carboxamide hydrochloride

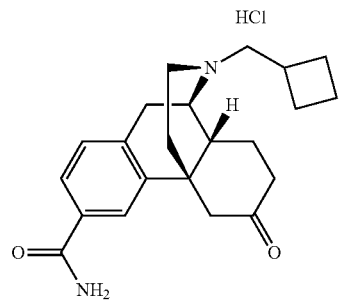

To (4bS,8aR,9R)-11-(cyclobutylmethyl)-5,7,8,8a,9,10-hexahydrospiro[9,4b-(epiminoethano)phenanthrene-6,2'-[1,3]dioxolane]-3-carboxamide (274 mg, 0.69 mmol) was added 6M HCl (aq) (12 mL). The reaction was stirred for 24 hours until complete. The reaction was poured onto ice/NH$_3$ (aq) and extracted with dichloromethane (×3). The dichloromethane phases were combined, washed with brine, dried over MgSO$_4$ and concentrated under reduced pressure. The residue was purified by silica chromatography eluted with 5-10% NH$_3$/methanol in dichloromethane to give (4bS,8aR,9R)-11-(cyclobutylmethyl)-6-oxo-6,7,8,8a,9,10-hexahydro-5H-9,4b-(epiminoethano)phenanthrene-3-carboxamide (225 mg, 99.2% pure LCMS, 93% yield).

To (4bS,8aR,9R)-11-(cyclobutylmethyl)-6-oxo-6,7,8,8a,9,10-hexahydro-5H-9,4b-(epiminoethano)phenanthrene-3-carboxamide (225 mg, 0.64 mmol) in ethyl acetate (10 mL) was added 2M HCl in diethyl ether (0.35 mL, 0.70 mmol). The product precipitated from solution and the liquors were concentrated under vacuum. The solid was triturated with diethyl ether before drying under vacuum. The product was dissolved in water and freeze dried to give (4bS,8aR,9R)-11-(cyclobutylmethyl)-6-oxo-6,7,8,8a,9,10-hexahydro-5H-9,4b-(epiminoethano)phenanthrene-3-carboxamide hydrochloride (237 mg, 99.3% LCMS, 89% yield); [M+H]353.2. $^1$H NMR (300 MHz, D$_2$O) 7.69 (1H, s), 7.59 (1H, dd), 7.29 (1H, d), 3.84 (1H, s), 2.48-3.55 (11H, m), 1.31-2.31 (11H, m).

A9. Experimental Procedure for

Synthesis of (4bS,6S,8aR,9R)-11-(cyclobutylmethyl)-6-hydroxy-6,7,8,8a,9,10-hexahydro-5H-9,4b-(epiminoethano)phenanthrene-3-carboxamide hydrochloride

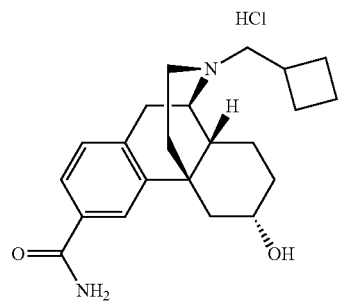

To a solution of (4bS,8aR,9R)-11-(cyclobutylmethyl)-6-oxo-6,7,8,8a,9,10-hexahydro-5H-9,4b-(epiminoethano)phenanthrene-3-carboxamide (84 mg, 0.24 mmol) in methanol (4 mL) was added sodium borohydride (18 mg, 0.48 mmol) at room temperature. The reaction was stirred for an hour before quenching with to ammonium chloride solution. The aqueous phase was basified with 2M NaOH solution and extracted with dichloromethane (×4). The dichloromethane phases were combined, washed with brine, dried over MgSO$_4$ and concentrated under reduced pressure. The residue was purified by silica chromatography eluted with 10% NH$_3$/methanol in dichloromethane to separate the diastereoisomers. The major diastereoisomer was the desired (4bS,6S,8aR,9R)-11-(cyclobutylmethyl)-6-hydroxy-6,7,8,8a,9,10-hexahydro-5H-9,4b-(epiminoethano)phenanthrene-3-carboxamide (50 mg, 98.1% pure LCMS, 59% yield).

To (4bS,6S,8aR,9R)-11-(cyclobutylmethyl)-6-hydroxy-6,7,8,8a,9,10-hexahydro-5H-9,4b-(epiminoethano)phenanthrene-3-carboxamide (50 mg, 0.14 mmol) in ethyl acetate (4 mL) was added 2M HCl in diethyl ether (0.07 mL, 0.70 mmol). The solvent was removed under vacuum before freeze drying from water to give (4bS,6S,8aR,9R)-11-(cyclobutylmethyl)-6-hydroxy-6,7,8,8a,9,10-hexahydro-5H-9,4b-(epiminoethano)phenanthrene-3-carboxamide hydrochloride (55 mg, 99.0% pure LCMS, 100% yield); [M+H]$^+$ 355.3. $^1$H NMR (300 MHz, D$_2$O) 7.76 (1H, s), 7.44 (1H, d), 7.16 (1H, d), 4.02 (1H, s), 3.58 (1H, s), 2.88-3.44 (5H, m), 2.70 (1H, d), 2.55 (1H, m), 2.35 (1H, dt), 0.99-2.16 (14H, m).

Par B. Biological Assay
B1. In Vitro Characterization

The in vitro kinetic and pharmacological characteristics of the compounds set forth in Table B, Table C, Table D, and Table E are tested using the following assays.

Opioid Receptor Binding Assay

The K$_i$ (binding affinity) for μ opioid receptors was determined using a competitive displacement assay as previously described in Neumeyer (Journal of Med. Chem. 2012, p 3878), which is incorporated herein in its entirety. Briefly, membrane protein from CHO (Chinese Hamster Ovarian) cells that stably expressed the cloned human μ opioid receptor were incubated with 12 different concentrations of the compound set forth herein in the presence of 0.25 nM [3H]DAMGO (see Tiberi et al., Can. J. Physiol. Pharmacol. 1988, Vol. 66, p 1368, which is incorporated by reference herein in its entirety) in a final volume of 1 mL of 50 mM Tris-HCl, pH 7.5 at 25° C. Incubation times of 60 mM were used for [3H]DAMGO (see Gulati et al., Life Sci. 1990, Vol. 47, p 159, which is incorporated by reference herein in its entirety). Nonspecific binding was measured by inclusion of 10 μM naloxone. The binding was terminated by filtering the samples through Schleicher & Schuell No. 32 glass fiber filters using a Brandel 48-well cell harvester. The filters were subsequently washed three times with 3 mL of cold 50 mM Tris-HCl, pH 7.5, and were counted in 2 mL Ecoscint A scintillation fluid. IC50 values were calculated by least squares fit to a logarithm-probit analysis. Ki values of unlabelled compounds were calculated from the equation Ki=(IC50)/1+S where S=(concentration of radioligand)/(Kd of radioligand) (Cheng and Prusoff, 1973). The calculated IC50 and Ki values for the compounds tested are set forth in Table B, Table C, Table D, and Table E, herein.

Functional Assay (GTPγS Binding)

The EC50 and Imax for μ opioid receptors was determined using a [$^{35}$S]GTPγS binding assay. This assay measures the functional properties of a compound by quantifying the level of G-protein activation following agonist binding in studies using stably transfected cells, and is considered to be a measure of the efficacy of a compound. Membranes from CHO (Chinese Hamster Ovary) cells that stably expressed the cloned human Mu opioid receptor were used in the experiments. Specifically, in a final volume of 0.5 mL, 12 different concentrations of each test compound were incubated with 7.5 μg of CHO cell membranes that stably expressed the human μ opioid receptor. The assay buffer consisted of 50 mM Tris-HCl, pH 7.4, 3 mM MgCl2, 0.2 mM EGTA, 3 μM GDP, and 100 mM NaCl. The final concentration of [35S]GTPγS was 0.080 nM. Nonspecific binding was measured by inclusion of 10 μM GTPγS. Binding was initiated by the addition of the membranes. After an incubation of 60 min at 30° C., the samples were filtered through Schleicher & Schuell No. 32 glass fiber filters. The filters were washed three times with cold 50 mM Tris-HCl, pH 7.5, and were counted in 2 mL of Ecoscint scintillation fluid. Data to are the mean Emax and EC50 values±S.E.M. For calculation of the Emax values, the basal [35S]GTPγS binding was set at 0%, and the 100% [35S]GTPγS binding level was set at the maximum binding achieved with DAMGO. To determine antagonist activity of a compound at the μ opioid receptors, CHO membranes expressing the u opioid receptor, were incubated with 12 different concentrations of the compound in the presence of 200 nM of the μ agonist DAMGO. The Emax values are the maximal percentage increase of [35S]GTPγS binding induced by a test compound relative to basal [35S]GTPγS binding in the absence of any drug. Data for antagonists are the mean Imax and IC50 values ±S.E.M. The calculated EC50 and Imax values for the compounds tested are set forth in Table B, Table C, Table D, and Table E, herein. It should be noted that the GTPγS binding assay described above is performed under conditions such that the observed Emax value for buprenorphine in this assay is at least 50% compared to baseline.

TABLE D

| Compound | μ Ki/ nM | μ EC50/ nM | μ Emax/ % | μ IC50/ nM | μ Imax/ % |
|---|---|---|---|---|---|
| 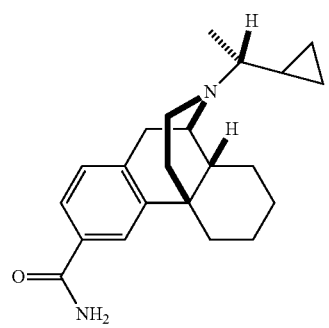<br>Compound 1 | 0.083 | 1.3 | 18 | 1.7 | 82 |

TABLE D-continued

| Compound | μ Ki/ nM | μ EC50/ nM | μ Emax/ % | μ IC50/ nM | μ Imax/ % |
|---|---|---|---|---|---|
| Compound 2 | 0.14 | — | 11 | 0.65 | 86 |
| Compound 3 | 5.8 | 7.7 | 43 | | 91 |
| Compound 4 | 1.2 | — | 11 | 38 | 86 |
| Compound 14 | 0.12 | 2.2 | 46 | 14 | 41 |

TABLE D-continued

| Compound | μ Ki/ nM | μ EC50/ nM | μ Emax/ % | μ IC50/ nM | μ Imax/ % |
|---|---|---|---|---|---|
| [structure] | 0.098 | 2.5 | 54 | 7.8 | 59 |
| [structure] | 0.1 | 0.89 | 21 | 1.5 | 80 |
| [structure] | 0.05 | | 20 | 58 | 89 |
| morphine | 0.32 | 34 ± 14 | 96.5 ± 36 | No inhibition | No inhibition |
| nalbuphine | 1.3 ± 0.4 | 21 ± 15 | 26 ± 1.55 | 88 ± 18 | 74 ± 2 |
| buprenorphine | 0.41 | 0.30 ± 0.042 | 53 ± 2.3 | 0.45 ± 0.060 | 48 ± 1.7 |

B2. Thermal Pain Assay

The antinociceptive effect of the compounds disclosed herein is determined using a rodent hot plate model. This model tests the responses to acute thermal pain in rats as set forth below.

Male Sprague-Dawley rats (275-425 g) are used for all studies. Rats are housed 2/cage and are given food and water ad libitum. Body weights were taken once before testing begins and rats were marked on their tail to indicate numbering. The hot plate apparatus (Columbus Instruments) was used to measure antinociception to acute thermal pain.

Rats are placed individually on the hot plate apparatus (surface temperature is equal to 52.5° C. and is confirmed with an infrared thermometer at the beginning of each study) and the response latency to lick either hind paw is recorded. The maximum response latency (MRL) is set to 60 seconds to avoid potential thermal injury associated with longer exposure times. Rats are tested for a baseline hot plate response (licking one hind paw) immediately prior to subcutaneous injection with test compound. Any rat which displays a baseline response latency greater than 30 seconds is removed from the study. The latency to lick a hind paw is compared to the dose of morphine (7.5 mg/kg, SC) that produced a maximum response latency of 60 seconds when measured 30 minutes after administration. Following test compound administration, rats are tested 30, 60, 90, 120, and 240 minutes later on the hot plate. The time to lick one hind paw is recorded as the response latency for each rat.

Raw data is reported as the time (in seconds) to lick one hind paw following exposure to the hot plate. The mean and SEM of the responses latencies for each experimental group are calculated and a line graph depicting mean hot plate latency vs. time is generated using GraphPad Prism. An increase in mean response latency above baseline following test compound administration is indicative of an antinociceptive effect.

In one study, the antinociceptive effects of Compound A, either alone or in combination with morphine were determined using the hot plate assay described above. Specifically, rats were administered: 1) 5 mg/kg morphine; 2) 1 mg/kg Compound A; 3) 5 mg/kg morphine and 0.01 mg/kg Compound A; 4) 5 mg/kg morphine and 0.1 mg/kg Compound A; or 5) 5 mg/kg morphine and 1 mg/kg Compound A. The results, set forth in FIG. 1, show that although Compound A inhibits morphine analgesia at doses ranging from 0.01 mg/kg to 1 mg/kg, Compound A alone has no antinociceptive effect at a dose of 1 mg/kg.

Figure 2:
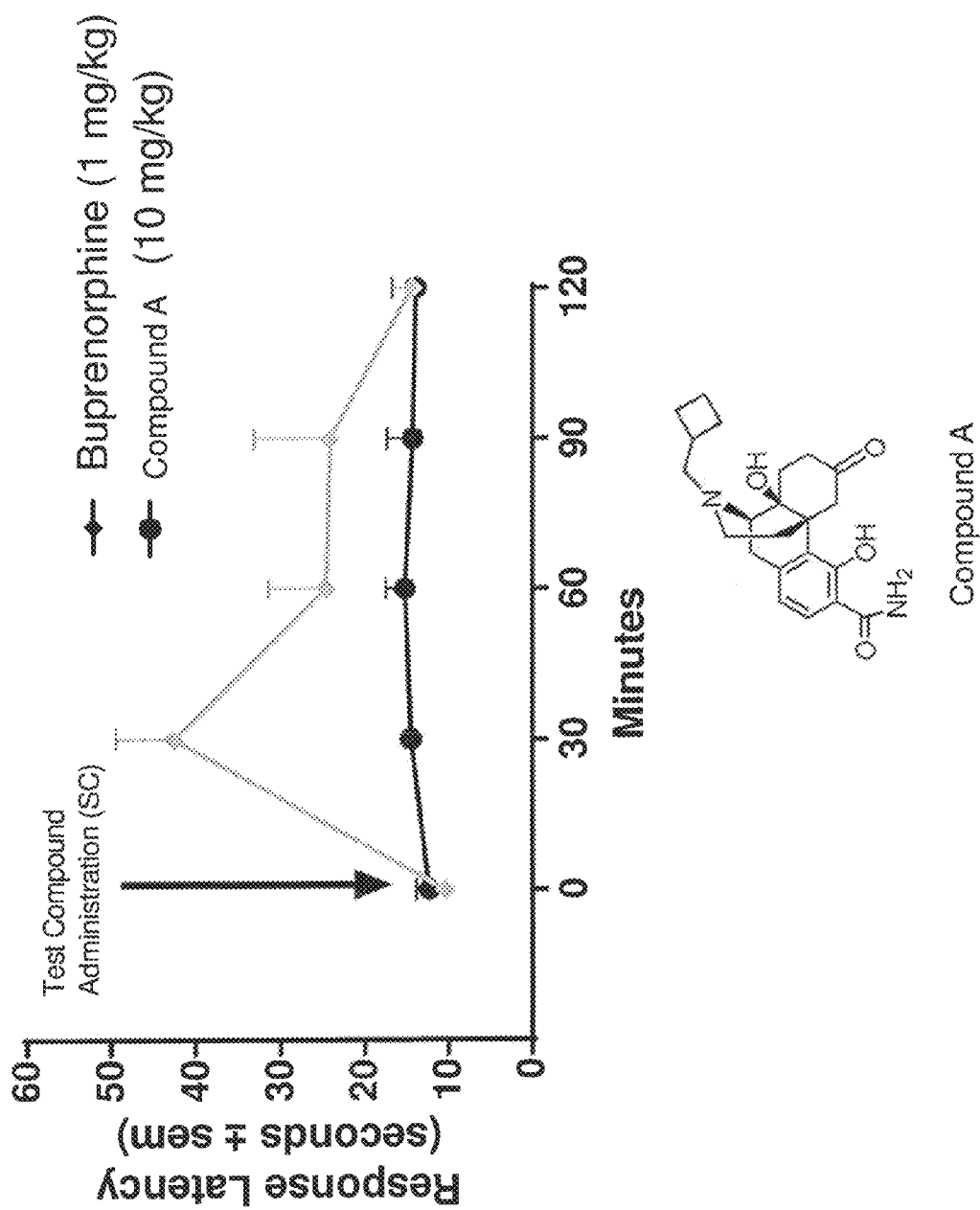
FIG. 2 depicts the results of experiments measuring the antinociceptive effects of Compound A, or buprenorphine using a rat hot plate assay.

In another study, the antinociceptive effects of Compound A and buprenorphine were compared using the hot plate assay described above. Specifically, rats were administered with either 10 mg/kg of Compound A, or 1 mg/kg of buprenorphine. The results, set forth in FIG. 2, show that buprenorphine inhibits thermal pain in rats at a dose of 1 mg/kg, whereas Compound A has no antinociceptive effect at a dose of 10 mg/kg.

Figure 4:
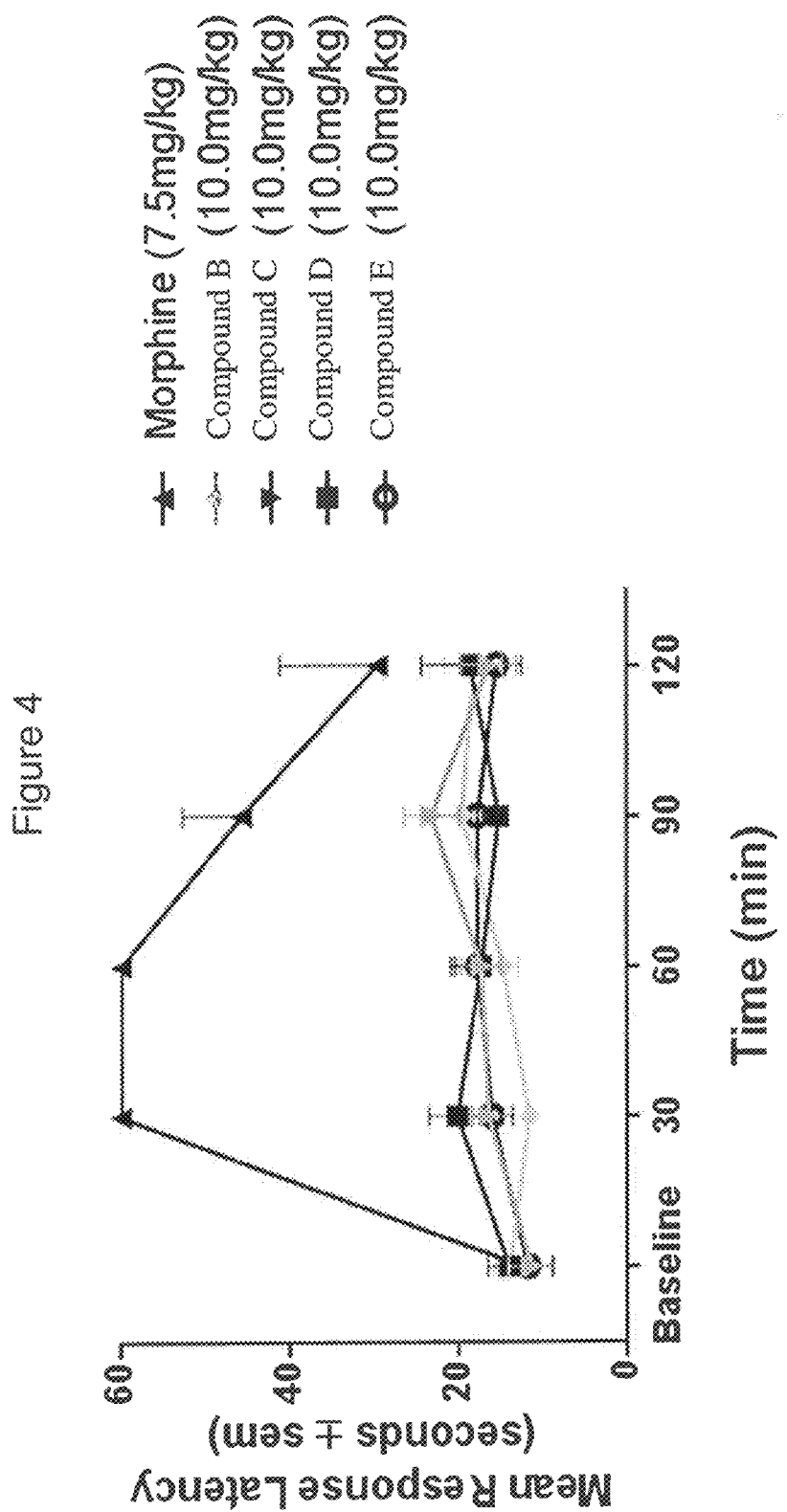
FIG. 4 depicts the results of experiments measuring the antinociceptive effects of morphine, Compound B, Compound C, Compound D and Compound E, using a rat hot plate assay.
Figure 5:
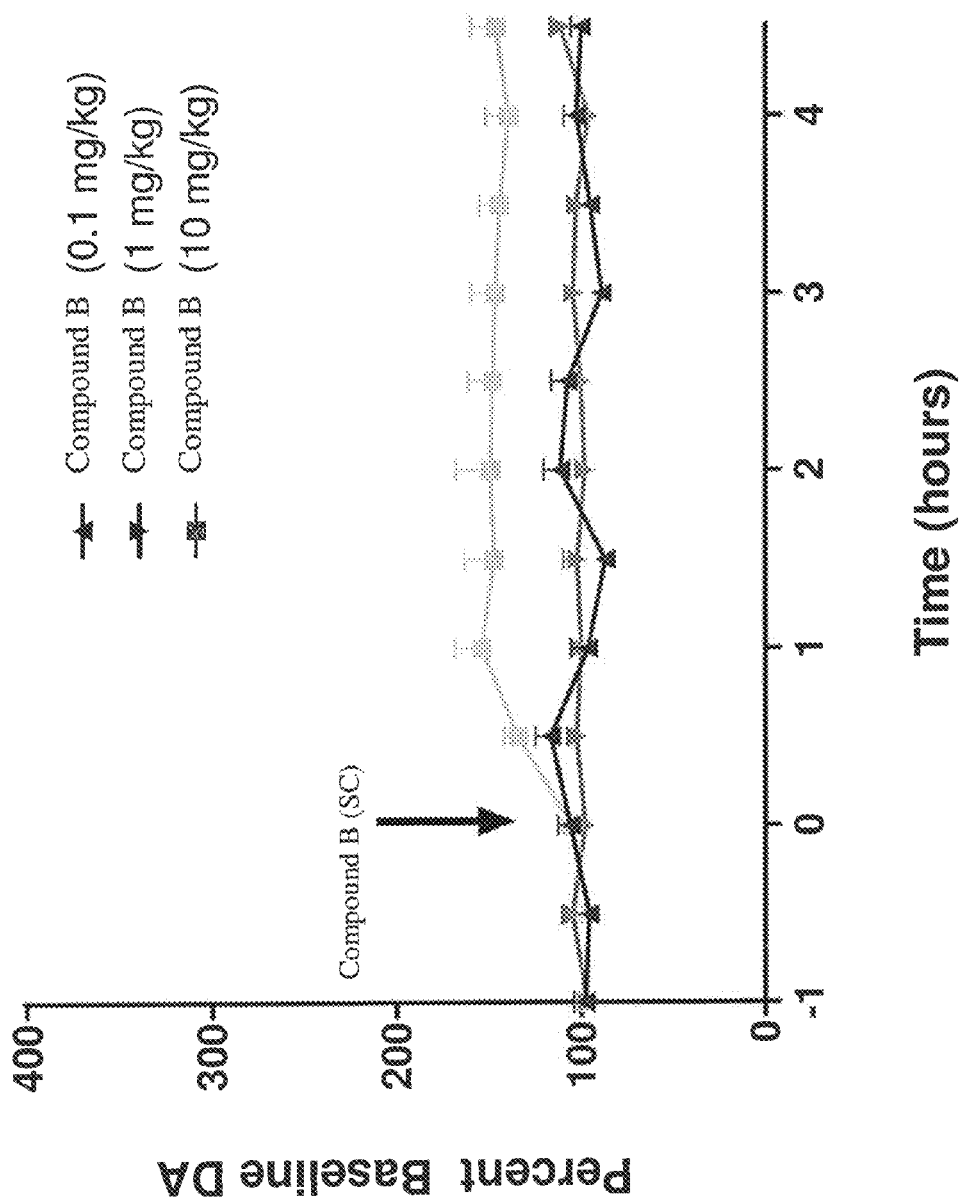
FIG. 5 depicts the results of in vivo microdialysis experiments measuring dopamine release in the rat nucleus accumbens induced by different doses of Compound B.
Figure 6:
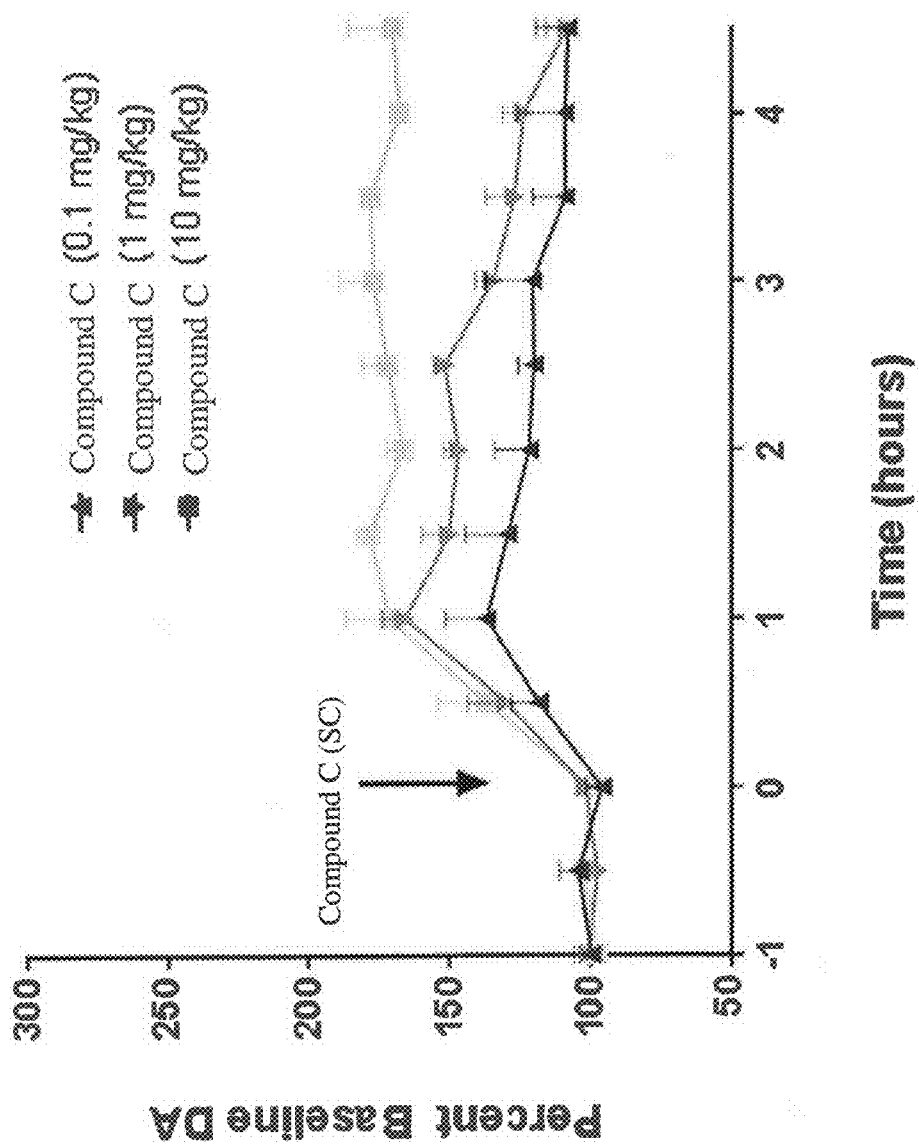
FIG. 6 depicts the results of in vivo microdialysis experiments measuring dopamine release in the rat nucleus accumbens induced by different doses of Compound C.
Figure 7:
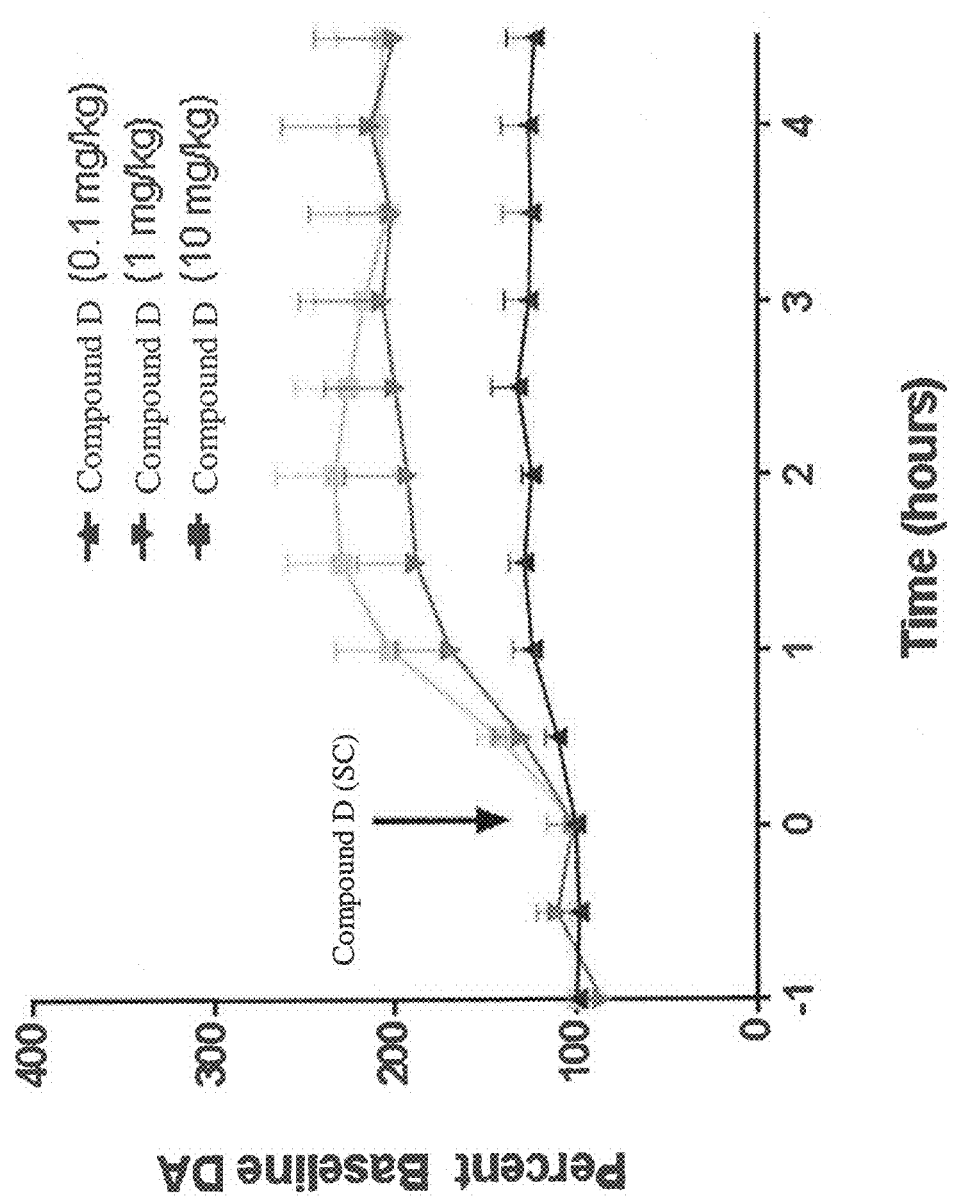
FIG. 7 depicts the results of in vivo microdialysis experiments measuring dopamine release in the rat nucleus accumbens induced by different doses of Compound D.
Figure 8:
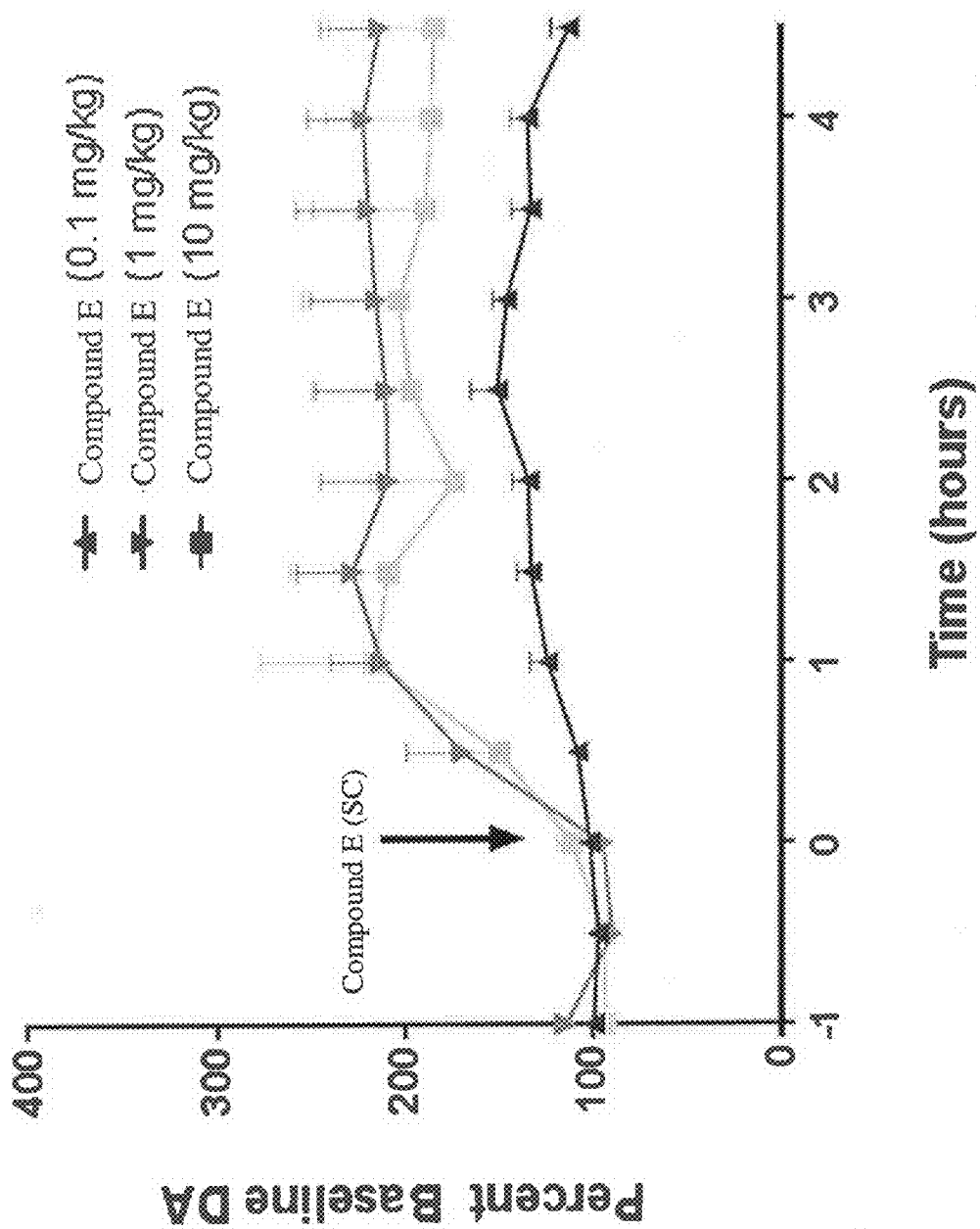
FIG. 8 depicts the results of in vivo microdialysis experiments measuring dopamine release in the rat nucleus accumbens induced by different doses of Compound E.

In another study, the antinociceptive effects of morphine, and Compounds B, C, D, and E, separately, were determined using the hot plate assay described above. Specifically, rats were administered: 1) 7.5 mg/kg morphine; 2) 10.0 mg/kg Compound B; 3) 10.0 mg/kg Compound C; 4) 10.0 mg/kg Compound D; or 5) 10.0 mg/kg Compound E. The results, set forth in FIG. 4, show that morphine inhibits thermal pain at a dose of 7.5 mg/kg, and that Compounds B, C, D, or E have no antinociceptive effect at a dose of 10.0 mg/kg.

B3. In vivo Dopamine Efflux Assay

The neurochemical response of the compounds disclosed herein is determined by in vivo microdialysis in awake rats. Intra-cranial microdialysis in rats allows the sampling of extracellular cerebrospinal fluid (CSF) from specific brain regions of interest and the measurement and quantitation of neurotransmitter, neuropeptide, and drug concentrations following the analysis of sampled dialysate with bioanalytical chemistry techniques. This technique allows measurement and comparison of neurotransmitter release in response to test compounds to basal neurotransmitter levels. The nucleus accumbens shell is a brain region which is critically important for understanding the rewarding effects of a variety of stimuli including food, mating behavior and drugs of abuse. Rewarding stimuli have been shown to act though multiple pathways to modulate the mesolimbic dopamine system, ultimately resulting in acute increases in extracellular DA ($DA_{ext}$) within the nucleus accumbens shell following systemic administration or self-administration. In these studies, microdialysate collected from probes implanted in the NAc-sh is analyzed for dopamine content by HPLC coupled to electrochemical detection (HPLC-EC) as set forth below.

Male Wistar rats (275-425 g) are used for all studies. Rats were housed 2/cage and are given food and water ad libitum. Approximately 3-4 days after arrival to the animal facility, rats underwent surgical implantation of microdialysis guide cannula to guide insertion of the microdialysis probe. Rats are anesthetized with a mixture of ketamine/xylazine (80/6 mg/kg IP) and placed in a stereotaxic apparatus. Ophthalmic lubricating petroleum based ointment is applied to the eyes as needed. The surgical area is shaved and prepared with a betadine scrub and wiped with alcohol. The skull is exposed and small burr holes were drilled to allow for the guide cannula to pass through and for the mounting screws to be attached to the skull. Guide cannula (CMA-12, CMA-Microdialysis, SWE) are stereotaxically implanted towards the NAc-sh (final microdialysis coordinates relative to bregma: A/P+1.70; M/L±0.80; D/V −5.90 from the top of the skull) (Paxinos and Watson, "The Rat Brain", 6$^{th}$ Edition, 2008). Each guide cannula is secured with 3, ⅛" skull screws (Small Parts Inc, USA) and cranioplastic cement (GC Fuji Plus Capsule; Henry Schein, USA). Following 3-4 days of recovery, microdialysis probes (CMA-12, CMA-Microdialysis, SWE) with a 2 mm active membrane length are inserted through the guide cannula and rats are individually tethered to a CMA 120 microdialysis system (CMA-Microdialysis, SWE). Rats are continuously perfused overnight with sterile artificial cerebrospinal fluid (aCSF) (CMA CNS Perfusion Solution; CMA-Microdialysis, SWE) via a syringe pump at 0.2 µl/minute. The following morning, continuous perfusion of aCSF was increased to 2.0 µl/minute and the flow rate was equilibrated for at least 2 hours prior to experimentation.

Microdialysis occurred on the day following probe insertion. Microdialysis samples are collected automatically at 15 minute intervals via a chilled microfraction collector for a total of 6.0 hours. Following equilibration, a 1.5 hour baseline measurement (6 fractions) of neurotransmitter levels is collected. Following baseline measurements, rats are separately administered various concentrations of test compound. Fractions were analyzed via HPLC-EC to determine dopamine concentrations.

Microdialysis fractions are analyzed via HPLC-EC using an Alexys Monoamine Analyzer (Antec Leyden, NLD) or via UHPLC-EC using an Alexys Neurotransmitter Analyzer. For HPLC-EC detection, an aliquot of each fraction (10 ul) is injected onto a 1 µm reverse-phase C18 column (HSS-T3, Waters Corp., Milford, Mass.). DA is eluted using a mobile phase (pH 6.0) consisting of 50 mM phosphoric acid, 8 mM KCL, 0.1 mM EDTA, 6.5% acetonitrile, and 1200 mg/L octane sulfonic acid. DA is detected using a Decade II amperometric detector (Antec Leyden) with a glassy carbon electrode maintained at approximately 0.460V relative to a salt-bridge reference electrode. For UHPLC-EC detection, an aliquot of each fraction (10 ul) is injected onto a 1 µm reverse-phase C18 column (HSS T3, Waters Corp., Milford, Mass.). DA is eluted using a mobile phase (pH 4.00) consisting of 50 mM phosphoric acid, 8 mM KCL, 50 mM Citric Acid, 0.1 mM EDTA, 6.5% acetonitrile, and 600 mg/L octane sulfonic acid. DA is detected using a Decade II amperometric detector (Antec Leyden) with a glassy carbon electrode maintained at approximately 0.55V relative to a Ag/AgCl reference electrode.

All data is recorded and analyte levels quantitated using a Clarity 3.0 software package (Data Apex, Czech Republic). A 6-point standard curve (0.25, 0.5, 1.0, 2.0, 4.0 and 8.0 pg DA/10 µl injection) is run daily prior to neurotransmitter analysis. The standard curve is fitted linearly and neurotransmitter content in microdialysate samples is quantitated based on the corresponding standard curve. The amount of dopamine or metabolites is quantified as "on-column" in picograms of analyte per 10 µl sample injection onto the column Raw data are reported as picograms of dopamine per 10 µl sample and transformed (using Graph Pad Prism 5.0) to percentage of pre-drug baseline for each animal, as defined as the average of the six baseline microdialysis samples. Percentage change from baseline vs. time is then graphed using GraphPad Prism 5.0. Following completion of the study, all animals are analyzed via histological methods to ensure proper probe placement with the nucleus accumbens shell. Those animals with probe placement outside of the nucleus accumbens shell are excluded from the final data analysis To verify probe placement, rats are euthanized with an IP injection of 50% Euthasol (Virbac, AH Inc, Fort Worth, Tex.) shortly after microdialysis. Brains are rapidly dissected and frozen on dry ice and stored at −80° C. Coronal sections (approximately 60-µm) are then sliced at the level of the nucleus accumbens and digitally photographed for archival purposes. Only data from animals with verified probe placement are included in data analysis.

Figure 3:
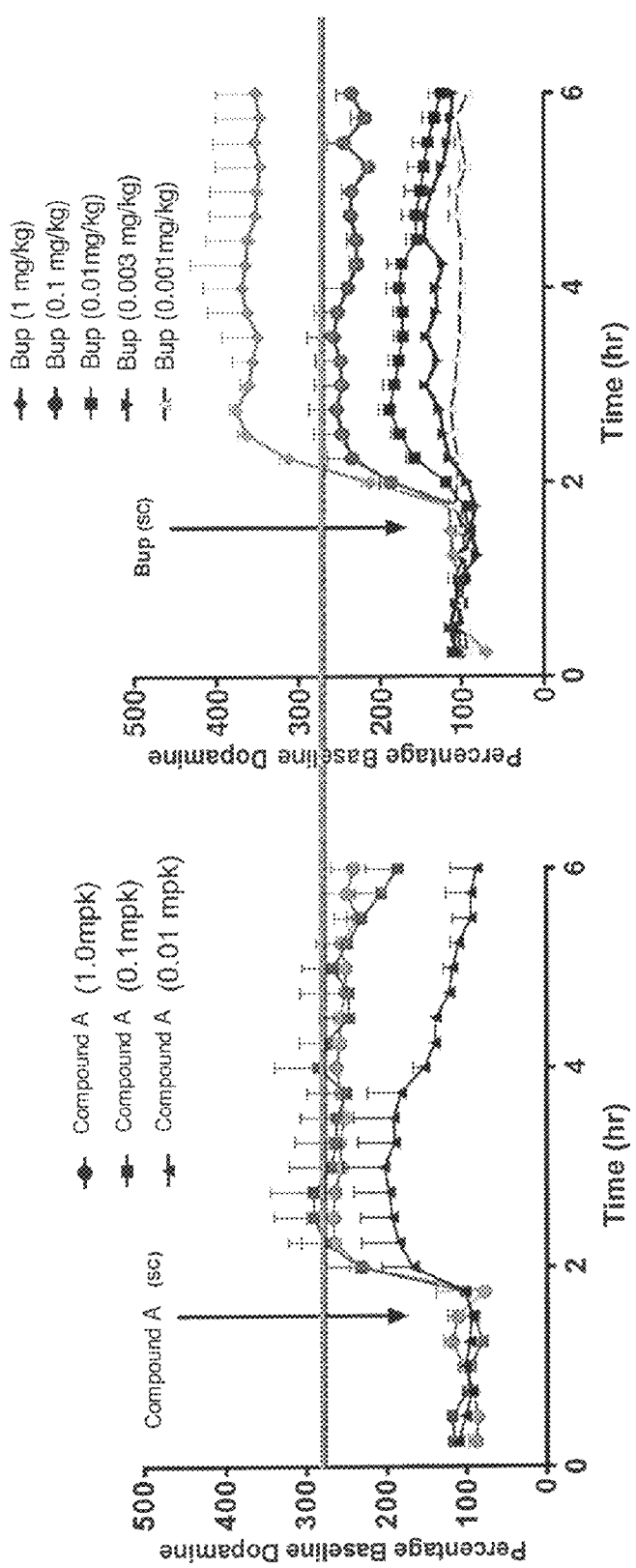
FIG. 3 depicts the results of in vivo microdialysis experiments measuring dopamine release in the rat nucleus accumbens induced by Compound A and buprenorphine.

In one study, the amount of dopamine release induced by Compound A and buprenorphine in the rat nucleus accumbens was determined using the microdialysis assay herein. Specifically, rats were separately administered with Compound A (at 0.01 mg/kg, 0.1 mg/kg, or 1 mg/kg) or buprenorphine (at 0.001 mg/kg, 0.003 mg/kg, 0.01 mg/kg, 0.1 mg/kg, or 1 mg/kg) and microdialysate was sampled for 4.5 hours (18 fractions). The results of these experiments are set forth in FIG. 3. These data show that Compound A induced a dose dependent increase in dopamine efflux in the rat nucleus accumbens, achieving a maximum dopamine efflux of about 300% over baseline at 0.1 mg/kg of Compound A. Buprenorphine also induced a dose dependent increase in dopamine efflux. Although, no maximum dopamine efflux level for buprenorphine was determined, the maximum dopamine efflux induced by buprenorphine is clearly much greater than that obtainable using Compound A. The lower ceiling level of dopamine efflux of exhibited by Compound A relative to buprenorphine indicates that Compound A will likely have a lower risk of opioid dependence, opioid addiction and/or opioid withdrawal symptoms compared to buprenorphine.

In other studies, the amount of dopamine release induced by Compounds B, C, D, and E in the rat nucleus accumbens was determined using the microdialysis assay herein. Specifically, rats were administered (via subcutaneous injection at T=0) separately with Compounds B, C, D, or E at doses of 0.1 mg/kg, 1 mg/kg, or 10 mg/kg, and microdialysate was continuously sampled for 4.5 hours. The results of these experiments are set forth in FIGS. 5-8. Compound B exhibited a maximum dopamine efflux of about 150% to about 200% over baseline at a dose of 10 mg/kg. Compound C exhibited a maximum dopamine efflux of about 125% to about 200% over baseline at the three dose levels. Compounds D and E exhibited a maximum dopamine efflux of about 125% to about 250% over baseline at the three dose levels. These low ceiling levels of dopamine efflux indicate that Compounds B, C, D, and E will likely have a lower risk of opioid dependence, opioid addiction and/or opioid withdrawal symptoms.

B4. In vivo Forced Swim Test

The Forced Swim Test is a classical preclinical model used to assess antidepressant effects of test compounds in rats. Rats forced to swim in an inescapable cylinder adopt a characteristic immobile posture after a period of vigorous swimming Immobility has been shown to be reduced by most clinically effective antidepressant drugs. Furthermore, this paradigm has the benefit of being able to distinguish potential antidepressant compounds from other behavioral paradigms that measure activities (open-field) or other compounds that might have dose-dependent effects on general locomotor activities unrelated to mood.

A male, Wistar-Kyoto rat is placed into its assigned clear Plexiglas cylinders of water (23-25° C.) for a 15-min pretest swim. A compound is then administered in the rat by subcutaneously (sub-Q) injections following a dosing schedule. The sub-Q dosing schedule includes one injection at 0.5 hr after the pretest swim, one injection at 5 hrs before a test swim, and one injection at 1 hr before the test swim. Each test swim lasts 6 minutes, and this test swim is carried out within 24 hours after the pretest swim. The test swim is recorded using a digital video recording system and subsequently analyzed manually for immobility behavior.

In one study, reductions of the duration of immobility in rats induced by different doses of Compounds A, B and C were determined using the Forced Swim Test herein. Specifically, rats were administered with a vehicle (saline), Compound A, Compound B, or Compound C at a dose range between 0 and 10 mg/kg, and durations of immobility were recorded. The results of these experiments are set forth in FIG. 9. Maximal effects of Compounds A, B and C in the Forced Swim Test are shown in FIGS. 9(*a*), 9(*b*) and 9(*c*), respectively. Compounds A, B and C significantly (p<0.05) decreased immobility time in the Forced Swim Test compared to saline treated controls. The reductions of immobility indicate that Compounds A, B and C will likely improve depressive-like behavior.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

INCORPORATION BY REFERENCE

The entire contents of all patents, published patent applications and other references cited herein are hereby expressly incorporated herein in their entireties by reference.

The invention claimed is:

1. A compound of Formula I:

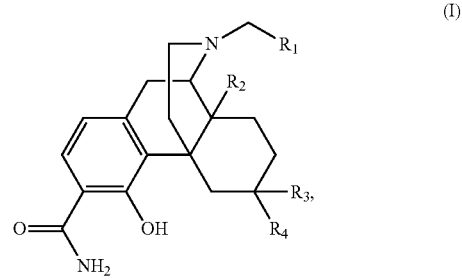

or a pharmaceutically acceptable salt thereof, wherein
$R_1$ is cyclobutyl or

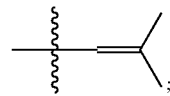

$R_2$ is H or methoxy; and
$R_3$ and $R_4$ are each, independently, H, hydroxyl, or $NR_5R_6$ wherein $R_5$ and $R_6$ are each independently H, alkyl, or substituted acyl, or alternatively, $R_3$ and $R_4$, together with the carbon atom to which they are attached, form C=O or C=CH$_2$.

2. The compound of claim 1, wherein $R_1$ is cyclobutyl.

3. The compound of claim 1, wherein $R_2$ is H.

4. The compound of claim 1, wherein one of $R_3$ or $R_4$, but not both, is hydroxyl, or alternatively, $R_3$ and $R_4$, together with the carbon atom to which they are attached, form C=O.

5. The compound of claim 1, wherein the compound is a μ opioid receptor agonist having an Emax of 5% to 45% in a GTPγS binding assay.

6. The compound of claim 5, wherein the Emax is 15% to 35% in a GTPγS binding assay.

7. The compound of claim 1, having a maximal dopamine efflux in the nucleus accumbens of 125% to 300% over baseline in a rat.

8. The compound of claim 7, having a maximal dopamine efflux in the nucleus accumbens of 200% to 300% over baseline in a rat.

9. The compound of claim 1, wherein the compound does not attenuate thermal pain in a rodent hot plate model when administered at a dose of at least 1 mg/kg.

10. The compound of claim 9, wherein the compound does not attenuate thermal pain in a rodent hot plate model when administered at a dose of at least 3 mg/kg.

11. The compound of claim 9, wherein the compound does not attenuate thermal pain in a rodent hot plate model when administered at a dose of 10 mg/kg.

12. A method of treating a depressive symptom in a subject in need thereof, the method comprising administering to the subject an effective amount of a μ opioid receptor agonist of Formula I:

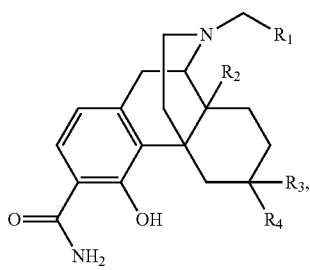
(I)

or a pharmaceutically acceptable salt thereof, wherein
R₁ is cyclobutyl or

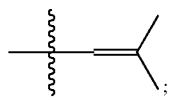 [SMILES: *C=C(C)C]
;

R₂ is H or methoxy; and
R₃ and R₄ are each, independently, H, hydroxyl, or NR₅R₆ wherein R₅ and R₆ are each independently H, alkyl, or substituted acyl, or alternatively, R₃ and R₄, together with the carbon atom to which they are attached, form C═O or C═CH₂,
wherein the μ opioid receptor agonist exhibits an Emax of 5% to 45% in a GTPγS binding assay.

13. A method of treating a depressive symptom in a subject in need thereof, the method comprising administering to the subject an effective amount of a compound of Formula I:

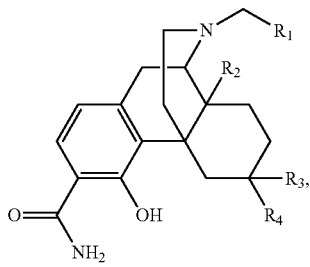
(I)

or a pharmaceutically acceptable salt thereof, wherein
R₁ is cyclobutyl or

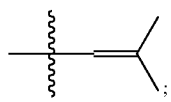 [SMILES: *C=C(C)C]
;

R₂ is H or methoxy; and
R₃ and R₄ are each, independently, H, hydroxyl, or NR₅R₆ wherein R₅ and R₆ are each independently H, alkyl, or substituted acyl, or alternatively, R₃ and R₄, together with the carbon atom to which they are attached, form C═O or C═CH₂,
wherein the compound has a maximal dopamine efflux in the nucleus accumbens of 125% to 300% over base line in a rat.

14. A method of treating a depressive symptom in a subject in need thereof, the method comprising administering to the subject an effective amount of a compound of Formula I:

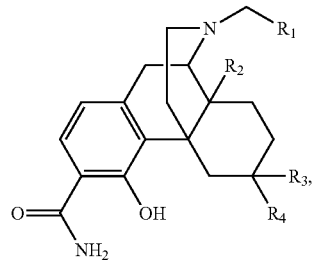
(I)

or a pharmaceutically acceptable salt thereof, wherein
R₁ is cyclobutyl or

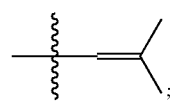
;

R₂ is H or methoxy; and
R₃ and R₄ are each, independently, H, hydroxyl, or NR₅R₆ wherein R₅ and R₆ are each independently H, alkyl, or substituted acyl, or alternatively, R₃ and R₄, together with the carbon atom to which they are attached, form C═O or C═CH₂,
wherein the compound does not attenuate thermal pain in a rodent hot plate model when administered at a dose of at least 1 mg/kg.

15. A method of treating a depressive symptom in a subject in need thereof, comprising administering to the subject the compound of claim 1, or a pharmaceutically acceptable salt thereof.

16. The method of claim 15, wherein the depressive symptom is acute stress disorder, adjustment disorders with depressed mood, Asperger syndrome, attention deficit, bereavement, bipolar I disorder, bipolar II disorder, borderline and personality disorder, cyclothymia and dysthymia, depression such as major depressive disorder (MDD) and treatment-resistant disorder (TRD), Dysthymic disorder, hyperactivity disorder, impulse control disorder, mixed mania, obsessive-compulsive personality disorder (OCD), paranoid, post-traumatic stress disorder, seasonal affective disorder, self-injury separation, sleep disorder, substance-induced mood disorder, Tourette syndrome and tic disorder, and/or Trichotillomania.

17. The compound of claim 1, wherein substituted acyl is

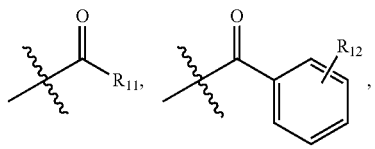
,

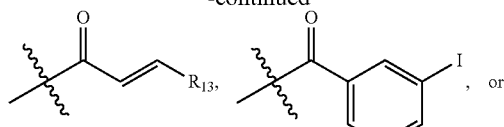
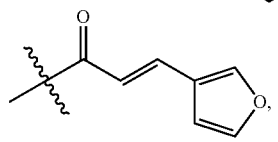
wherein $R_{11}$ is linear or branched $C_1$-$C_6$ alkyl; $R_{12}$ is halo, $C_1$-$C_6$ alkyl, or $C_1$-$C_6$ alkoxy; and $R_{13}$ is aryl or heteroaryl.
* * * * *